(12) United States Patent
Alderete, Jr. et al.

(10) Patent No.: US 8,690,855 B2
(45) Date of Patent: Apr. 8, 2014

(54) FLUID RESERVOIR SEATING PROCEDURE FOR A FLUID INFUSION DEVICE

(75) Inventors: Juan M. Alderete, Jr., Granada Hills, CA (US); Salman Monirabbasi, Los Angeles, CA (US)

(73) Assignee: Medtronic MiniMed, Inc., Northbridge, CA (US)

( * ) Notice: Subject to any disclaimer, the term of this patent is extended or adjusted under 35 U.S.C. 154(b) by 0 days.

(21) Appl. No.: 13/528,258

(22) Filed: Jun. 20, 2012

(65) Prior Publication Data

US 2012/0259282 A1   Oct. 11, 2012

Related U.S. Application Data

(63) Continuation-in-part of application No. 13/225,118, filed on Sep. 2, 2011, now Pat. No. 8,469,942, which is a continuation-in-part of application No. 12/976,591, filed on Dec. 22, 2010, and a continuation-in-part of application No. 12/976,619, filed on Dec. 22, 2010, now Pat. No. 8,197,444.

(51) Int. Cl.
*A61M 31/00*   (2006.01)

(52) U.S. Cl.
USPC ........................................................ 604/503

(58) Field of Classification Search
USPC ................. 604/131, 151, 503, 505
See application file for complete search history.

(56) References Cited

U.S. PATENT DOCUMENTS

| | | | |
|---|---|---|---|
| 3,631,847 A * | 1/1972 | Hobbs, II .................... 600/432 |
| 4,080,653 A * | 3/1978 | Barnes et al. ................ 600/561 |
| 4,212,738 A * | 7/1980 | Henne .......................... 210/94 |
| 4,270,532 A * | 6/1981 | Franetzki et al. ............ 604/151 |
| 4,282,872 A * | 8/1981 | Franetzki et al. ............ 604/67 |
| 4,373,527 A * | 2/1983 | Fischell ..................... 604/891.1 |
| 4,395,259 A * | 7/1983 | Prestele et al. ............... 604/67 |
| 4,433,072 A * | 2/1984 | Pusineri et al. .............. 523/105 |
| 4,443,218 A * | 4/1984 | DeCant et al. ............... 604/67 |
| 4,494,950 A * | 1/1985 | Fischell ........................ 604/66 |
| 4,542,532 A * | 9/1985 | McQuilkin .................... 455/78 |
| 4,550,731 A * | 11/1985 | Batina et al. .................. 607/31 |
| 4,559,037 A * | 12/1985 | Franetzki et al. ............ 604/151 |
| 4,562,751 A * | 1/1986 | Nason et al. .................. 74/111 |
| 4,671,288 A * | 6/1987 | Gough ......................... 600/347 |
| 4,678,408 A * | 7/1987 | Nason et al. ............... 417/410.1 |
| 4,685,903 A * | 8/1987 | Cable et al. .................. 604/154 |

(Continued)

FOREIGN PATENT DOCUMENTS

| | | | | |
|---|---|---|---|---|
| EP | 909911 A2 * | 4/1999 | ............ F16K 11/085 |
| WO | WO 2010078084 A2 * | 7/2010 | ............ A61M 5/142 |

*Primary Examiner* — Aarti B Berdichevsky
(74) *Attorney, Agent, or Firm* — Ingrassia Fisher & Lorenz, P.C.

(57) ABSTRACT

A method of seating a fluid reservoir in a housing of a fluid infusion device is presented here. The method is performed prior to establishing an outgoing fluid flow path from the fluid reservoir. The method begins by detecting insertion of the fluid reservoir into the housing of the fluid infusion device. In response to detecting the insertion, the method determines whether the fluid reservoir is in need of depressurization. When the fluid reservoir is in need of depressurization, the drive motor assembly of the fluid infusion device is rewound to depressurize the fluid reservoir. After depressurizing the fluid reservoir, an equalization state for the fluid reservoir is achieved. After achieving the equilibrium state, the drive motor assembly is advanced to obtain an initial seated state for the fluid reservoir.

6 Claims, 25 Drawing Sheets

(56) References Cited

U.S. PATENT DOCUMENTS

| | | | |
|---|---|---|---|
| 4,731,051 A * | 3/1988 | Fischell | 604/67 |
| 4,731,726 A * | 3/1988 | Allen, III | 600/300 |
| 4,781,798 A * | 11/1988 | Gough | 205/783 |
| 4,803,625 A * | 2/1989 | Fu et al. | 600/483 |
| 4,826,810 A * | 5/1989 | Aoki | 514/5.3 |
| 4,871,351 A * | 10/1989 | Feingold | 604/66 |
| 4,898,578 A * | 2/1990 | Rubalcaba, Jr. | 604/66 |
| 5,003,298 A * | 3/1991 | Havel | 345/83 |
| 5,011,468 A * | 4/1991 | Lundquist et al. | 600/18 |
| 5,019,974 A * | 5/1991 | Beckers | 600/316 |
| 5,050,612 A * | 9/1991 | Matsumura | 600/483 |
| 5,078,683 A * | 1/1992 | Sancoff et al. | 604/67 |
| 5,080,653 A * | 1/1992 | Voss et al. | 604/152 |
| 5,097,122 A * | 3/1992 | Colman et al. | 250/231.14 |
| 5,100,380 A * | 3/1992 | Epstein et al. | 604/67 |
| 5,101,814 A * | 4/1992 | Palti | 600/347 |
| 5,108,819 A * | 4/1992 | Heller et al. | 428/195.1 |
| 5,153,827 A * | 10/1992 | Coutre et al. | 604/111 |
| 5,165,407 A * | 11/1992 | Wilson et al. | 600/345 |
| 5,247,434 A * | 9/1993 | Peterson et al. | 700/83 |
| 5,262,035 A * | 11/1993 | Gregg et al. | 204/403.11 |
| 5,262,305 A * | 11/1993 | Heller et al. | 205/780.5 |
| 5,264,104 A * | 11/1993 | Gregg et al. | 204/403.09 |
| 5,264,105 A * | 11/1993 | Gregg et al. | 204/403.09 |
| 5,284,140 A * | 2/1994 | Allen et al. | 600/373 |
| 5,299,571 A * | 4/1994 | Mastrototaro | 600/347 |
| 5,307,263 A * | 4/1994 | Brown | 600/301 |
| 5,317,506 A * | 5/1994 | Coutre et al. | 604/65 |
| 5,320,725 A * | 6/1994 | Gregg et al. | 205/777.5 |
| 5,322,063 A * | 6/1994 | Allen et al. | 600/347 |
| 5,338,157 A * | 8/1994 | Blomquist | 417/2 |
| 5,339,821 A * | 8/1994 | Fujimoto | 600/513 |
| 5,341,291 A * | 8/1994 | Roizen et al. | 600/300 |
| 5,350,411 A * | 9/1994 | Ryan et al. | 607/32 |
| 5,356,786 A * | 10/1994 | Heller et al. | 205/778 |
| 5,357,427 A * | 10/1994 | Langen et al. | 600/300 |
| 5,368,562 A * | 11/1994 | Blomquist et al. | 604/65 |
| 5,370,622 A * | 12/1994 | Livingston et al. | 604/151 |
| 5,371,687 A * | 12/1994 | Holmes et al. | 710/72 |
| 5,376,070 A * | 12/1994 | Purvis et al. | 604/31 |
| 5,390,671 A * | 2/1995 | Lord et al. | 600/347 |
| 5,391,250 A * | 2/1995 | Cheney et al. | 156/268 |
| 5,403,700 A * | 4/1995 | Heller et al. | 430/311 |
| 5,411,647 A * | 5/1995 | Johnson et al. | 205/777.5 |
| 5,482,473 A * | 1/1996 | Lord et al. | 439/67 |
| 5,485,408 A * | 1/1996 | Blomquist | 703/9 |
| 5,497,772 A * | 3/1996 | Schulman et al. | 600/347 |
| 5,505,709 A * | 4/1996 | Funderburk et al. | 604/155 |
| 5,543,326 A * | 8/1996 | Heller et al. | 204/403.14 |
| 5,569,186 A * | 10/1996 | Lord et al. | 604/67 |
| 5,569,187 A * | 10/1996 | Kaiser | 604/67 |
| 5,573,506 A * | 11/1996 | Vasko | 604/65 |
| 5,582,593 A * | 12/1996 | Hultman | 604/65 |
| 5,586,553 A * | 12/1996 | Halili et al. | 600/316 |
| 5,593,390 A * | 1/1997 | Castellano et al. | 604/187 |
| 5,593,852 A * | 1/1997 | Heller et al. | 435/14 |
| 5,594,638 A * | 1/1997 | Iliff | 705/3 |
| 5,609,060 A * | 3/1997 | Dent | 73/700 |
| 5,626,144 A * | 5/1997 | Tacklind et al. | 600/538 |
| 5,630,710 A * | 5/1997 | Tune et al. | 417/326 |
| 5,643,212 A * | 7/1997 | Coutre et al. | 604/131 |
| 5,660,163 A * | 8/1997 | Schulman et al. | 600/345 |
| 5,660,176 A * | 8/1997 | Iliff | 600/300 |
| 5,665,065 A * | 9/1997 | Colman et al. | 604/65 |
| 5,665,222 A * | 9/1997 | Heller et al. | 205/792 |
| 5,685,844 A * | 11/1997 | Marttila | 604/65 |
| 5,687,734 A * | 11/1997 | Dempsey et al. | 600/509 |
| 5,704,366 A * | 1/1998 | Tacklind et al. | 600/529 |
| 5,750,926 A * | 5/1998 | Schulman et al. | 174/564 |
| 5,754,111 A * | 5/1998 | Garcia | 340/573.1 |
| 5,764,159 A * | 6/1998 | Neftel | 340/870.09 |
| 5,772,635 A * | 6/1998 | Dastur et al. | 604/131 |
| 5,779,665 A * | 7/1998 | Mastrototaro et al. | 604/506 |
| 5,788,669 A * | 8/1998 | Peterson | 604/65 |
| 5,791,344 A * | 8/1998 | Schulman et al. | 600/347 |
| 5,800,420 A * | 9/1998 | Gross et al. | 604/890.1 |
| 5,807,336 A * | 9/1998 | Russo et al. | 604/131 |
| 5,814,015 A * | 9/1998 | Gargano et al. | 604/67 |
| 5,822,715 A * | 10/1998 | Worthington et al. | 702/19 |
| 5,830,180 A * | 11/1998 | Chandler et al. | 604/65 |
| 5,832,448 A * | 11/1998 | Brown | 705/2 |
| 5,840,020 A * | 11/1998 | Heinonen et al. | 600/309 |
| 5,861,018 A * | 1/1999 | Feierbach | 607/60 |
| 5,868,669 A * | 2/1999 | Iliff | 600/300 |
| 5,871,465 A * | 2/1999 | Vasko | 604/65 |
| 5,879,163 A * | 3/1999 | Brown et al. | 434/236 |
| 5,885,245 A * | 3/1999 | Lynch et al. | 604/67 |
| 5,897,493 A * | 4/1999 | Brown | 600/300 |
| 5,899,855 A * | 5/1999 | Brown | 600/301 |
| 5,904,708 A * | 5/1999 | Goedeke | 607/18 |
| 5,913,310 A * | 6/1999 | Brown | 128/897 |
| 5,917,346 A * | 6/1999 | Gord | 327/101 |
| 5,918,603 A * | 7/1999 | Brown | 128/897 |
| 5,925,021 A * | 7/1999 | Castellano et al. | 604/207 |
| 5,933,136 A * | 8/1999 | Brown | 715/741 |
| 5,935,099 A * | 8/1999 | Peterson et al. | 604/65 |
| 5,937,903 A * | 8/1999 | Afshar et al. | 137/625.46 |
| 5,940,801 A * | 8/1999 | Brown | 705/2 |
| 5,956,501 A * | 9/1999 | Brown | 703/11 |
| 5,960,403 A * | 9/1999 | Brown | 705/2 |
| 5,965,380 A * | 10/1999 | Heller et al. | 435/14 |
| 5,972,199 A * | 10/1999 | Heller et al. | 205/777.5 |
| 5,978,236 A * | 11/1999 | Faberman et al. | 363/37 |
| 5,997,476 A * | 12/1999 | Brown | 600/300 |
| 5,999,848 A * | 12/1999 | Gord et al. | 607/2 |
| 5,999,849 A * | 12/1999 | Gord et al. | 607/2 |
| 6,009,339 A * | 12/1999 | Bentsen et al. | 600/322 |
| 6,032,119 A * | 2/2000 | Brown et al. | 705/2 |
| 6,043,437 A * | 3/2000 | Schulman et al. | 174/258 |
| 6,081,736 A * | 6/2000 | Colvin et al. | 600/377 |
| 6,083,710 A * | 7/2000 | Heller et al. | 600/347 |
| 6,088,608 A * | 7/2000 | Schulman et al. | 600/345 |
| 6,101,478 A * | 8/2000 | Brown | 705/2 |
| 6,103,033 A * | 8/2000 | Say et al. | 156/73.1 |
| 6,119,028 A * | 9/2000 | Schulman et al. | 600/345 |
| 6,120,676 A * | 9/2000 | Heller et al. | 205/777.5 |
| 6,121,009 A * | 9/2000 | Heller et al. | 435/14 |
| 6,134,461 A * | 10/2000 | Say et al. | 600/345 |
| 6,143,164 A * | 11/2000 | Heller et al. | 600/583 |
| 6,162,611 A * | 12/2000 | Heller et al. | 435/14 |
| 6,175,752 B1 * | 1/2001 | Say et al. | 600/345 |
| 6,183,412 B1 * | 2/2001 | Benkowski et al. | 600/16 |
| 6,246,992 B1 * | 6/2001 | Brown | 705/2 |
| 6,259,937 B1 * | 7/2001 | Schulman et al. | 600/345 |
| 6,329,161 B1 * | 12/2001 | Heller et al. | 435/14 |
| 6,362,591 B1 * | 3/2002 | Moberg | 318/685 |
| 6,408,330 B1 * | 6/2002 | DeLaHuerga | 709/217 |
| 6,424,847 B1 * | 7/2002 | Mastrototaro et al. | 600/316 |
| 6,472,122 B1 * | 10/2002 | Schulman et al. | 430/311 |
| 6,484,045 B1 * | 11/2002 | Holker et al. | 600/345 |
| 6,484,046 B1 * | 11/2002 | Say et al. | 600/345 |
| 6,485,465 B2 * | 11/2002 | Moberg et al. | 604/154 |
| 6,503,381 B1 * | 1/2003 | Gotoh et al. | 204/403.14 |
| 6,514,718 B2 * | 2/2003 | Heller et al. | 435/14 |
| 6,544,173 B2 * | 4/2003 | West et al. | 600/300 |
| 6,553,263 B1 * | 4/2003 | Meadows et al. | 607/61 |
| 6,554,798 B1 * | 4/2003 | Mann et al. | 604/131 |
| 6,558,320 B1 * | 5/2003 | Causey et al. | 600/300 |
| 6,558,351 B1 * | 5/2003 | Steil et al. | 604/131 |
| 6,560,741 B1 * | 5/2003 | Gerety et al. | 714/752 |
| 6,565,509 B1 * | 5/2003 | Say et al. | 600/365 |
| 6,579,690 B1 * | 6/2003 | Bonnecaze et al. | 435/14 |
| 6,591,125 B1 * | 7/2003 | Buse et al. | 600/347 |
| 6,592,745 B1 * | 7/2003 | Feldman et al. | 205/777.5 |
| 6,605,200 B1 * | 8/2003 | Mao et al. | 204/403.14 |
| 6,605,201 B1 * | 8/2003 | Mao et al. | 204/403.14 |
| 6,607,658 B1 * | 8/2003 | Heller et al. | 205/777.5 |
| 6,616,819 B1 * | 9/2003 | Liamos et al. | 204/403.02 |
| 6,618,934 B1 * | 9/2003 | Feldman et al. | 29/830 |
| 6,623,501 B2 * | 9/2003 | Heller et al. | 606/181 |
| 6,641,533 B2 * | 11/2003 | Causey et al. | 600/300 |
| 6,654,625 B1 * | 11/2003 | Say et al. | 600/347 |
| 6,659,980 B2 * | 12/2003 | Moberg et al. | 604/154 |
| 6,668,858 B1 * | 12/2003 | Bazargan | 137/559 |

(56) References Cited

U.S. PATENT DOCUMENTS

| | | | |
|---|---|---|---|
| 6,671,554 B2 * | 12/2003 | Gibson et al. | 607/37 |
| 6,676,816 B2 * | 1/2004 | Mao et al. | 204/403.14 |
| 6,689,265 B2 * | 2/2004 | Heller et al. | 204/403.09 |
| 6,728,576 B2 * | 4/2004 | Thompson et al. | 607/30 |
| 6,733,471 B1 * | 5/2004 | Ericson et al. | 604/4.01 |
| 6,746,582 B2 * | 6/2004 | Heller et al. | 204/403.06 |
| 6,747,556 B2 * | 6/2004 | Medema et al. | 340/539.12 |
| 6,749,740 B2 * | 6/2004 | Funderburk et al. | 205/792 |
| 6,752,787 B1 * | 6/2004 | Causey et al. | 604/131 |
| 6,809,653 B1 * | 10/2004 | Mann et al. | 340/870.28 |
| 6,817,990 B2 * | 11/2004 | Yap et al. | 604/228 |
| 6,881,551 B2 * | 4/2005 | Heller et al. | 435/14 |
| 6,892,085 B2 * | 5/2005 | McIvor et al. | 600/347 |
| 6,893,545 B2 * | 5/2005 | Gotoh et al. | 204/403.04 |
| 6,895,263 B2 * | 5/2005 | Shin et al. | 600/316 |
| 6,916,159 B2 * | 7/2005 | Rush et al. | 417/321 |
| 6,932,584 B2 * | 8/2005 | Gray et al. | 417/417 |
| 6,932,894 B2 * | 8/2005 | Mao et al. | 204/403.06 |
| 6,942,518 B2 * | 9/2005 | Liamos et al. | 439/495 |
| 7,153,263 B2 * | 12/2006 | Carter et al. | 600/300 |
| 7,153,289 B2 * | 12/2006 | Vasko | 604/131 |
| 7,193,521 B2 * | 3/2007 | Moberg et al. | 340/679 |
| 7,396,330 B2 * | 7/2008 | Banet et al. | 600/300 |
| 7,527,608 B2 * | 5/2009 | Mason | 604/151 |
| 7,621,893 B2 * | 11/2009 | Moberg et al. | 604/151 |
| 7,828,764 B2 * | 11/2010 | Moberg et al. | 604/86 |
| 7,892,206 B2 * | 2/2011 | Moberg et al. | 604/151 |
| 7,905,868 B2 * | 3/2011 | Moberg et al. | 604/232 |
| 7,998,111 B2 * | 8/2011 | Moberg et al. | 604/67 |
| 8,070,723 B2 * | 12/2011 | Bazargan et al. | 604/110 |
| 8,182,447 B2 * | 5/2012 | Moberg et al. | 604/151 |
| 8,197,444 B1 * | 6/2012 | Bazargan et al. | 604/131 |
| 8,469,942 B2 * | 6/2013 | Kow et al. | 604/503 |
| 8,556,856 B2 * | 10/2013 | Bazargan et al. | 604/151 |
| 2001/0034502 A1 | 10/2001 | Moberg et al. | |
| 2001/0044731 A1 * | 11/2001 | Coffman et al. | 705/3 |
| 2002/0013518 A1 * | 1/2002 | West et al. | 600/300 |
| 2002/0043951 A1 * | 4/2002 | Moberg | 318/685 |
| 2002/0055857 A1 * | 5/2002 | Mault | 705/2 |
| 2002/0082665 A1 * | 6/2002 | Haller et al. | 607/60 |
| 2002/0137997 A1 * | 9/2002 | Mastrototaro et al. | 600/345 |
| 2002/0161288 A1 * | 10/2002 | Shin et al. | 600/316 |
| 2003/0060765 A1 * | 3/2003 | Campbell et al. | 604/131 |
| 2003/0073954 A1 | 4/2003 | Moberg et al. | |
| 2003/0078560 A1 * | 4/2003 | Miller et al. | 604/502 |
| 2003/0088166 A1 * | 5/2003 | Say et al. | 600/345 |
| 2003/0144581 A1 * | 7/2003 | Conn et al. | 600/309 |
| 2003/0152823 A1 * | 8/2003 | Heller | 429/43 |
| 2003/0176183 A1 * | 9/2003 | Drucker et al. | 455/414.1 |
| 2003/0188427 A1 * | 10/2003 | Say et al. | 29/846 |
| 2003/0199744 A1 * | 10/2003 | Buse et al. | 600/347 |
| 2003/0208113 A1 * | 11/2003 | Mault et al. | 600/316 |
| 2003/0220552 A1 * | 11/2003 | Reghabi et al. | 600/365 |
| 2004/0061232 A1 * | 4/2004 | Shah et al. | 257/758 |
| 2004/0061234 A1 * | 4/2004 | Shah et al. | 257/758 |
| 2004/0064133 A1 * | 4/2004 | Miller et al. | 604/890.1 |
| 2004/0064156 A1 * | 4/2004 | Shah et al. | 607/6 |
| 2004/0073095 A1 * | 4/2004 | Causey et al. | 600/300 |
| 2004/0074785 A1 * | 4/2004 | Holker et al. | 205/777.5 |
| 2004/0085215 A1 * | 5/2004 | Moberg et al. | 340/679 |
| 2004/0093167 A1 * | 5/2004 | Braig et al. | 702/23 |
| 2004/0097796 A1 * | 5/2004 | Berman et al. | 600/310 |
| 2004/0102683 A1 * | 5/2004 | Khanuja et al. | 600/300 |
| 2004/0111017 A1 * | 6/2004 | Say et al. | 600/347 |
| 2004/0122353 A1 * | 6/2004 | Shahmirian et al. | 604/65 |
| 2004/0167465 A1 * | 8/2004 | Mihai et al. | 604/67 |
| 2004/0263354 A1 * | 12/2004 | Mann et al. | 340/870.28 |
| 2005/0038331 A1 * | 2/2005 | Silaski et al. | 600/347 |
| 2005/0038680 A1 * | 2/2005 | McMahon | 705/3 |
| 2005/0154271 A1 * | 7/2005 | Rasdal et al. | 600/347 |
| 2005/0192557 A1 * | 9/2005 | Brauker et al. | 604/503 |
| 2006/0184154 A1 * | 8/2006 | Moberg et al. | 604/506 |
| 2006/0229694 A1 * | 10/2006 | Schulman et al. | 607/116 |
| 2006/0238333 A1 * | 10/2006 | Welch et al. | 340/539.12 |
| 2006/0293571 A1 * | 12/2006 | Bao et al. | 600/300 |
| 2007/0088521 A1 * | 4/2007 | Shmueli et al. | 702/127 |
| 2007/0135866 A1 * | 6/2007 | Baker et al. | 607/60 |
| 2007/0149926 A1 * | 6/2007 | Moberg et al. | 604/152 |
| 2008/0154503 A1 * | 6/2008 | Wittenber et al. | 701/300 |
| 2008/0221522 A1 * | 9/2008 | Moberg et al. | 604/151 |
| 2008/0221523 A1 * | 9/2008 | Moberg et al. | 604/151 |
| 2009/0081951 A1 * | 3/2009 | Erdmann et al. | 455/41.2 |
| 2009/0082635 A1 * | 3/2009 | Baldus et al. | 600/300 |
| 2010/0037680 A1 * | 2/2010 | Moberg et al. | 73/37 |
| 2010/0164727 A1 * | 7/2010 | Bazargan et al. | 340/573.1 |
| 2010/0168670 A1 * | 7/2010 | Srisathapat et al. | 604/111 |
| 2010/0168711 A1 * | 7/2010 | Bazargan et al. | 604/404 |
| 2011/0119033 A1 * | 5/2011 | Moberg et al. | 702/183 |
| 2011/0160667 A1 * | 6/2011 | Bazargan et al. | 604/151 |
| 2011/0224614 A1 * | 9/2011 | Moberg et al. | 604/151 |
| 2012/0160033 A1 * | 6/2012 | Kow et al. | 73/861.71 |
| 2012/0165733 A1 * | 6/2012 | Bazargan et al. | 604/131 |
| 2012/0215169 A1 * | 8/2012 | Moberg et al. | 604/151 |
| 2012/0215199 A1 * | 8/2012 | Moberg et al. | 604/500 |
| 2012/0226234 A1 * | 9/2012 | Bazargan et al. | 604/111 |
| 2012/0259282 A1 * | 10/2012 | Alderete et al. | 604/131 |
| 2013/0133438 A1 * | 5/2013 | Kow et al. | 73/862.381 |
| 2013/0237953 A1 * | 9/2013 | Kow et al. | 604/500 |
| 2013/0245595 A1 * | 9/2013 | Kow et al. | 604/500 |

* cited by examiner

FLUID RESERVOIR SEATING PROCEDURE FOR A FLUID INFUSION DEVICE

CROSS-REFERENCE TO RELATED APPLICATION(S)

This application is a continuation-in-part of U.S. patent application Ser. No. 13/225,118, filed Sep. 2, 2011, which is a continuation-in-part of U.S. patent application Ser. No. 12/976,591, filed Dec. 22, 2010, and a continuation-in-part of U.S. patent application Ser. No. 12/976,619, filed Dec. 22, 2010 (now issued as U.S. Pat. No. 8,197,444).

TECHNICAL FIELD

Embodiments of the subject matter described herein relate generally to medical devices. More particularly, embodiments of the subject matter relate to fluid infusion devices such as personal insulin infusion pumps.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level.

A typical infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a stopper in a reservoir. The fluid containment assembly typically includes the reservoir with the stopper, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

Some fluid infusion devices use sensors and alarm features designed to detect and indicate certain operating conditions, such as non-delivery of the medication to the patient due to a fluid path occlusion. In this regard, a force sensor can be used in a fluid infusion device to detect when the force applied to the fluid reservoir stopper reaches a set point. The force sensor in such a fluid infusion device could be positioned at the end of the drive motor assembly that actuates a rotatable lead screw, which in turn advances the stopper of the reservoir. With such an arrangement, the force applied to the force sensor by the drive motor assembly is proportional to the pressure applied to the medication as a result of power supplied to the drive system to advance the stopper. Thus, when a certain force threshold (a set point corresponding to an occlusion condition) is reached, the fluid infusion device is triggered to generate an alarm to warn the user.

Early detection of an occlusion condition is helpful, because an occlusion can result in "under-dosing," particularly if the drive system continues to receive commands to deliver medication when the fluid path is blocked. Accordingly, proper operation of the force sensor is important for purposes of occlusion detection, and it is desirable to have some diagnostic capability related to the health of the force sensor.

Existing force-based occlusion detection techniques typically rely on a fixed threshold or set point that is indicative of an occlusion condition. A threshold value is selected based on system tolerances. To avoid frequent false alarms, however, it is necessary to set the threshold value above the maximum expected force, based on the interacting system components. Because the threshold value is set at the maximum expected force, if a patient has a particular pump system with a nominal delivery force, it may take slightly longer to reach the threshold force. Accordingly, it is desirable to have an occlusion detection technique that does not solely rely on a fixed occlusion detection threshold force.

Some fluid infusion devices use replaceable fluid reservoirs that are secured in the housing of the device and actuated by a drive assembly. One form of infusion pump utilizes a threaded cap to seat and secure the fluid reservoir in the housing of the pump. The user unscrews the threaded cap to remove an empty reservoir, replaces the old reservoir with a new reservoir, and reinstalls the threaded cap to secure the new reservoir in place. During use, the threaded cap might be dislodged (especially if the fluid infusion device is a portable unit that is worn by the patient), resulting in an unseated or improperly installed reservoir. For example, if the user participates in certain physical activities (e.g., sports, hiking, or rigorous exercise), then the cap might be unintentionally loosened by physical rotation. As another example, if the user is in a crowded environment (e.g., a concert, a nightclub, or a full elevator), then the cap might be inadvertently unscrewed through contact with another person or an object. For this reason, it is desirable to have a reservoir presence and/or seating detection technique for a fluid infusion pump.

BRIEF SUMMARY

A method of operating a fluid infusion device is provided. The fluid infusion device includes a drive motor assembly and a force sensor associated with the drive motor assembly. The method activates a rewind operation of the drive motor assembly and determines a rewind force imparted to the force sensor during the rewind operation. The method initiates corrective action for the fluid infusion device when the rewind force is less than a lower threshold force or greater than an upper threshold force.

Also provided is an exemplary embodiment of a device for delivering fluid to a user. The device includes: a housing; a drive motor assembly in the housing to regulate delivery of fluid by actuating a piston of a fluid reservoir; a force sensor associated with the drive motor assembly to generate output levels in response to force imparted thereto; and an electronics module coupled to the force sensor to process the output levels to determine operating health of the force sensor.

Another embodiment of a method of operating a fluid infusion device is also provided. The fluid infusion device includes a drive motor assembly and a force sensor associated with the drive motor assembly. The method involves determining a measure of actuation force imparted to the force sensor during a fluid delivery action of the drive motor assembly, and comparing the measure of actuation force against a range of valid values that represents normally expected measures of actuation forces. When the measure of actuation force is outside the range of valid values, the method initiates corrective action for the fluid infusion device.

A method of determining a seating status of a fluid reservoir in the reservoir cavity of a fluid infusion device is also provided. The fluid infusion device includes a drive motor assembly, a force sensor associated with the drive motor assembly, and a reservoir cavity that accommodates fluid reservoirs. The method begins by confirming initial seating of the fluid reservoir in the reservoir cavity. The method continues by determining a measure of actuation force imparted to the force sensor during a fluid delivery action of the drive motor assembly, and comparing the measure of actuation force to an amount of force that is less than normally expected actuation forces of the fluid infusion device, where the amount of force is indicative of an unseated state of the fluid reservoir. The method continues by initiating corrective action for the fluid infusion device when the measure of actuation force is less than the amount of force.

A device for delivering fluid to a user is also provided. The device includes: a housing; a reservoir cavity within the housing to accommodate fluid reservoirs; a drive motor assembly in the housing to regulate delivery of fluid by actuating a piston of a fluid reservoir; a force sensor associated with the drive motor assembly to generate output levels in response to force imparted thereto; and an electronics module coupled to the force sensor to process the output levels to determine a seating status of the fluid reservoir in the reservoir cavity.

Another embodiment of a method of determining a seating status of a fluid reservoir in the reservoir cavity of a fluid infusion device is provided. The method obtains baseline actuation force imparted to a force sensor, after initial seating and priming of the fluid reservoir. The method continues by determining a measured actuation force imparted to the force sensor, the measured actuation force corresponding to a designated delivery stroke of the drive motor assembly. The method also generates indicia of an unseated reservoir condition when the measured actuation force is less than the baseline actuation force by at least a predetermined amount of force.

Also provided is a method of determining a seating status of a fluid reservoir in a fluid infusion device having a drive motor assembly that actuates the fluid reservoir using discrete delivery pulses. The method obtains measures of actuation force imparted to the force sensor for a number of consecutive fluid delivery pulses, and calculates a pulse-to-pulse difference between consecutive fluid delivery pulses, the pulse-to-pulse difference based on respective measures of actuation force for the consecutive fluid delivery pulses. The method continues by initiating corrective action for the fluid infusion device when the pulse-to-pulse difference is greater than a threshold force value.

Another embodiment of a method of determining a seating status of a fluid reservoir in a fluid infusion device is provided. The infusion device has a drive motor assembly that actuates the fluid reservoir using discrete delivery pulses, and the method involves: maintaining a count that is indicative of the seating status; storing an adaptive reference force value that corresponds to a previously recorded measure of actuation force imparted to the force sensor during a previous fluid delivery pulse; obtaining a current measure of actuation force imparted to the force sensor for a current fluid delivery pulse; changing the count when the current measure of actuation force is less than the difference between the adaptive reference force value and a threshold force value, resulting in an updated count; and generating a seating status alert when the updated count satisfies predetermined alert criteria.

An exemplary embodiment of a fluid infusion device includes a drive motor assembly and a force sensor associated with the drive motor assembly. A method of detecting occlusions in a fluid path of the fluid infusion device determines a plurality of force measurements for a fluid delivery action of the drive motor assembly, the plurality of force measurements indicating measures of actuation force imparted to the force sensor for the fluid delivery action. The method continues by determining a plurality of quantity measurements for the fluid delivery action, each of the plurality of quantity measurements being determined relative to a reference quantity measurement. An occlusion is indicated when a first slope of force-versus-quantity for a large sample of the plurality of quantity measurements is greater than or equal to a first threshold slope value. An occlusion is also indicated when: (a) a second slope of force-versus-quantity for a small sample of the plurality of quantity measurements is greater than or equal to a second threshold slope value; and (b) a current one of the plurality of force measurements is greater than or equal to a threshold force value.

An exemplary embodiment of a method of detecting occlusions in a fluid path of a fluid infusion device is also provided. The fluid infusion device has a drive motor assembly that actuates a piston of a fluid reservoir to deliver fluid from the fluid reservoir. The method begins by initiating a fluid delivery action to deliver an amount of fluid from the fluid reservoir. The method continues by determining, for each of a plurality of measurement points associated with the fluid delivery action, a respective measurement of a quantity that is indicative of pressure in the fluid path, along with a respective delivered volume measurement relative to a reference volume measurement. A first slope is calculated based upon a current measurement of the quantity, a previous measurement of the quantity, a current delivered volume measurement corresponding to the current measurement of the quantity, and a previous delivered volume measurement corresponding to the previous measurement of the quantity. A second slope is calculated based upon the current measurement of the quantity, an intervening measurement of the quantity that is determined after determining the previous measurement of the quantity, the current delivered volume measurement, and an intervening delivered volume measurement corresponding to the intervening measurement of the quantity. The method continues by indicating whether an occlusion has occurred by using the first slope and the second slope.

Also provided is an exemplary embodiment of a method of detecting occlusions in a fluid path of a fluid infusion device having a drive motor assembly that actuates a fluid reservoir by applying actuation force to a piston of the fluid reservoir. The method involves initiating a fluid delivery action intended to deliver an amount of fluid from the fluid reservoir, and determining measures of fluid pressure in the fluid path for the fluid delivery action. The method indicates an occlusion when a first rate of change of the measures of fluid pressure is greater than or equal to first threshold value, the first rate of change based upon a first measurement window. The method also indicates an occlusion when: (a) a second rate of change of the measures of fluid pressure is greater than or equal to a second threshold value, the second rate of change based upon a second measurement window; and (b) a current measure of fluid pressure is greater than or equal to a threshold force value.

A device for delivering fluid to a user is also provided. The device includes a housing, a reservoir cavity within the housing to accommodate fluid reservoirs, a drive motor assembly in the housing to regulate delivery of fluid by actuating a piston of a fluid reservoir, a force sensor associated with the drive motor assembly to generate output levels in response to force imparted thereto, and an electronics module coupled to the force sensor. The electronics module processes the output levels to detect occlusions in a fluid path of the device for a fluid delivery action.

Another method of seating a fluid reservoir is provided. The method seats the fluid reservoir in a housing of a fluid infusion device prior to establishing an outgoing fluid flow path from the fluid reservoir. The method detects insertion of the fluid reservoir into the housing and, in response to the detecting, determines whether the fluid reservoir is in need of depressurization. When the fluid reservoir is in need of depressurization, the drive motor assembly is rewound to depressurize the fluid reservoir. After depressurizing the fluid reservoir, an equilibrium state for the fluid reservoir is achieved. After achieving the equilibrium state, the method advances the drive motor assembly to obtain an initial seated state for the fluid reservoir.

Yet another method of seating a fluid reservoir is provided. The method seats the fluid reservoir in a housing of a fluid infusion device prior to establishing an outgoing fluid flow path from the fluid reservoir. The fluid infusion device includes a drive motor assembly, an actuation mechanism operatively coupled to the drive motor assembly for actuation of a plunger of the fluid reservoir, and a force sensor operatively coupled to the actuation mechanism. The method begins by detecting insertion of the fluid reservoir into the housing, wherein insertion of the fluid reservoir into the housing causes a shaft of the plunger to engage the actuation mechanism. After detecting insertion of the fluid reservoir, the method obtains a first measure of force using the force sensor, wherein the first measure of force is associated with interaction of the shaft with the actuation mechanism. The method continues by comparing the first measure of force to a first threshold force value. When the first measure of force is greater than the first threshold force value, the fluid reservoir is depressurized. After depressurizing the fluid reservoir, or when the first measure of force is not greater than the first threshold force value, the drive motor assembly is rewound to achieve an equilibrium state for the fluid reservoir. After rewinding the drive motor assembly to achieve the equilibrium state, the drive motor assembly is advanced to obtain an initial seated state for the fluid reservoir.

A fluid infusion device is also presented here. The fluid infusion device includes a housing that receives a sealed fluid reservoir, wherein the fluid reservoir has a plunger and a shaft coupled to the plunger. The fluid infusion device also includes a drive motor assembly, an actuation mechanism, a force sensor, and at least one processor in the housing. The actuation mechanism is operatively coupled to the drive motor assembly, and the force sensor is operatively coupled to the actuation mechanism to obtain measures of force associated with interaction of the shaft with the actuation mechanism. The processor is operatively coupled to the drive motor assembly and the force sensor, and the processor detects insertion of the fluid reservoir into the housing and thereafter incrementally rewinds the drive motor assembly to achieve an equilibrium state for the fluid reservoir. Next, the processor advances the drive motor assembly and obtains at least one measure of force using the force sensor until the at least one measure of force indicates that the fluid reservoir has reached an initial seated state. Thereafter, the processor performs a stabilizing cycle with the drive motor assembly to stabilize the fluid reservoir. Thereafter, the processor advances the drive motor assembly and obtains at least one subsequent measure of force using the force sensor until the at least one subsequent measure of force indicates that the fluid reservoir has reached a subsequent sealed state.

Also presented here is a method of seating a fluid reservoir in a housing of a fluid infusion device prior to establishing an outgoing fluid flow path from the fluid reservoir. The fluid infusion device includes a drive motor assembly, an actuation mechanism operatively coupled to the drive motor assembly for actuation of a plunger shaft of the fluid reservoir, and a force sensor operatively coupled to the actuation mechanism. The method begins by obtaining a first measure of force using the force sensor, wherein the first measure of force is associated with interaction of the plunger shaft with the actuation mechanism. The method continues by determining that the first measure of force is greater than a first threshold force value. In response to the determining, the method depressurizes the fluid reservoir by rewinding the drive motor assembly by a first rewind amount. After depressurizing the fluid reservoir, the drive motor assembly is rewound by a second rewind amount to achieve an equilibrium state for the fluid reservoir. After rewinding the drive motor assembly by the second amount, the drive motor assembly is advanced by a first forward amount to obtain an initial seated state for the fluid reservoir. After obtaining the initial seated state, the drive motor assembly is advanced by a second forward amount and, thereafter, the drive motor assembly is rewound by a third rewind amount to stabilize the fluid reservoir. After rewinding the drive motor assembly by the third rewind amount, the drive motor assembly is advanced by a third forward amount to obtain a subsequent seated state for the fluid reservoir.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
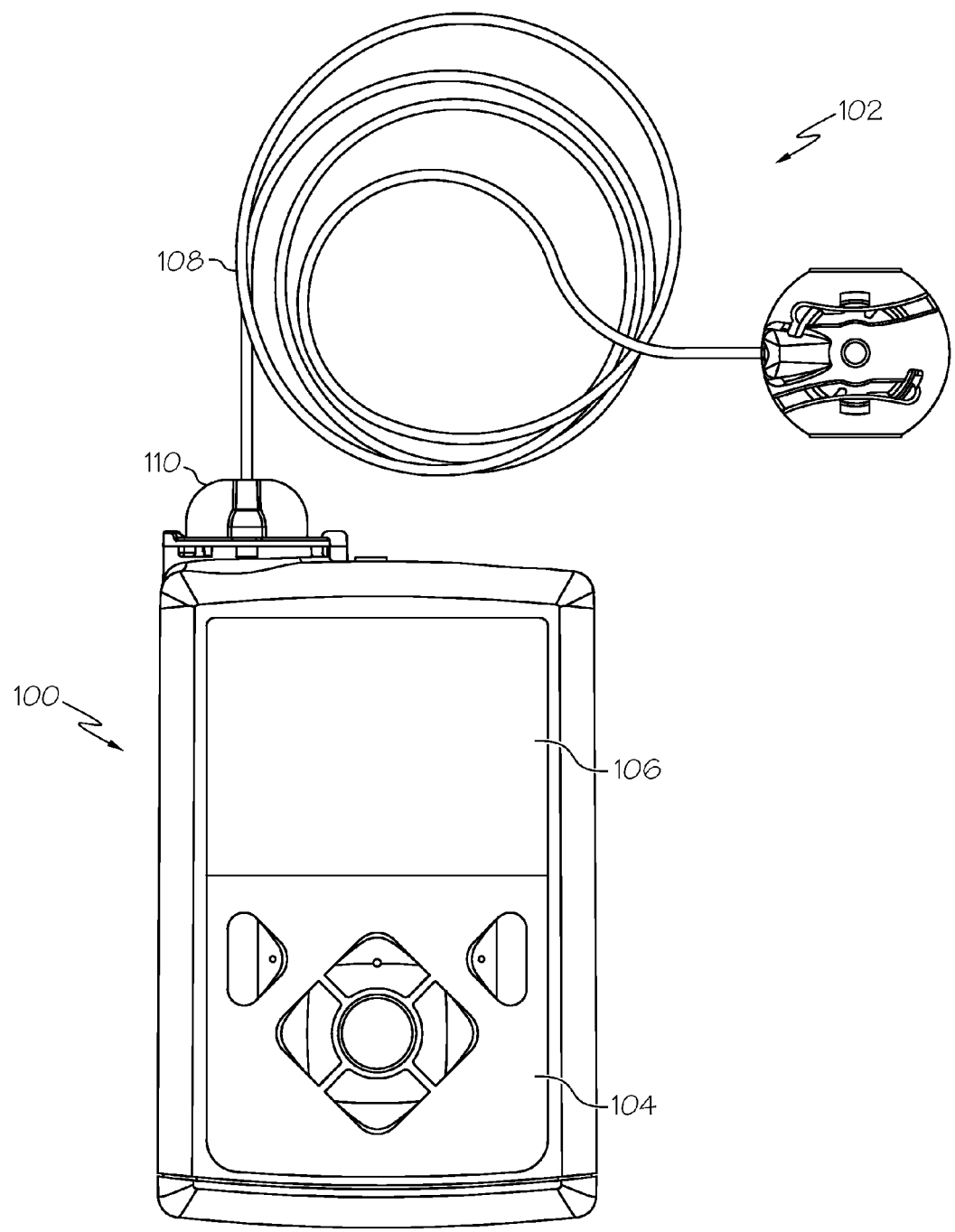
FIG. 1 is a schematic representation of an embodiment of a fluid infusion device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to infusion system operation, insulin pump and/or infusion set operation, blood glucose sensing and monitoring, force sensors, signal processing, and other functional aspects of the systems (and the individual operating components of the systems) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

The subject matter described here relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

A methodology for monitoring the operational health of a sensor (e.g., a force sensor) is implemented by an exemplary embodiment of a fluid infusion device. The fluid infusion device monitors force measurements obtained from the force sensor during a motor rewind operation to determine whether or not the force sensor might be out of calibration, on the verge of failure, or the like. The force normally experienced by the force sensor during rewind operations should be zero or close to zero, due to the absence of a fluid reservoir in the fluid infusion device, and because the fluid infusion device is driving in rewind mode, i.e., away from the plunger of the fluid reservoir. Accordingly, the fluid infusion device can assume that a properly functioning force sensor will produce rewind force readings in the neighborhood of zero or close to zero. Thus, if a rewind force measurement significantly deviates from the assumed baseline value (or range of values), then the fluid infusion device can take appropriate corrective action.

Another methodology for monitoring the operational health of a force sensor obtains force readings during a fluid delivery operation and compares the force readings to determine whether or not the force sensor is operating as expected. This alternate methodology measures the forces associated with individual fluid delivery strokes or drive motor pulses. Under normal and typical operating conditions, these forces will be relatively stable during one fluid delivery operation, and the variation from one stroke to another will be slight (absent an external impact or shock suffered by the fluid infusion device). Thus, if the force sensor reading is out of the expected operating range during a fluid delivery operation, the fluid infusion device can take appropriate corrective action. For example, if the force sensor output during fluid delivery happens to be −0.5 pounds, then clearly there is a problem because in reality the measured force should not be a negative value.

A fluid infusion device may also have an occlusion detection feature that determines when the fluid delivery path is occluded. Occlusion detection techniques are usually based on sensor measurements (force, pressure, stress) that are influenced by the flow status of the fluid delivery path. An exemplary embodiment of a fluid infusion device as described here employs an adaptive occlusion detection technique that need not rely on a fixed occlusion detection force threshold. Instead, the adaptive occlusion detection technique evaluates the rate of change of a metric associated with force variations per units of fluid to be delivered. For example, the typical force variation for a fluid reservoir might result in a variation of about ±X pounds per unit (lb/U) over a set number of delivery strokes (or drive motor pulses). If, however, the fluid infusion device detects a significant increase in this metric during a fluid delivery operation (e.g., ±Y lb/U, where Y is significantly larger than X) over the same set number of delivery strokes, then the fluid infusion device can take appropriate corrective action. The values of X and Y can also be in units of lb/pulse or the like. An example of a corrective action might be, but not limited to, immediately indicate or warn of an occlusion or simply lower the set threshold value by a set constant or percentage and allow the pump to continue delivery for a set number of pulses or units to see if the pump recovers (recovery might occur in the case of a kinked cannula). The adaptive occlusion detection methodology allows the fluid infusion device to determine the existence of an occlusion much quicker, relative to a fixed threshold based methodology. Quicker occlusion detection is made possible because the fluid infusion device need not be operated until a high threshold force is reached; rather, occlusion can be detected earlier without having to wait for a high force condition.

An exemplary embodiment of a fluid infusion device may also be configured to determine whether or not a fluid reservoir is properly seated and installed. The presence (or lack thereof) of the fluid reservoir is determined based upon force sensor readings that are obtained after proper initial installation and seating of the fluid reservoir. In accordance with one embodiment, one or more force thresholds are used to determine whether or not the fluid reservoir is properly seated. If a measured force does not satisfy a force threshold that is indicative of proper reservoir seating, then the fluid infusion device can take corrective action. In accordance with another exemplary embodiment, the fluid infusion device measures and processes the forces associated with individual fluid delivery strokes or drive motor pulses to determine when the fluid reservoir has been dislodged, removed, or unseated.

Another exemplary embodiment of a fluid infusion device is realized in the form of a compact wearable infusion pump that includes a base plate component that is affixed to the skin of the patient, along with a durable housing that can be removably coupled to the base plate component. The base plate component includes a subcutaneous fluid delivery conduit (such as a cannula) that remains in place until the base plate component is replaced. The durable housing is designed to receive and actuate a fluid reservoir, which is in fluid communication with the fluid delivery conduit when the durable housing is coupled to the base plate component. The "open flow" nature of the fluid delivery path (which includes the subcutaneous fluid delivery conduit) presents certain challenges associated with installation, seating, and actuation of the fluid reservoir. Accordingly, an exemplary embodiment of a reservoir seating process is also presented here, where the disclosed reservoir seating process is suitable for use with an open path delivery system such as that employed by the compact wearable infusion pump.

FIG. 1 is a plan view of an exemplary embodiment of a fluid infusion device 100. FIG. 1 also shows an infusion set 102 coupled to the fluid infusion device 100. The fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

This embodiment shown in FIG. 1 includes a user interface 104 that includes several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators; etc. In some embodiments, the display element 106 is realized as a touch screen display element and, therefore, the display element 106 also serves as a user interface component.

The fluid infusion device 100 accommodates a fluid reservoir (hidden from view in FIG. 1) for the fluid to be delivered to the user. A length of tubing 108 is the flow path that couples the fluid reservoir to the infusion set 102. The tubing 108 extends from the fluid infusion device 100 to the infusion set 102, which provides a fluid pathway with the body of the user. A removable cap or fitting 110 is suitably sized and configured to accommodate replacement of fluid reservoirs (which are typically disposable) as needed. In this regard, the fitting 110 is designed to accommodate the fluid path from the fluid reservoir to the tubing 108.

Figure 2:
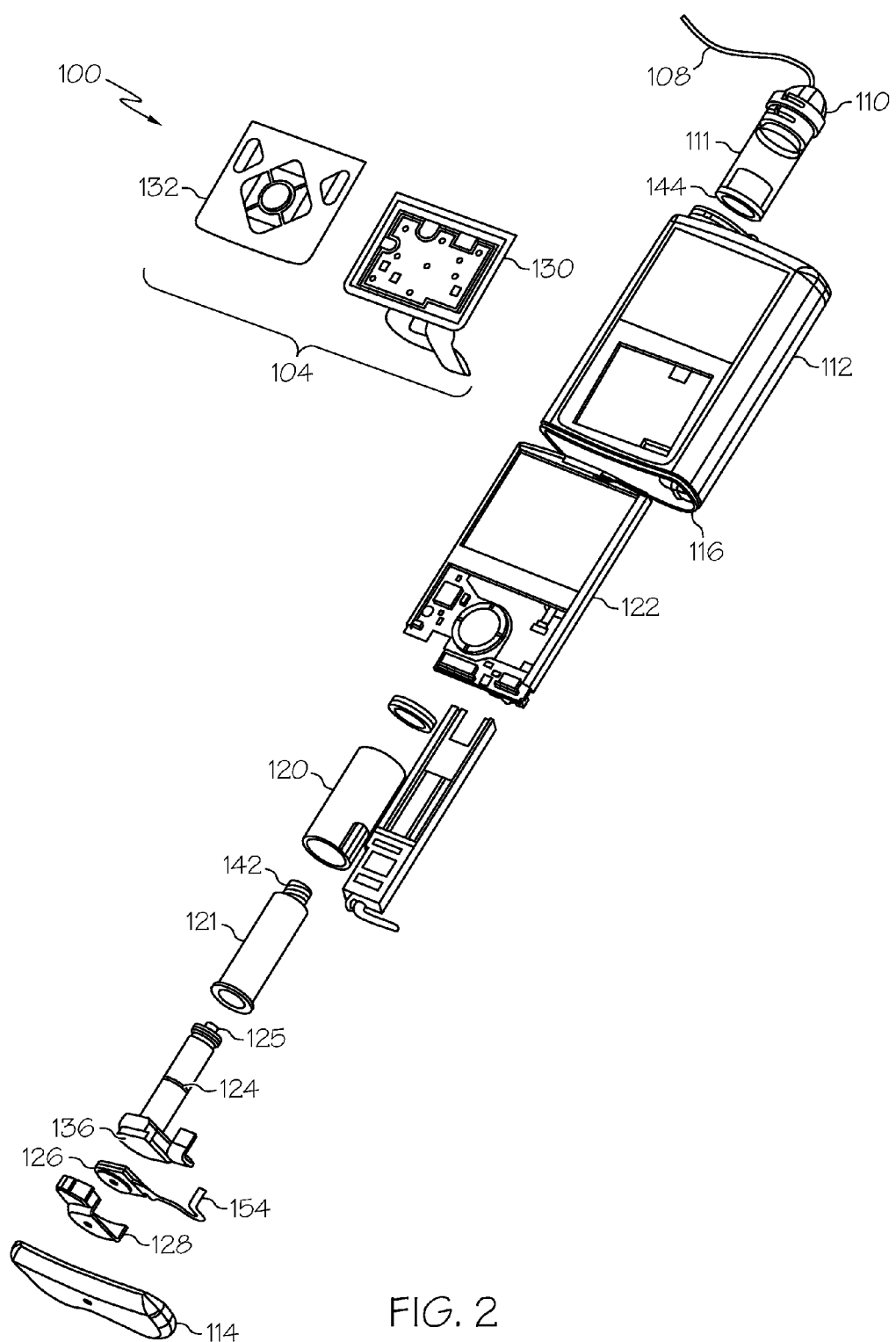
FIG. 2 is an exploded perspective view of the fluid infusion device shown in FIG. 1.

FIG. 2 is an exploded perspective view of the fluid infusion device 100. For the sake of brevity and simplicity, FIG. 2 is a simplified depiction of the fluid infusion device 100 that does not include all of the elements, components, and features that would otherwise be present in a typical embodiment. It should be appreciated that a deployed implementation of the fluid infusion device 100 will include additional features, components, and elements that are not shown in the figures.

The embodiment of the fluid infusion device 100 illustrated in FIG. 2 includes a housing 112 and a housing end cap 114 that is coupled to an end 116 of the housing 112 to enclose components within the housing 112. These internal components include, without limitation: a battery tube subassembly 118; a sleeve 120; a slide 121; an electronics assembly 122; a drive motor assembly 124 having a drive screw 125; a force sensor 126; and a motor support cap 128. FIG. 2 also depicts some components that are located outside the housing 112, namely, a keypad assembly 130 and a graphic keypad overlay 132 for the keypad assembly 130. The keypad assembly 130 and the graphic keypad overlay 132 may be considered to be part of the user interface 104 of the fluid infusion device 100. The outer edge of the motor support cap 128 is attached to the interior side of the housing 112, and the motor support cap 128 contacts the force sensor 126 to remove assembly tolerances from the drive motor assembly 124. FIG. 2 also depicts an exemplary fluid reservoir 111, which is inserted into a reservoir cavity defined within the housing 112. The reservoir cavity is configured, sized, and shaped to accommodate fluid reservoirs, and the fluid reservoir 111 is maintained in the reservoir cavity using the fitting 110. The electronics assembly 122 may include a suitably configured electronics module (not shown in FIG. 2; see FIG. 4 and related description below), which may include or cooperate with a power supply, at least one memory element, at least one processor, processing logic, and device software, firmware, and application programs.

Figure 3:
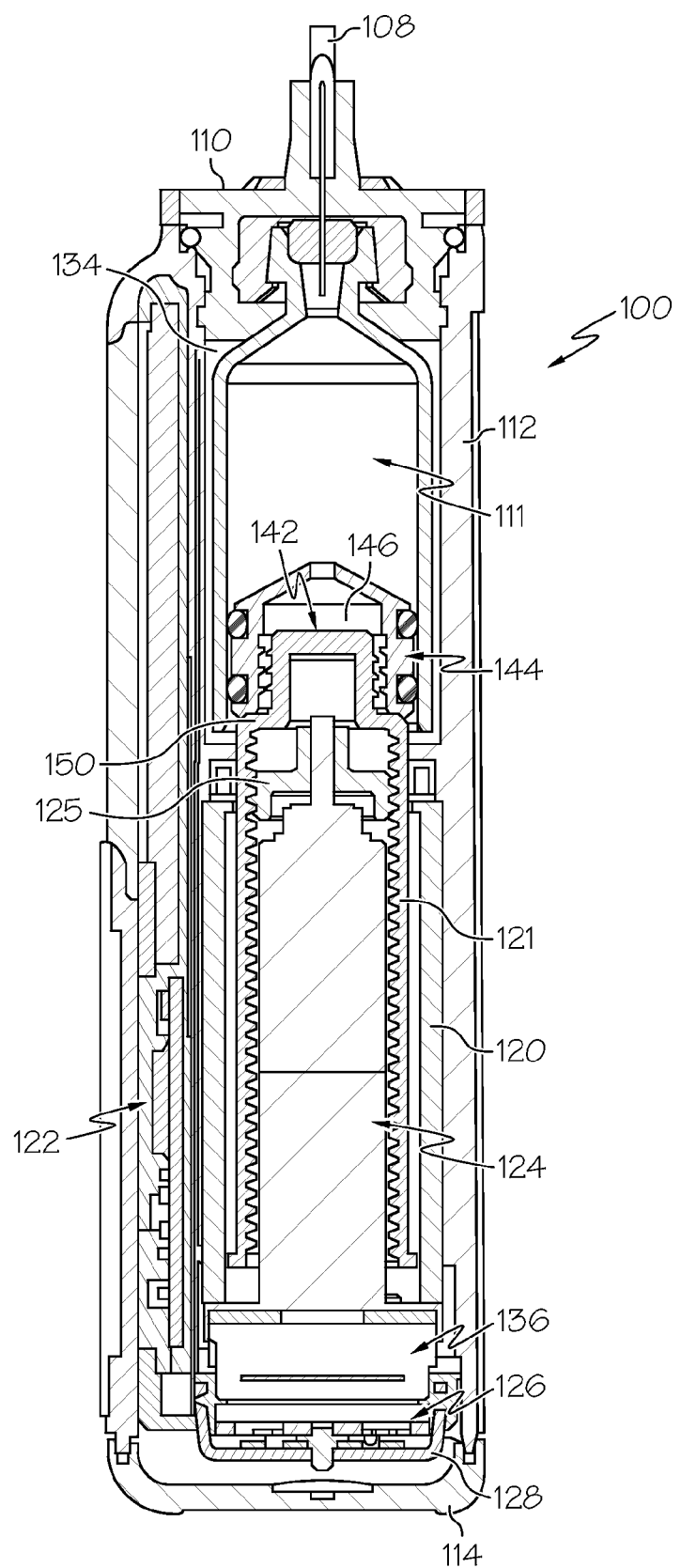
FIG. 3 is a cross sectional view of the fluid infusion device shown in FIG. 1, corresponding to a cross section taken longitudinally through the drive motor assembly and the fluid reservoir.

FIG. 3 is a cross sectional view of the fluid infusion device 100, corresponding to a cross section taken longitudinally through the drive motor assembly 124 and the fluid reservoir 111. FIG. 3 depicts the state of the fluid infusion device 100 after the fluid reservoir 111 has been inserted into the reservoir cavity 134 and after the fitting 110 has been secured to the housing 112 to hold the fluid reservoir 111 in place. While certain embodiments accommodate disposable, prefilled reservoirs, alternative embodiments may use refillable cartridges, syringes or the like. A cartridge can be prefilled with insulin (or other drug or fluid) and inserted into the housing 112. Alternatively, a cartridge could be filled by the user using an appropriate adapter and/or any suitable refilling device.

When assembled as shown in FIG. 3, the drive motor assembly 124 is located in the housing 112. The force sensor 126 is operatively associated with the drive motor assembly 124. For this particular embodiment, the force sensor 126 is coupled to the drive motor assembly 124, and it is located between a base end of the drive motor assembly 124 and the motor support cap 128. In one implementation, the force sensor 126 is affixed to the base end of the drive motor assembly 124 such that the force sensor 126 reacts when it bears against the motor support cap 128. In another implementation, the force sensor 126 is affixed to the housing end cap 114 such that the force sensor 126 reacts when the drive motor assembly 124 bears against the force sensor 126. This configuration and arrangement of the drive motor assembly 124 and the force sensor 126 allows the force sensor 126 to react to forces imparted thereto by the drive motor assembly 124 and/or forces imparted to the drive motor assembly 124 via the fluid pressure of the fluid reservoir 111.

The drive motor assembly 124 includes an electric motor 136 that is actuated and controlled by the electronics module of the fluid infusion device 100. The motor 136 is preferably realized as a stepper motor that rotates in a stepwise or discrete manner corresponding to the desired number of fluid delivery strokes. Alternatively, the motor 136 could be a DC motor, a solenoid, or the like. The motor 136 may optionally include an encoder (not shown), which cooperates with the electronics module of the fluid infusion device 100 to monitor the number of motor rotations or portions thereof. This in turn can be used to accurately determine the position of the slide 121, thus providing information relating to the amount of fluid dispensed from the fluid reservoir 111.

The drive motor assembly 124 can be mounted in the housing 112 using an appropriate mounting feature, structure, or element. Alternatively, the mounting could be accomplished using a shaft bearing and leaf spring or other known compliance mountings.

The illustrated embodiment of the drive motor assembly 124 includes a drive member (such as the externally threaded drive gear or drive screw 125) that engages an internally threaded second drive member (such as the slide 121) having a coupler 142. The coupler 142 may be attached to or integrated with the slide 121, as depicted in FIG. 2 and FIG. 3. The slide 121 is sized to fit within the housing of the fluid reservoir 111, which enables the slide 121 to operatively cooperate with the fluid reservoir 111. The fluid reservoir 111 includes a plunger or piston 144 with at least one sealing element or feature (e.g., one or more O-rings, integral raised ridges, or a washer) for forming a fluid and air tight seal with the inner wall of the fluid reservoir 111. As mentioned previously, the fluid reservoir 111 is secured into the housing 112 with the fitting 110, which also serves as the interface between the fluid reservoir 111 and the infusion set tubing 108. For this embodiment, the piston 144 is in contact with a linear actuation member, such as the slide 121. For example, the piston 144 may have a female portion 146 that receives the coupler 142 carried by the slide 121. The female portion 146 is positioned at the end face of the piston 144, and it is sized to receive and accommodate the coupler 142. In certain embodiments, the female portion 146 includes a threaded cavity that engages external threads of the coupler 142.

Referring to FIG. 3, rotation of the drive shaft of the motor 136 results in corresponding rotation of the drive screw 125, which in turn drives the slide 121 via the threaded engagement. Thus, rotation of the drive screw 125 results in axial displacement of the slide 121 and, therefore, axial displacement of the coupler 142. Such displacement of the coupler 142 moves the piston 144 (upward in FIG. 3) to deliver a predetermined or commanded amount of medication or liquid from the fluid infusion device 100. In this manner, the drive motor assembly 124 is configured to regulate delivery of fluid by actuating the piston 144 (under the control of the electronics module and/or control system of the fluid infusion device 100). As described above, if a stepper motor is employed, then the drive motor assembly 124 can regulate delivery of fluid from the fluid infusion device 100 in discrete actuation or delivery strokes. The fluid infusion device 100 can employ the sleeve 120 or an equivalent feature (such as an anti-rotation key) to inhibit rotation of the drive motor assembly 124, which might otherwise result from torque generated by the motor 136. In some embodiments, the drive shaft of the drive motor assembly 124, the drive screw 125, and the slide 121 are all coaxially centered within the longitudinal axis of travel of the piston 144. In certain alternative embodiments, one or more of these components may be offset from the center of the axis of travel and yet remain aligned with the axis of travel, which extends along the length of the fluid reservoir 111.

As mentioned above, certain embodiments of the fluid infusion device 100 accommodate removable and replaceable fluid reservoirs. When the slide 121 and, therefore, the piston 144 of the fluid reservoir 111 are in their fully extended positions, the piston 144 has forced most, if not all, of the fluid out of the fluid reservoir 111. After the piston 144 has reached the end of its travel path, indicating that the fluid reservoir 111 has been depleted, the fluid reservoir 111 may be removed such that the female portion 146 of the piston 144 disengages from the coupler 142 of the slide 121. After the empty (or otherwise used) fluid reservoir 111 is removed, the electronics module or control system of the fluid infusion device 100 initiates a rewind operation during which the motor 136 rotates in the reverse direction to rewind the slide 121 back to its fully retracted position. Thereafter, a new or refilled fluid reservoir 111 can be installed, seated, and primed for use. In this regard, an embodiment provides for advancement of the slide 121 upon the insertion of a fluid reservoir 111 into the housing 112. The slide 121 advances until its coupler 142 comes into contact with the piston 144 of the fluid reservoir 111. In alternative embodiments having a threaded piston engagement, the slide 121 advances until the threads of the coupler 142 engage the threads in the female portion 146 of the piston 144. When the threads engage in this fashion, they need not do so by twisting. Rather, they may ratchet over one another. In operation, the force sensor 126 may be used to determine when the slide 121 contacts the piston 144, when the coupler 142 is properly seated in the female portion 146, and/or when the fluid reservoir 111 has been primed and is ready to deliver measured doses of fluid.

Although the illustrated embodiment employs a coaxial or inline drive system, alternative configurations could be utilized. For example, a drive system that uses a lead screw, a drive nut, and actuation arms (of the type described in U.S. Pat. No. 6,485,465) may be employed, with the force sensor 126 positioned in an appropriate location. In various embodiments, the drive train might include one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. Moreover, although the illustrated embodiment employs a sensor positioned at the end of the fluid drive train, other arrangements could be deployed. For example, a sensor could be placed at or near the front end of the fluid drive train.

In particular embodiments, the force sensor 126 is used to detect when the slide 121 contacts the piston 144. Thus, after the fluid reservoir 111 is placed into the fluid infusion device 100, the motor 136 is activated to move the slide 121 toward the fluid reservoir 111 to engage the piston 144. In this regard, when a shoulder region 150 (see FIG. 3) of the slide 121 first contacts the piston 144, the electronics module detects an increase in force imparted to the force sensor 126. The measured force continues to increase as the motor 136 continues to drive forward, in response to the fluid resistance in the fluid reservoir 111. When the slide 121 is properly seated with the piston 144, the measured force increases to the seating threshold level. During the seating operation, if the measured force exceeds this seating threshold, the motor 136 is stopped until further commands are issued. The seating threshold is generally about 1.5 pounds. In alternative embodiments, higher or lower seating thresholds may be used depending on the force required to mate the slide 121 with the piston 144, the force required to urge fluid from the fluid reservoir 111, the speed of the motor 136, the accuracy and resolution of the force sensor 126, or the like.

It should be appreciated that other force thresholds can be used for other purposes. During priming of fluid reservoirs, for example, a threshold of about 4.0 pounds is used. In some embodiments, levels greater than about 5.0 pounds are used to detect shock loads that may be damaging to the fluid infusion device 100.

The force sensor 126 is configured to react in response to force imparted thereto. In this regard, electrical, mechanical, magnetic, and/or other measurable or detectable characteristics of the force sensor 126 vary in accordance with the amount of force applied to the force sensor 126. In practice, the force sensor 126 might implement or otherwise leverage known sensor technologies, such as the sensor technology described in U.S. Pat. No. 6,485,465. As shown in FIG. 2, the force sensor 126 includes at least one electrical lead 154 that is electrically coupled to the electronics module (or controller) of the fluid infusion device 100. Alternatively, the force sensor 126 could use wireless data communication technology to provide force-related data to the electronics module. In certain implementations, the force sensor 126 is suitably configured to indicate or generate a plurality of different output levels that can be monitored and/or determined by the electronics module. In practice, the output levels obtained from the force sensor 126 are initially conveyed as analog voltages or analog currents, and the electronics module includes an analog-to-digital converter that transforms a sampled analog voltage into a digital representation. Conversion of sensor voltage into the digital domain is desirable for ease of processing, comparison to threshold values, and the like.

In particular embodiments, the force sensor 126 is realized as an electromechanical component having at least one variable resistance that changes as the force applied to the force sensor 126 changes. In alternative embodiments, the force sensor 126 is a capacitive sensor, a piezoresistive sensor, a piezoelectric sensor, a magnetic sensor, an optical sensor, a potentiometer, a micro-machined sensor, a linear transducer, an encoder, a strain gauge, or the like, and the detectable parameter or characteristic might be compression, shear, tension, displacement, distance, rotation, torque, force, pressure, or the like. In practice, changing characteristics of the force sensor 126 are associated with output signal characteristics that are responsive to a physical parameter to be measured. Moreover, the range and resolution of the monitored output signal provides for the desired number of output levels (e.g., different states, values, quantities, signals, magnitudes, frequencies, steps, or the like) across the range of measurement. For example, the force sensor 126 might generate a low or zero value when the applied force is relatively low, a high or maximum value when the applied force is relatively high, and intermediate values when the applied force is within the detectable range.

In certain exemplary embodiments, the electronics module of the fluid infusion device 100 maintains a constant supply voltage across the force sensor 126, and the monitored output signal of the force sensor 126 is a signal current that passes through a resistive material of the force sensor 126. Thus, the signal current varies with the amount of force applied to the force sensor 126 because the resistance of the force sensor 126 varies with force and the supply voltage across the force sensor 126 is constant. The electronics module converts the monitored signal current into a signal voltage, which is then used as an indication of the force imparted to the force sensor 126 (which may be caused by the drive motor assembly 124, by fluid pressure in the fluid reservoir 111, by impact experienced by the fluid infusion device 100, etc.). In alternative embodiments, a constant supply current is used and the signal voltage across the force sensor 126 varies with force (fluid pressure).

In certain embodiments, sensor measurements are taken prior to commanding the drive system to deliver fluid, and soon after the drive system has stopped delivering fluid. In alternative embodiments, sensor data is collected on a continuous basis at a particular sampling rate (for example, 10.0 Hz, 3.0 Hz, once every 10 seconds, once a minute, once every five minutes, or the like). In further alternative embodiments, the sensor data is only collected prior to commanding the drive system to deliver fluid. In still further alternative embodiments, sensor data is collected during fluid delivery (during delivery strokes and/or between delivery strokes).

In practice, the force sensor 126 and associated electronics are designed to measure forces between about zero pounds and about five pounds with a desired resolution of about 0.01 pounds. In preferred embodiments, the force sensor 126 and associated electronics provide a relatively linear voltage output in response to forces applied to the force sensor 126 by one or more drive train components. In alternative embodiments, the range and resolution of the force sensor 126 might vary from that specified above. Furthermore, the sensor range and/or resolution may vary in accordance with the concentration of the fluid being delivered, the diameter of the fluid reservoir 111, the diameter of the fluid path, the nominal range of force experienced during normal operation of the drive motor assembly 124, the amount of sensor noise, the algorithms applied to detect trends from sensor measurements, or the like. Moreover, the fluid infusion device 100 and the force sensor 126 should be suitably configured to survive shock levels that result in much higher forces being applied to the force sensor 126 than the intended sensor measurement range.

Figure 4:
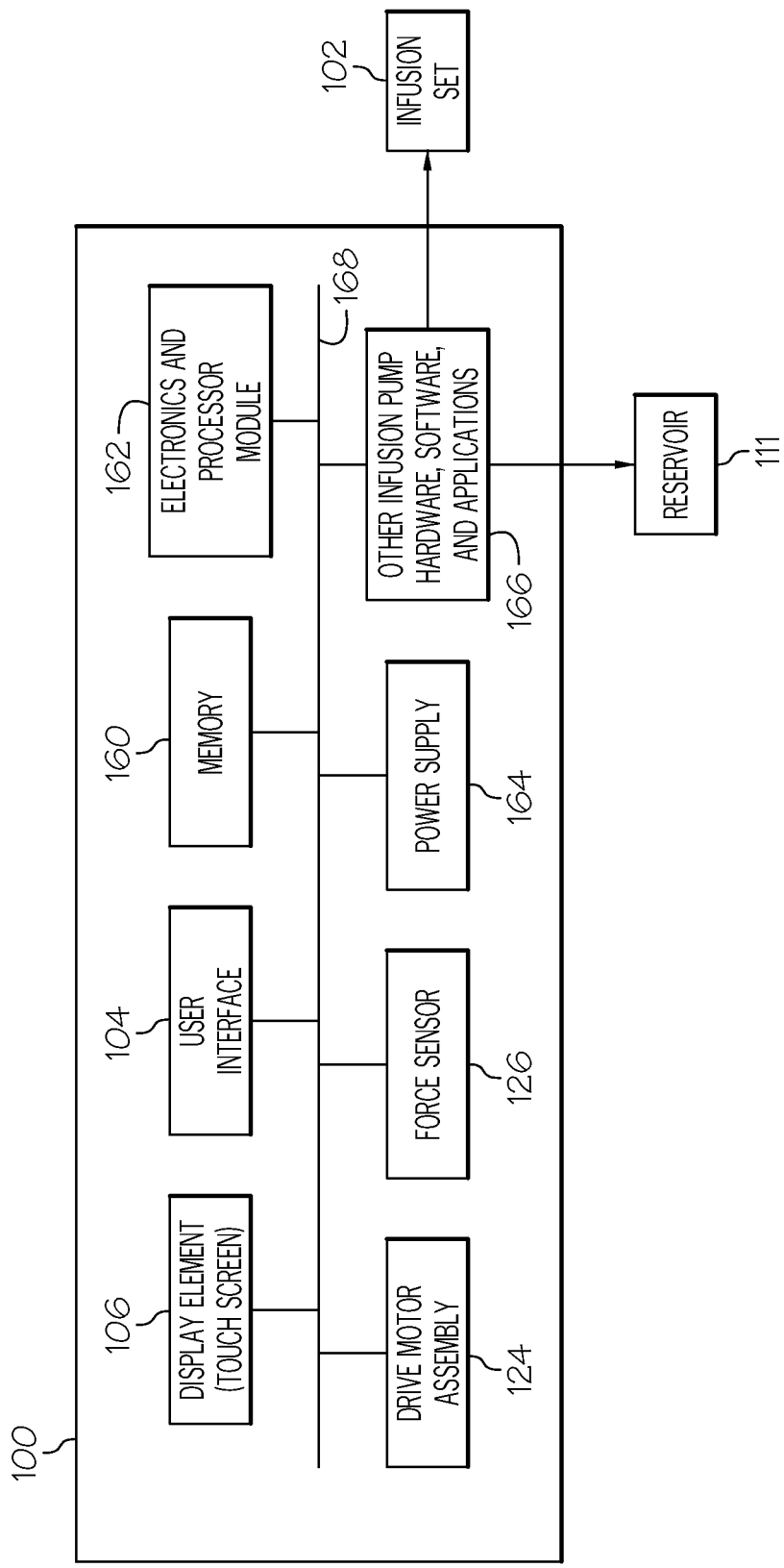
FIG. 4 is a schematic block diagram representation of an embodiment of a fluid infusion device.

As mentioned previously, the fluid infusion device 100 is suitably configured to support a number of techniques, processes, and methodologies that utilize the force sensor 126. In practice, the fluid infusion device 100 includes an electronics module, processing logic, software applications, and/or other features that are used to carry out the various operating processes described here. In this regard, FIG. 4 is a schematic block diagram representation of an embodiment of the fluid infusion device 100. FIG. 4 depicts some previously-described elements of the fluid infusion device 100 as functional blocks or modules, namely, the display element 106; the user interface 104; the drive motor assembly 124; and the force sensor 126. FIG. 4 also depicts the fluid reservoir 111 and the infusion set 102 in block format. This particular embodiment of the fluid infusion device 100 also includes, without limitation: a suitable amount of memory 160; an electronics module 162 (which may include or cooperate with one or more processors, processing modules, controllers, state machines, or the like); a power supply 164 such as a battery or a battery pack; and other infusion pump hardware, software, and applications 166. The elements of the fluid infusion device 100 may be coupled together via an interconnection architecture 168 or arrangement that facilitates transfer of data, commands, power, etc.

The display element 106 represents the primary graphical interface of the fluid infusion device 100. The display element 106 may leverage known plasma, liquid crystal display (LCD), thin film transistor (TFT), and/or other display technologies. The actual size, resolution, and operating specifications of the display element 106 can be selected to suit the needs of the particular application. Notably, the display element 106 may include or be realized as a touch screen display element that can accommodate touch screen techniques and technologies. In practice, the display element 106 may be driven by a suitable display driver to enable the fluid infusion device 100 to display physiological patient data, status information, clock information, alarms, alerts, and/or other information and data received or processed by the fluid infusion device 100.

The user interface 104 may include a variety of items such as, without limitation: a keypad, keys, buttons, a keyboard, switches, knobs (which may be rotary or push/rotary), a touchpad, a microphone suitably adapted to receive voice commands, a joystick, a pointing device, an alphanumeric character entry device or touch element, a trackball, a motion sensor, a lever, a slider bar, a virtual writing tablet, or any device, component, or function that enables the user to select options, input information, or otherwise control the operation of the fluid infusion device 100. In this context, the user interface 104 may cooperate with or include a touch screen display element 106. The user interface 104 allows a user to control the delivery of fluid via the infusion set 102.

The electronics module 162 may include or be implemented with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

The electronics module 162 may include one processor device or a plurality of cooperating processor devices. Moreover, a functional or logical module/component of the fluid infusion device 100 might be realized by, implemented with, and/or controlled by processing logic maintained by or included with the electronics module 162. For example, the display element 106, the user interface 104, the drive motor assembly 124, and/or the infusion pump hardware, software, and applications 166 (or portions thereof) may be implemented in or controlled by the electronics module 162.

The memory 160 may be realized as RAM memory, flash memory, EPROM memory, EEPROM memory, registers, a hard disk, a removable disk, a CD-ROM, or any other form of storage medium known in the art. In this regard, the memory 160 can be coupled to the electronics module 162 such that the electronics module 162 can read information from, and write information to, the memory 160. In the alternative, the memory 160 may be integral to the electronics module 162. As an example, a processor of the electronics module 162 and the memory 160 may reside in an ASIC. In practice, a functional or logical module/component of the fluid infusion device 100 might be realized using program code that is maintained in the memory 160. Moreover, the memory 160 can be used to store data utilized to support the operation of the fluid infusion device 100, including, without limitation, sensor data, force measurements, force thresholds, alert/alarm history, and the like (as will become apparent from the following description).

The infusion pump hardware, software, and applications 166 are utilized to carry out fluid infusion features, operations, and functionality. Thus, the infusion pump hardware, software, and applications 166 may include or cooperate with the infusion set 102 and/or the fluid reservoir 111 (as described above). It should be appreciated that the infusion pump hardware, software, and applications 166 may leverage known techniques to carry out conventional infusion pump functions and operations, and such known aspects will not be described in detail here.

A fluid infusion device can support one or more features or operations that enhance its fluid infusion functionality and/or enhance the user experience of the fluid infusion device. The following sections include descriptions of various processes and methods that may be performed by a fluid infusion device. The various tasks performed in connection with a given process may be performed by software, hardware, firmware, or any combination thereof. For illustrative purposes, a process might be described with reference to elements mentioned above in connection with FIGS. 1-4. In practice, portions of a given process may be performed by different elements of the described system, e.g., a sensor, a drive motor assembly, an electronics module, a processor, or the like. It should be appreciated that a described process may include any number of additional or alternative tasks, the tasks included in a particular flow chart need not be performed in the illustrated order, an embodiment of a described process may omit one or more of the illustrated tasks, and a given process may be incorporated into a more comprehensive procedure or process having additional functionality not described in detail herein.

Sensor Health Monitoring

For reasons presented above, the force sensor 126 in the fluid infusion device 100 is an important component that, at a minimum, is used to determine when a new fluid reservoir 111 is seated and when an occlusion has occurred. During use, the output and/or electromechanical characteristics of the force sensor 126 may drift over time. The drift can be attributed to the aging of mechanical components, impacts or shocks suffered by the fluid infusion device 100, environmental exposure, etc. It is desirable to monitor sensor drift so that the fluid infusion device 100 can alert the patient if the sensor drift exceeds a tolerable amount. Notably, the force sensor 126 cannot be easily or conveniently calibrated, for example on a yearly basis, because it is not accessible. Consequently, the force sensor 126 should not divert from a calibration curve (which contemplates typical variations or drifting of the force sensor 126) over the life of the product.

The sensor health monitoring features of the fluid infusion device 100 can be utilized to determine and monitor the drift characteristics of the force sensor 126. In accordance with one approach, it is assumed that the force sensor 126 experiences a consistent and relatively low load during rewind operations, which are performed before installing a new fluid reservoir 111. During a calibration routine (which may be performed, for example, during manufacturing of the fluid infusion device 100), the device records force data collected during one or more rewind stages. The force data is used to generate a nominal rewind force value, which may represent an average of the collected values, the maximum collected value, the minimum collected value, or the like. This rewind force value is saved in the memory 160 of the fluid infusion device 100. Thereafter, when deployed and operating, the fluid infusion device 100 performs a rewind force average check and compares the value to the saved rewind force. If the measured rewind force is within a specified range of the calibration rewind force value, then the fluid infusion device 100 continues to operate as usual. If, however, the measured rewind force drifts below a level that is not acceptable, then the fluid infusion device 100 can generate an alarm, an alert, or respond in a predetermined manner. The sensor health can be checked whenever a new fluid reservoir 111 is installed, typically every three days.

Figure 5:
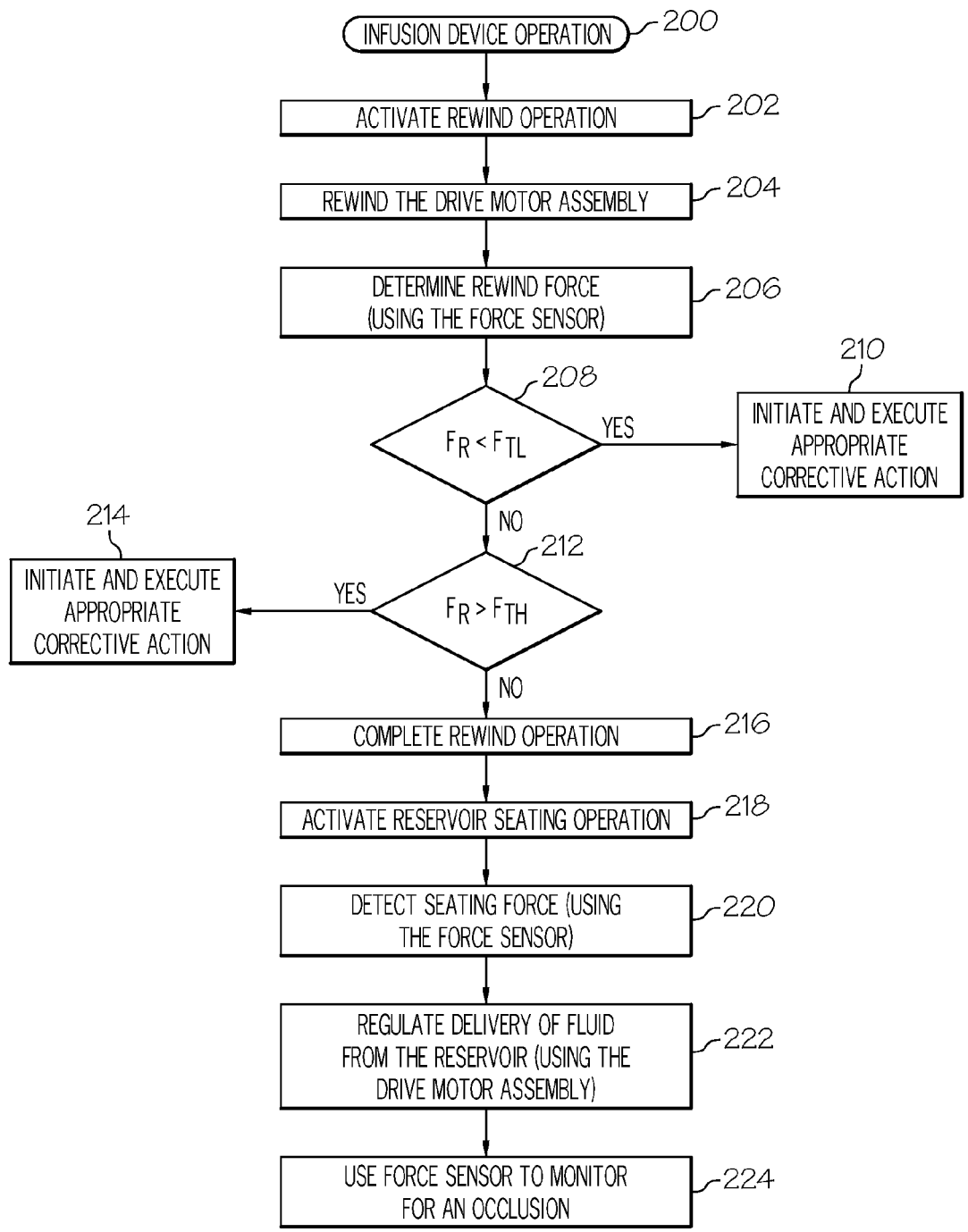
FIG. 5 is a flow chart that illustrates an embodiment of a process associated with the operation of a fluid infusion device.

FIG. 5 is a flow chart that illustrates an embodiment of a process 200 associated with the operation of a fluid infusion device, such as the fluid infusion device 100 described above. The process 200 may begin with the activation of a rewind operation of the drive motor assembly (task 202). As explained above, the drive motor assembly rewinds after removing an old fluid reservoir and before installing a new fluid reservoir. Accordingly, task 202 could be automatically performed whenever a fluid reservoir is removed from the fluid infusion device. As another option, task 202 could be performed (either automatically or initiated by the user) at other times when the fluid infusion device 100 is not delivering fluid. In this regard, the slide 121 can be retracted from the piston 144 while leaving the piston 144 in place. The position of the slide 121 prior to retraction can be stored such that the slide 121 can be precisely returned to its former position to continue delivering fluid. In response to the rewind activation, the process 200 rewinds the drive motor assembly by an appropriate amount (task 204). To accommodate installation of a new fluid reservoir, task 204 rewinds the drive motor assembly until the slide is fully retracted.

The absence of a fluid reservoir during the rewind operation results in no loading on the drive motor assembly. For this reason, the process 200 determines a rewind force imparted to the force sensor during the rewind operation (task 206). Task 206 could obtain a single rewind force measurement at any time during the rewind operation, it could calculate an average rewind force based upon any number of rewind force measurements obtained during the rewind operation, or it could generate any rewind force value or metric that is based upon one or more individual rewind force measurements obtained during the rewind operation. For simplicity, this particular embodiment of the process 200 assumes that a single rewind force measurement is determined at task 206.

The process 200 may continue by comparing the rewind force measurement to one or more threshold forces. For this example, the process 200 determines whether or not the rewind force measurement falls within a predetermined range, and initiates corrective action at the fluid infusion device when the rewind force measurement does not fall within that range. Thus, if the rewind force measurement is less than the lower threshold force (query task 208), then the fluid infusion device initiates and executes appropriate corrective action (task 210). Similarly, if the rewind force measurement is greater than the upper threshold force (query task 212), then the fluid infusion device initiates and executes appropriate corrective action (task 214). The corrective action taken by the fluid infusion device may include one or more of the following, without limitation: generating an alert or an alarm at the fluid infusion device; stopping or inhibiting fluid delivery; presenting instructions, a maintenance reminder, or a message to the user; or the like. In practice, an alert, alarm, or warning may include, without limitation: sounds; one or more synthesized voices; vibrations or other haptic feedback; displayed symbols or messages; lights; transmitted signals; Braille output; or the like. Other forms of corrective action include, without limitation: running a self test of the fluid infusion device; recalibrating the threshold forces; temporarily disabling the fluid infusion device; or the like.

A rewind force measurement that is less than the lower threshold force indicates that the measured force is less than the actual force applied to the force sensor. Consequently, it may be more difficult for the fluid infusion device to accurately and quickly detect the onset of an occlusion in the fluid path based on the force sensor output. On the other hand, a rewind force measurement that is greater than the upper threshold force indicates that the measured force is greater than the actual force applied to the force sensor. Consequently, the fluid infusion device might detect the onset of an occlusion too soon, or falsely detect an occlusion. Therefore, the type of corrective action taken at task 210 may be different than the type of corrective action taken at task 214. In this regard, different alert characteristics (colors, volume, frequency, sounds), different message content or formats, and/or different combinations of the corrective actions described above could be initiated and executed at tasks 210, 214.

It should be appreciated that the fluid infusion device processes the output levels associated with the force sensor to determine the current operating health of the force sensor. If the rewind force measurement falls within the specified range (i.e., it is greater than the lower threshold force and less than the upper threshold force), then the fluid infusion device can continue operating as usual. For example, the fluid infusion device can complete the rewind operation (task 216, which may be performed before or during tasks 206, 208, 210, 212, 214) before placement of a new fluid reservoir into the fluid infusion device. After the new fluid reservoir is installed, the process 200 activates a reservoir seating operation (task 218) and uses the force sensor to detect when the new fluid reservoir is seated in the fluid infusion device. In this regard, the drive motor assembly is activated to advance the slide until a predetermined seating force has been detected (task 220). After detection of this seating force, the drive motor assembly can be further advanced by an appropriate amount during a priming operation, which is activated to prepare the fluid infusion device and the new fluid reservoir for normal operation.

As mentioned above, a rewind operation and the related force measurements could be performed before the fluid reservoir needs to be replaced. If the process 200 determines that the force sensor is operating as expected during such a rewind operation, then task 218 and task 220 are performed to return the slide 121 to its former position in contact with the piston 144. Thereafter, fluid delivery may continue as though the rewind operation never took place.

During normal use, the fluid infusion device regulates the delivery of fluid from the fluid reservoir by controlling the movement of the drive motor assembly (task 222). The same force sensor used to determine the rewind force measurements can also be used to monitor for the onset of an occlusion (task 224). In particular, the force imparted to the force sensor (which is indicative of the pressure in the fluid reservoir) is determined and analyzed in accordance with one or more occlusion detection schemes to detect an occlusion of the infusion set or elsewhere in the fluid delivery path.

In certain embodiments, the measured rewind forces (see task 206) observed during operation are recorded in the memory of the device. The historical rewind force data may be used to detect trends and drifting in the measured rewind force, e.g., consistently decreasing, consistently increasing, random variation, or the like. Thus, even if a measured rewind force does not trigger corrective action, the rewind force values can be saved for diagnostic purposes, statistical evaluation of the device, and the like.

Figure 6:
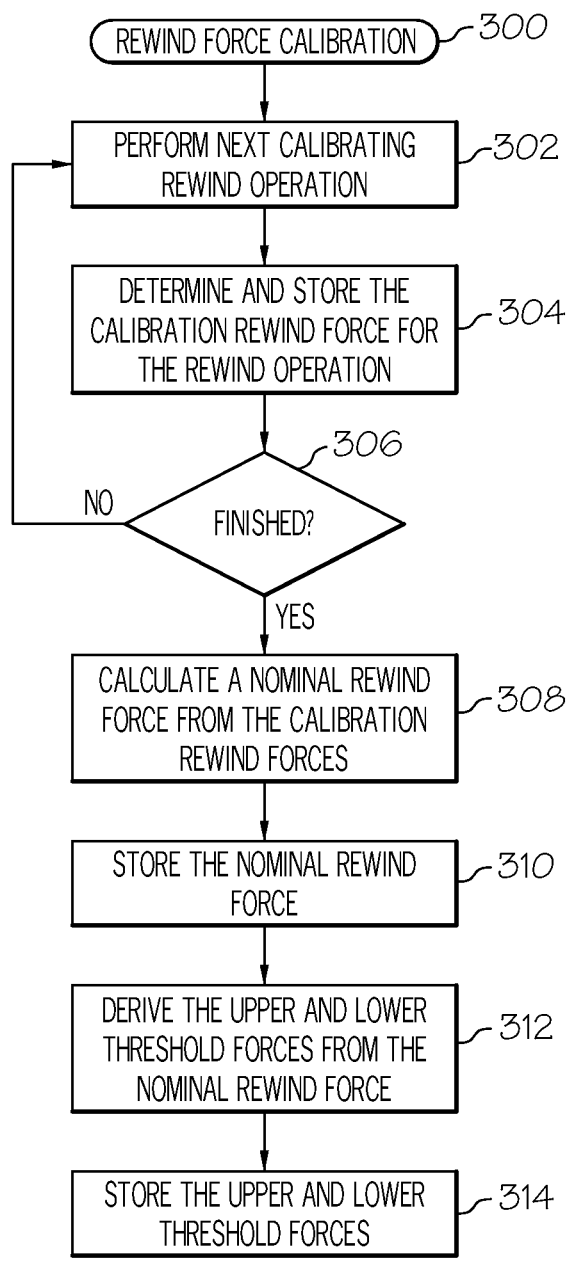
FIG. 6 is a flow chart that illustrates an embodiment of a rewind force calibration process for a fluid infusion device.

The preceding description of the process 200 illustrates how rewind force thresholds can be used to check the operating health of the force sensor. The threshold forces may be fixed or adaptive (to accommodate and compensate for drifting of the force sensor). In this regard, FIG. 6 is a flow chart that illustrates an embodiment of a rewind force calibration process 300 for a fluid infusion device, such as the fluid infusion device 100. In certain scenarios, the process 300 is performed at least once during manufacturing of the fluid infusion device, and the calibrated threshold forces are stored as fixed values for the life of the device. In other situations, the process 300 could be performed periodically (e.g., at the request of the user, every year, or in accordance with a maintenance schedule). The illustrated embodiment of the process 300 begins by performing a calibrating rewind operation (task 302). No fluid reservoir is present during calibration, and the drive motor assembly is controlled as necessary to execute a rewind operation.

During the calibrating rewind operation, the process 300 determines a calibration rewind force imparted to the force sensor (task 304). Task 304 could obtain a single rewind force measurement at any time during the calibrating rewind operation, it could calculate an average calibration rewind force based upon any number of rewind force measurements obtained during the calibrating rewind operation, or it could generate any calibration rewind force value or metric that is based upon one or more individual calibration rewind force measurements obtained during the calibrating rewind operation. For simplicity, this particular embodiment of the process 300 assumes that a single calibration rewind force measurement is determined at task 304. If the calibration period is finished (query task 306), then the process 300 continues. If not, the process 300 performs another calibrating rewind operation and determines a respective calibration rewind force measurement for that operation. In other words, tasks 302, 304, 306 can be repeated any desired number of times, resulting in a plurality of calibration rewind forces that can be saved for subsequent analysis and processing.

Upon completion of the calibration period, the process 300 calculates a nominal rewind force from the plurality of calibration rewind forces (task 308). The nominal rewind force can be determined using any desired formula, algorithm, relationship, or equation. For the simple implementation described here, the nominal rewind force is calculated as an average of the plurality of calibration rewind forces. As mentioned previously, the nominal rewind force is ideally equal or equivalent to a load of zero pounds on the drive motor assembly. Accordingly, an acceptable nominal rewind force will typically be within the range of about −0.50 to +0.50 pounds (this range is merely exemplary, and an embodiment could utilize different upper and/or lower values). In this regard, the process 300 might check the calculated nominal rewind force to ensure that it falls within a predetermined range of acceptable values. Thus, if the nominal rewind force falls outside of that range, the process 300 could generate an alarm, an alert, or a warning for the user, and/or repeat the portion of the calibration routine associated with tasks 302, 304, 306, and 308.

Assuming that the calculated nominal rewind force is acceptable, it can be stored in a memory element of the fluid infusion device (task 310) for future reference if needed. For this particular embodiment, the process 300 derives the lower threshold rewind force and the upper threshold rewind force from the calculated nominal rewind force (task 312). For example, the lower threshold force might be calculated by subtracting a designated amount from the nominal rewind force, and the upper threshold force might be calculated by adding a designated amount to the nominal rewind force. Moreover, the manner in which these threshold forces are calculated could vary as a function of the nominal rewind force itself. For instance, one threshold calculation scheme could be used when the nominal rewind force is greater than zero, and a different threshold calculation scheme could be used when the nominal rewind force is less than zero. After the rewind force thresholds have been derived, they can be stored in a memory element of the fluid infusion device (task 314) for subsequent use as needed, e.g., during execution of the process 200. In practice, these rewind force thresholds can be saved as fixed values that do not change during the operating life of the fluid infusion device. In this manner, the process 300 results in a specified range of rewind forces that is indicative of a healthy operating status of the force sensor.

In accordance with another approach, the operating health of the force sensor 126 is checked more frequently, namely, at times other than during a rewind operation. This alternate approach (which may be utilized in conjunction with the first approach described above) checks the health of the force sensor in an ongoing manner without having to wait until a rewind operation. More particularly, this technique checks the measured or detected force associated with the drive motor assembly at designated motor pulses (e.g., at every motor pulse). If the measured force is below a predetermined value, the fluid infusion device will take corrective action because this condition indicates that the force sensor has drifted beyond its limit in the negative direction. If the measured force is above a predetermined value, then the fluid infusion device assumes that the force sensor has drifted in the positive direction, which might result in false or early detection of an occlusion.

Figure 7:
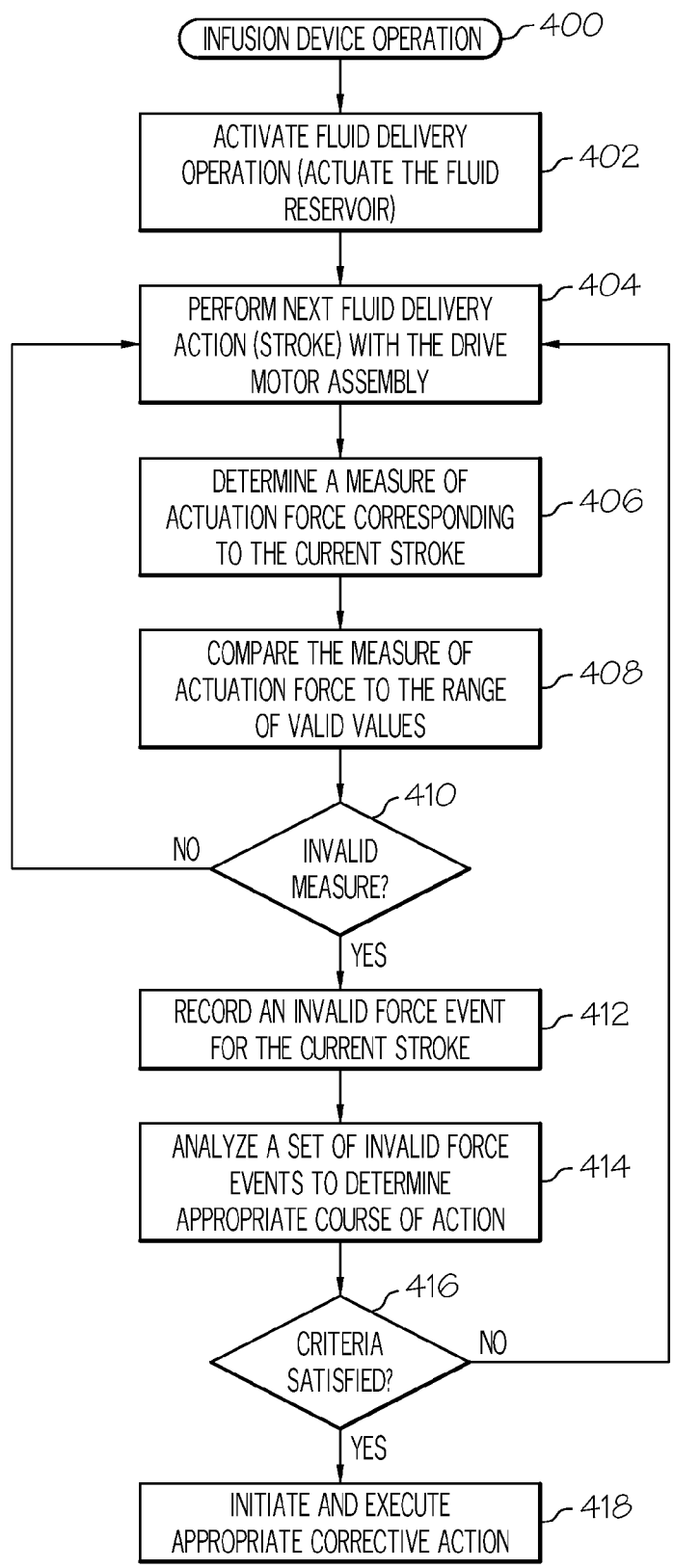
FIG. 7 is a flow chart that illustrates another embodiment of a process associated with the operation of a fluid infusion device.

FIG. 7 is a flow chart that illustrates another embodiment of a process 400 associated with the operation of a fluid infusion device, such as the fluid infusion device 100 described above. The process 400 may begin any time after activating a fluid delivery operation of the fluid infusion device (task 402). During a fluid delivery operation, the drive motor assembly is used to actuate the fluid reservoir in a controlled manner. In certain implementations, fluid delivery operations are carried out in a stepwise manner such that fluid is administered in discrete fluid delivery strokes (or pulses) of the slide. In practice, a fluid delivery operation may involve multiple fluid delivery strokes; the exact number will depend on the desired amount of fluid to be delivered. Accordingly, the process 400 continues by performing the next fluid delivery action, pulse, or stroke with the drive motor assembly (task 404), and determining and saving the corresponding measure of actuation force imparted to the force sensor during that fluid delivery action (task 406).

Next, the process 400 compares the measure of actuation force to a range of valid values for the fluid infusion device (task 408). In practice, there will be a range of force sensor outputs or readings that correspond to or otherwise represent normally expected measures of actuation forces. For example, if the force sensor is operating as expected, then it might have a limited and predetermined analog output range, which in turn corresponds to a limited and predetermined range of encoded digital values. If, however, the force sensor is damaged, is beginning to fail, or is otherwise operating in an unexpected or unusual manner, then the resulting analog output and encoded digital values could be outside of the normally expected range. Measured values of actuation force that are outside of the normally expected range are therefore treated as invalid or undefined measures.

If the current measure of actuation force is not invalid as defined by the particular settings and configuration of the fluid infusion device (query task 410), then the process 400 may return to task 404 to perform the next fluid delivery action. This enables the fluid infusion device to monitor the operating integrity of the force sensor during fluid delivery and in an ongoing and dynamic manner. If, however, the current measure of actuation force is outside the range of valid values, then the process may generate a flag or otherwise record an invalid force event for the current measure of actuation force (task 412). The recorded event may include information such as, for example, the delivery time of the current stroke, the current measure of actuation force, the current position of the slide or drive motor, or the like. Data associated with the recorded event can be saved for subsequent analysis, for reporting purposes, for troubleshooting or diagnostic purposes, etc. For instance, this embodiment of the process 400 continues by analyzing a set of invalid force events to determine a course of action for the fluid infusion device (task 414). In this regard, the set of invalid force events may represent a designated number of past invalid force events, including the current invalid force event, collected over a particular period of time, collected for a designated number of delivery strokes, or the like. In certain situations, the set of invalid force events may correspond to only one event, which could be sufficient to trigger an alarm or an alert if deemed necessary. This allows the process 400 to initiate corrective action based on a single actuation stroke or pulse, based on an average measure of multiple pulses, based on detected patterns of measured forces, or the like. Task 414 may be performed to reduce the likelihood of false alerts or false alarms associated with the operating health of the force sensor. In this regard, the process 400 may be used to detect a positive drift and/or a negative drift in the force sensor, which may result in the lack of timely alerts. Thus, the detection of only one invalid force event during an extended period of time or over the course of many delivery strokes can be disregarded without triggering an alert.

The process 400 could utilize any type of criteria that influences whether or not a single invalid force event or a set of invalid force events will cause the fluid infusion device to respond. For example, the criteria may dictate that at least a threshold number of invalid force events corresponding to consecutive fluid delivery actions must be recorded before a user alert is generated. As another example, the criteria may dictate that at least a threshold number of invalid force events must be recorded within a designated period of time (such as 60 minutes) before any corrective action is taken. The criteria may be chosen such that transient conditions that might influence the operation of the force sensor (e.g., handling of the device, bumping or dropping the device, driving over a pothole, etc.) do not trigger an alarm. Rather, the criteria may be selected such that the fluid infusion device is given the opportunity to recover and settle from such transient events.

Accordingly, if certain designated criteria is satisfied (query task 416), then the process 400 can initiate and execute appropriate corrective action at the fluid infusion device (task 418). If the criteria has not been satisfied, then the process 400 may return to task 404 to perform the next fluid delivery action. Thus, some form of corrective or remedial action can be taken in response to the recording of one or more invalid force events, where the recorded events are indicative of poor operating health of the force sensor. Task 418 may initiate and execute any of the corrective actions described above for tasks 210 and 214 of the process 200.

The process 400 represents a simplified embodiment that analyzes actuation forces and checks for valid measures of actuation force from one delivery stroke or pulse of the drive motor assembly to another. Alternative embodiments, however, could implement a more complex scheme that calculates and considers any suitable parameter, measure of force, force-related metric, or the like. For example, rather than compare the actuation forces to a range of valid measures per se, the fluid infusion device could instead calculate any appropriate parameter from the measured actuation force, where the parameter is somehow indicative of the operating health of the force sensor, and then compare the value of that parameter to certain predetermined performance criterion for the force sensor. If the parameter does not satisfy the performance criterion, then the fluid infusion device can take corrective or remedial action.

In some embodiments, the fluid infusion device 100 is suitably configured to check the operating condition of the force sensor 126 using a known and calibrated force applied to the force sensor 126. Although not always required, this example assumes that the force sensor 126 is tested after removing the fluid reservoir 111 and during a time when fluid need not be dispensed. Imparting a known nonzero calibration force to the force sensor 126 can be accomplished using any suitable component, device, fixture, or equipment. In accordance with one exemplary embodiment, the fitting 110 is replaced with a calibration fitting that is provided with a precisely calibrated spring or other element that provides a known force at a specified amount of deflection. After installing the calibration fitting, the slide 121 is advanced by a designated amount, which can be controlled by monitoring encoder counts or other metrics related to the operation of the drive motor 136. When the slide 121 has advanced by the designated amount, the force element (e.g., the spring) is expected to impart the calibrating force to the slide 121, which in turn imparts the calibrating force to the force sensor 126.

When the slide 121 has reached the calibration position, the corresponding measure of actuation force is recorded and compared to a value associated with the expected calibrating force. If the recorded value is different than the expected calibration value by more than a stated amount, then the fluid infusion device 100 (and/or the user) can assume that the force sensor 126 is defective or otherwise not functioning according to specification. It should be appreciated that the calibration force should fall within the normal measuring range of the force sensor 126.

Reservoir Seating (Presence) Monitoring

The force sensor 126 in the fluid infusion device 100 may also be utilized to monitor the presence and seating status of the fluid reservoir 111. In this regard, the electronics module 162 of the fluid infusion device 100 can be utilized to process the output levels of the force sensor 126 to determine the seating status of the fluid reservoir 111 in the reservoir cavity 134 in an ongoing manner. The fluid infusion device 100 can alert the user when the fluid reservoir 111 has been accidentally removed or inadvertently dislodged. The fitting 110 might be inadvertently rotated or loosened during physical activity (e.g., while the user is playing a sport or exercising), which in turn might result in removal or dislodging of the fluid reservoir 111. When this happens, proper coupling between the piston 144 of the fluid reservoir 111 and the coupler 142 of the slide 121 could be lost. For safe measure, the fluid infusion device 100 notifies the user shortly after the fluid reservoir 111 is partially removed, completely removed, or dislodged by more than a predetermined amount.

The fluid infusion device 100 uses the force sensor 126 to determine the seating status of the fluid reservoir 111. Accordingly, no additional components, sensors, or assembly time is needed to implement this feature. In certain embodiments, the fluid infusion device 100 uses a scheme that adaptively tracks the forces of delivery strokes. The fluid infusion device 100 records the force of a delivery stroke. If the measured force remains the same or increases from stroke-to-stroke, then the fluid infusion device 100 assumes that a fluid reservoir is in place and is properly seated. Moreover, slight variations in the detected force can be disregarded to contemplate normal and expected force variations that typically occur along the travel path of a fluid reservoir. However, a characterized drop in force that is greater than a certain amount indicates that (1) the fluid reservoir 111 has been removed or dislodged or (2) the fluid infusion device 100 may have been dropped or bumped, temporarily disturbing the force sensor 126. For the second scenario, design engineers can characterize how many pulses (delivery strokes) and/or how much time is typically needed to allow the fluid infusion device 100 to recover from a disturbing impact or force, assuming that the fluid reservoir 111 remains present and properly seated. If the measured force does not return to a nominal value after a designated number of strokes or a predetermined amount of time, the fluid infusion device 100 can conclude that the fluid reservoir 111 has been removed or disturbed and, in turn, generate an alert or a warning message for the user.

Notably, the reservoir presence scheme is adaptive in nature, and it takes into account variations such as sensor drift, reservoir frictional force variation, and minor shocks. The reservoir presence methodology actively monitors for an ongoing drop in force greater than a set value. This approach is desirable because it accommodates variations (such as sensor drift) that might be introduced over the life of the fluid infusion device 100, variations from one reservoir to another, and variations (such as fluid pressure) that might occur during use of a single reservoir. For example, if frictional force increases due to reservoir dynamics, the fluid infusion device 100 will adapt and set the increased force measure as a new baseline value. Similarly, if the frictional force is decreasing due to reservoir dynamics, the fluid infusion device 100 will adapt the lower force measure as the new baseline value (as long as the rate of decrease and/or the force variation is less than a specified amount). This feature accommodates variation in frictional force without false alarms. Accordingly, the fluid infusion device 100 adaptively resets the baseline force value as long as the rates of change are within normal limits.

Figure 8:
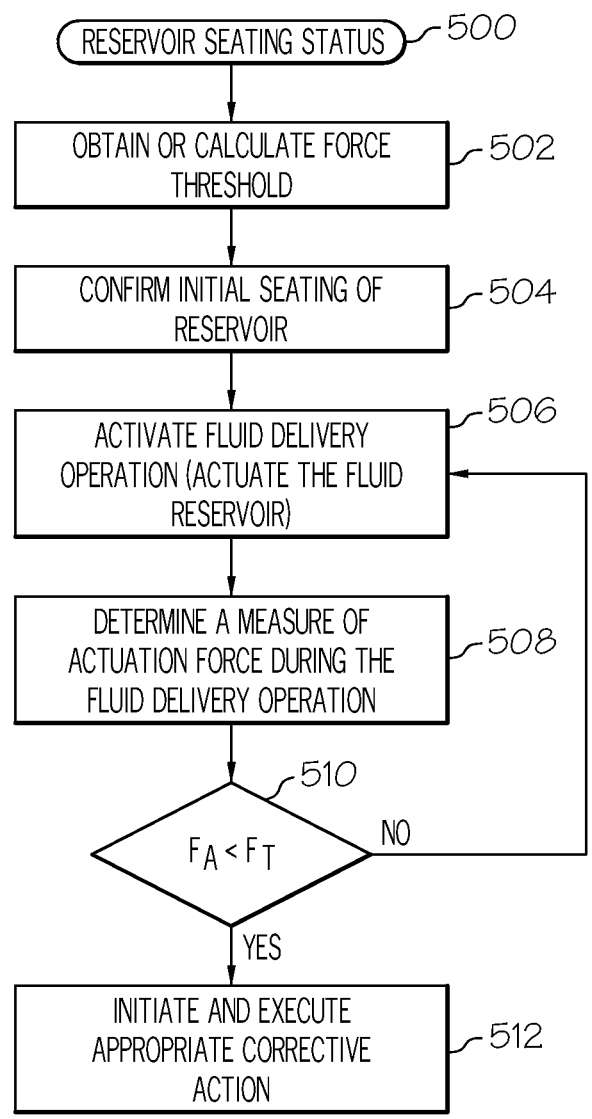
FIG. 8 is a flow chart that illustrates an embodiment of a process that checks the seating status of a fluid reservoir of a fluid infusion device.

FIG. 8 is a flow chart that illustrates an embodiment of a process 500 that checks the seating status of a fluid reservoir of a fluid infusion device, such as the fluid infusion device 100 described above. The process 500 employs a simple force threshold for purposes of determining the seating status of the fluid reservoir. In this regard, the process 500 may begin by obtaining, calculating, or accessing the force threshold (task 502), which represents an amount of force that is indicative of a dislodged, removed, displaced, or otherwise unseated state of the fluid reservoir. The force threshold may be adaptively updated in response to certain operating conditions, it may be one of a plurality of different available threshold values, it may be a predetermined and fixed value, or the like. For this example, the force threshold is a pre-stored value that is fixed during the operating lifespan of the fluid infusion device. In other embodiments (described below), the force threshold can be calculated in a dynamic manner to contemplate typical variations such as drifting of the force sensor.

Under typical operating conditions for exemplary embodiments, the normally expected force imparted to the force sensor when the fluid reservoir is properly seated is less than about 1.5 pounds. Moreover, under typical operating conditions for exemplary embodiments, the normally expected actuation force imparted to the force sensor during a fluid delivery stroke is less than about 1.5 pounds. In certain implementations, the force threshold used by the process 500 is calculated as a function of the nominal seating force and/or as a function of the nominal actuation force, and the force threshold is stored in a memory element of the fluid infusion device. For example, the force threshold might be calculated to be less than the average fluid delivery actuation force by a given amount, such as a percentage of the average fluid delivery actuation force. As another example, the force threshold is calculated such that it is a predefined amount of force less than the nominal expected actuation force. In practice, regardless of the manner in which it is calculated, the force threshold will typically be less than about 0.5 pounds.

In practice, the process 500 can be initiated whenever a fluid reservoir is installed into the fluid infusion device. Accordingly, the process 500 may confirm the initial seating of the fluid reservoir in the reservoir cavity (task 504). Task 504 may additionally (or alternatively) confirm when the fluid infusion device has performed a priming operation, which typically occurs after installation of a fluid reservoir. After confirming that the fluid reservoir has been properly seated and/or otherwise properly installed, the fluid infusion device will eventually activate a fluid delivery operation, which in turn actuates the fluid reservoir with the drive motor assembly (task 506). As described in more detail above, actuation of the fluid reservoir causes an amount of force to be imparted to the force sensor. Accordingly, the process 500 determines a measure of actuation force imparted to the force sensor during the fluid delivery operation (task 508). Task 508 could obtain a single actuation force measurement at any time during the fluid delivery operation, it could calculate an average actuation force based upon any number of actuation force measurements obtained during the fluid delivery operation (e.g., a plurality of actuation forces corresponding to a plurality of consecutive delivery strokes), or it could generate any actuation force value or metric that is based upon one or more individual actuation force measurements obtained during the fluid delivery operation. For simplicity, this particular embodiment of the process 500 assumes that a single actuation force measurement is determined at task 508. For this example, task 508 determines the measure of actuation force during the fluid delivery stroke itself. Alternatively (or additionally), task 508 could determine the measure of actuation force between fluid delivery strokes, and/or after a final fluid delivery stroke.

The process 500 may continue by comparing the actuation force measurement to one or more threshold forces. For this example, the process 500 compares the measure of actuation force to an amount of force (i.e., the force threshold obtained at task 502) that is less than the normally expected actuation forces of the fluid infusion device. Accordingly, the process 500 checks whether or not the measure of actuation force ($F_A$) is less than the force threshold ($F_T$) at query task 510. If the measure of actuation force is not less than the force threshold, then the process 500 assumes that the fluid reservoir is still in place and remains properly seated. Accordingly, the process 500 returns to task 506 to continue monitoring actuation force for the current fluid delivery operation (and for subsequent fluid delivery operations). If, however, query task 510 determines that the measure of actuation force is less than the force threshold and, therefore, that the measure of actuation force is indicative of an unseated state, then the fluid infusion device initiates and executes appropriate corrective action (task 512). The corrective action taken by the fluid infusion device may include, without limitation, one or more of the actions described above for the process 200 (see FIG. 5). It should be appreciated that the process 500 may consider any number of events (i.e., determinations that the measure of actuation force is less than the force threshold) and analyze a set of events to determine whether or not to initiate the corrective action. In this regard, the process 500 may determine whether a set of events satisfies certain predetermined criteria before taking corrective action, as described above with reference to tasks 412, 414, and 416 of the process 400.

Figure 9:
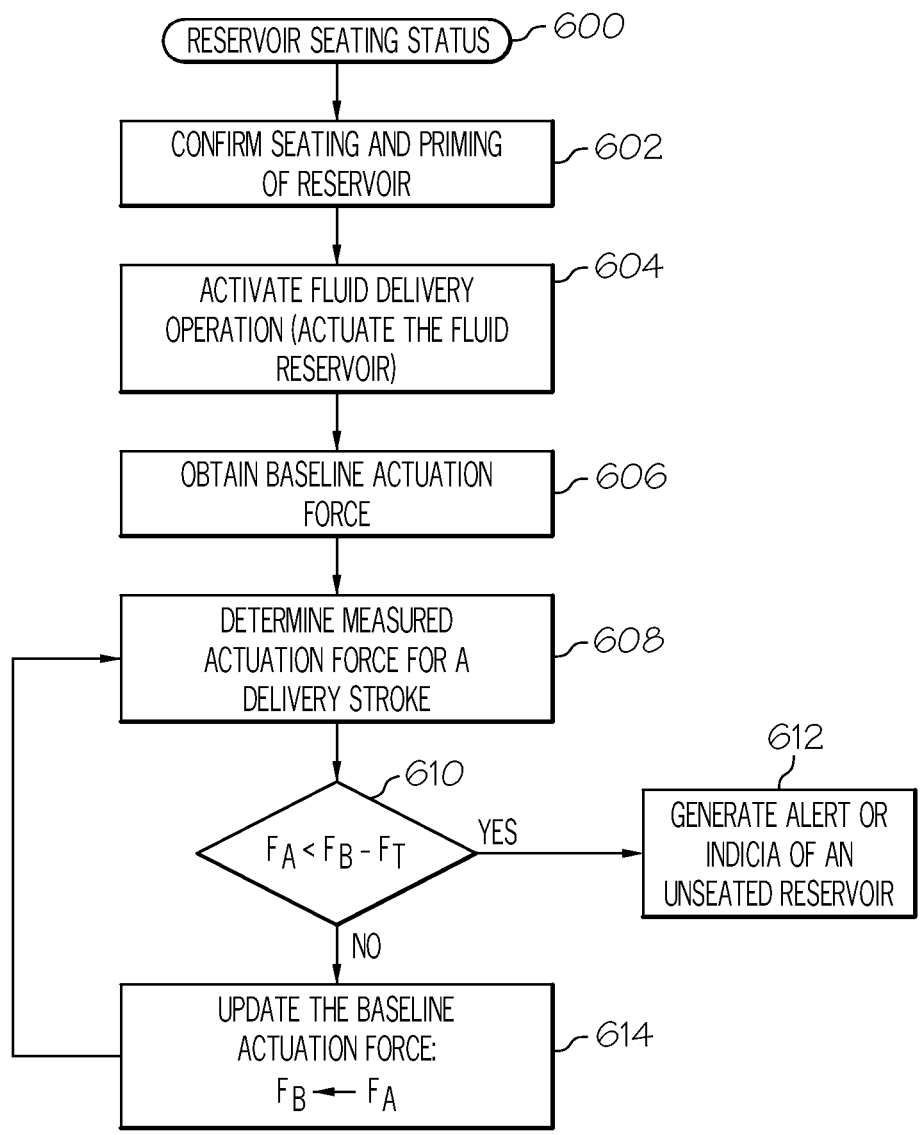
FIG. 9 is a flow chart that illustrates another embodiment of a process that checks the seating status of a fluid reservoir of a fluid infusion device.

The process 500 is one exemplary embodiment that utilizes a fixed force threshold value to determine whether or not the fluid reservoir is seated. In contrast, FIG. 9 is a flow chart that illustrates another embodiment of a process 600 that employs an adaptive scheme for checking the seating status of the fluid reservoir. The process 600 can be performed whenever a fluid reservoir is installed into the fluid infusion device. Thus, the process 600 may begin by confirming the initial seating and priming of the fluid reservoir (task 602), and activating a fluid delivery operation (task 604), as described above for the process 500. After initial seating of the fluid reservoir, the process obtains a baseline actuation force imparted to the force sensor (task 606). The baseline actuation force may correspond to a measure of actuation force that is obtained during the priming operation or shortly thereafter, or it may correspond to a measure of actuation force that is obtained during the first fluid delivery operation for a new fluid reservoir. The process 600 assumes that the baseline actuation force is measured while the fluid reservoir is properly seated. Accordingly, the baseline actuation force can be stored in a memory element of the fluid infusion device for later use.

Eventually, the process 600 determines a measured actuation force imparted to the force sensor, where the measured actuation force corresponds to a designated delivery stroke of the drive motor assembly (task 608). Task 608 could obtain a single actuation force measurement at any time during the fluid delivery operation, it could calculate an average actuation force based upon any number of actuation force measurements obtained during the fluid delivery operation (e.g., a plurality of actuation forces corresponding to a plurality of consecutive delivery strokes), or it could generate any actuation force value or metric that is based upon one or more individual actuation force measurements obtained during the fluid delivery operation. For simplicity, this particular embodiment of the process 600 assumes that a single actuation force measurement is determined at task 608. As mentioned previously, the actuation force could be determined during the fluid delivery stroke itself, between fluid delivery strokes, or after a final fluid delivery stroke.

The process 600 may continue by comparing the actuation force measurement to a measure of force that is influenced by the baseline actuation force ($F_B$). For this example, the process 600 checks (query task 610) whether the measured actuation force ($F_A$) is less than the baseline actuation force by some predetermined amount ($F_T$), which may be a fixed, adaptive, or dynamic threshold, as explained above for the process 500. In other words, query task 610 determines whether $F_A < F_B - F_T$. If query task 610 determines that the measure of actuation force is indicative of an unseated or dislodged fluid reservoir, then the fluid infusion device initiates and executes appropriate corrective action (task 612), e.g., generates an alert or some indicia of an unseated fluid reservoir. Alternatively or additionally, the corrective action taken by the fluid infusion device may include, without limitation, one or more of the actions described above for the process 200 (see FIG. 5). It should be appreciated that the process 600 may consider any number of events (i.e., individual determinations that $F_A < F_B - F_T$) and analyze a set of events to determine whether or not to initiate the corrective action. In this regard, the process 600 may determine whether a set of events satisfies certain predetermined criteria before performing task 612 (see the above description of tasks 412, 414, and 416 of the process 400).

If the measure of actuation force is indicative of a properly seated fluid reservoir, then the process 600 updates the baseline actuation force as a function of the measured actuation force (task 614). For this particular embodiment, task 614 updates the baseline actuation force by saving the measured actuation force for use as the next baseline actuation force. In practice, the fluid infusion device could implement a maximum and/or a minimum allowable baseline actuation force to ensure that the process 600 maintains a realistic baseline value. If for some reason the measured actuation force falls outside of the stated range of baseline force values, the fluid infusion device could generate an alert or take appropriate action. In this regard, a maximum or minimum value could serve as a confirmation or check of the operating health of the force sensor (see the Sensor Health Monitoring section of this description). Referring back to task 614, after updating the baseline actuation force, the process 600 returns to task 708 to continue monitoring actuation force for the current fluid delivery operation (and for subsequent fluid delivery operations). Thus, the baseline actuation force is adjusted and updated in an ongoing manner while the process 600 monitors the seating status of the fluid reservoir. This adaptive approach enables the process 600 to consider and compensate for slight variations in measured actuation forces.

Figure 10:
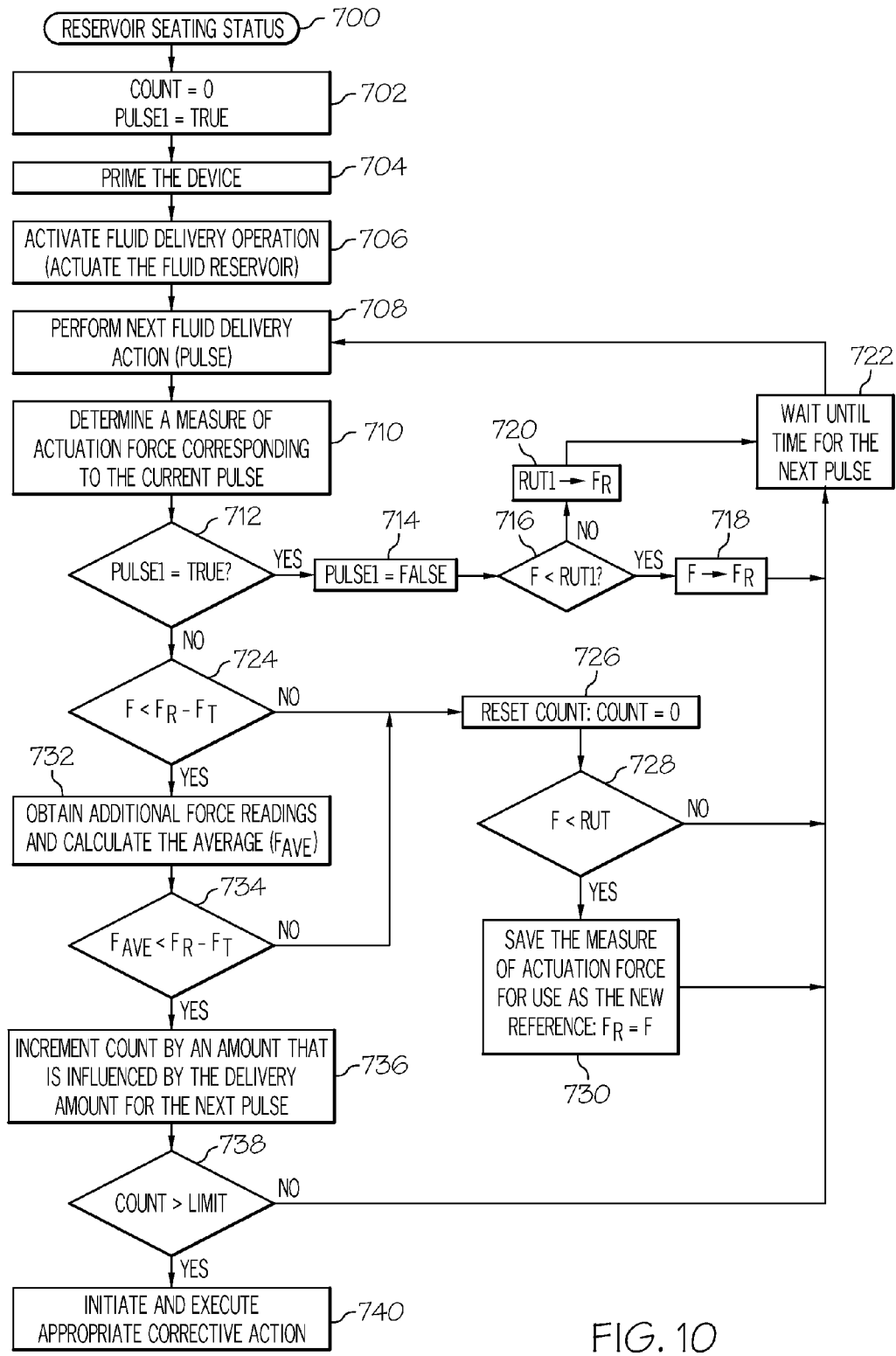
FIG. 10 is a flow chart that illustrates yet another embodiment of a process that checks the seating status of a fluid reservoir of a fluid infusion device.

FIG. 10 is a flow chart that illustrates yet another embodiment of a process 700 that checks the seating status of a fluid reservoir. The process 700 uses a threshold force value that corresponds to the maximum expected variation in actuation force for the fluid reservoir. This threshold force value may be empirically determined, calculated based on known operating parameters of the fluid infusion device, or generated and dynamically updated during operation of the fluid infusion device. In certain embodiments, the threshold force value is determined and stored as a fixed value during the operating lifespan of the fluid infusion device. For example, and without limitation, the typical fluid delivery force for a fluid reservoir might be about 1.4 pounds between initial piston seating and depletion of the fluid reservoir, and the threshold force value might be about 0.2 pounds.

The process 700 obtains the measures of actuation force imparted to the force sensor for consecutive fluid delivery pulses (in practice, a measure of actuation force is recorded for each fluid delivery pulse). The process 700 calculates a pulse-to-pulse difference between consecutive fluid delivery pulses, where the pulse-to-pulse difference is based on respective measures of actuation force for the consecutive fluid delivery pulses. If the pulse-to-pulse difference is greater than the designated threshold force value, then the fluid infusion device initiates corrective action in some manner. In other words, if the difference in actuation force between the last fluid delivery pulse and the current fluid delivery pulse is more than the normally expected force variation, then the fluid infusion device assumes that the detected condition is indicative of a dislodged or removed fluid reservoir, or a transient state caused by an impact or sudden acceleration to the fluid infusion device. Note that in order to assume a removed or dislodged reservoir, the difference in force from one pulse to the next must be negative, i.e., the measured force has decreased rather than increased.

The process 700 may include some tasks that are similar or identical to counterpart tasks found in the process 600, and such tasks will not be redundantly described here. The process 700 assumes that the fluid reservoir has already been properly seated for fluid delivery. This embodiment of the process 700 begins by initializing and maintaining a count (task 702) that is indicative of the seating status of the fluid reservoir. The count may be initialized at any suitable value, although this example assumes that the count is initialized at a value of zero. The process 700 also sets the value of PULSE1 to "True" (task 702). The value of PULSE1 is True only for the first actuation pulse following installation of a fluid reservoir. For all subsequent delivery pulses, the value of PULSE1 is False. The fluid infusion device is primed (task 704) such that fluid is introduced into the fluid pathway and through the infusion set tubing. During priming, the force imparted to the force sensor typically spikes (to about 1.4 pounds) when the slide initially contacts the plunger of the reservoir. After priming, however, the force decays and settles to a lower value (typically around 0.5 pounds).

The process 700 activates a fluid delivery operation (task 706) to actuate the fluid reservoir, and performs the next fluid delivery action, stroke, or pulse (task 708). As explained in more detail below, tasks 706 and 708 are usually performed after the priming operation is complete and after the force has settled to its nominal value (of about 0.5 pounds). If, however, the user commands a fluid delivery operation prematurely while the force is still decaying, then the force imparted to the force sensor at that time may be above the nominal value. The process 700 contemplates this scenario, as described below.

The process 700 continues by determining or obtaining a current measure of actuation force imparted to the force sensor for the current fluid delivery pulse (task 710), as described previously. The current measure of actuation force (F) is recorded or saved in an appropriate manner. If PULSE1 is True (query task 712), meaning that the pulse actuated at task 708 is the first pulse for the installed reservoir, then the process 700 continues by setting the value of PULSE1 to "False" (task 714), and by comparing the current measure of actuation force (F) to a reference upper threshold force value that applies to initial pulses (RUT1), as indicated by query task 716. The value of RUT1 is selected to account for situations where the initial pulse is commanded prematurely, i.e., before the force has settled to its nominal value after priming. In other words, RUT1 is selected to contemplate the possibility of unusually high force measurements associated with the first pulse commanded for a newly installed reservoir. For this particular example (where the normally expected nominal actuation force for the fluid reservoir is about 0.4 pounds), the value of RUT1 may be chosen to be about 0.5 pounds, without limitation.

If the current measure of actuation force is less than RUT1 (query task 716), then the process 700 stores the current measure of actuation force (task 718) for use as an adaptive reference force value ($F_R$), which is used for comparison purposes against subsequent force measurements. Execution of task 718 indicates that the actuation force associated with the initial delivery pulse does not represent a force measured shortly after priming, while the fluid in the delivery path is still settling to its nominal state. On the other hand, if the current measure of actuation force (F) is not less than RUT1 (query task 716), then the process 700 stores the value of RUT1 as the current value of $F_R$ (task 720). Execution of task 720 indicates that the actuation force associated with the initial delivery pulse may have been sampled during a time when the fluid in the delivery path is still settling and, therefore, the measured force is still decaying from the relatively high value (e.g., about 1.4 pounds). Consequently, under this scenario the process 700 uses RUT1 as the current adaptive reference force value.

After the value of $F_R$ has been set (task 718 or task 720), the process 700 waits for the next fluid delivery pulse (task 722). When it is time to perform the next fluid delivery pulse, the process 700 returns to task 708 and continues as described above. In contrast to that described above, however, the value of PULSE1 is False for the second and all further delivery pulses. Referring again to query task 712, if PULSE1 is not True (i.e., PULSE1=False), then the process 700 may continue by comparing the current measure of actuation force to the difference between the adaptive reference force value ($F_R$) and a threshold force value (query task 724). For this example, the adaptive reference force value ($F_R$) may correspond to a past measure of actuation force that was recorded for a previous fluid delivery pulse, or it may correspond to RUT1, as described above. In particular embodiments, $F_R$ might represent the measure of actuation force for the immediately preceding fluid delivery pulse (indeed, under normal operating conditions where the fluid reservoir remains properly seated, $F_R$ will be adaptively updated to reflect the most recent measure of actuation force). In other words, the previous fluid delivery pulse associated with $F_R$ and the current fluid delivery pulse will typically be consecutive fluid delivery pulses. Thus, the process 700 stores, maintains, and updates the adaptive reference force value as needed during operation of the fluid delivery device.

In practice, the process 700 might generate or store an initial value of $F_R$ whenever a new fluid reservoir is installed, at the beginning of a fluid delivery operation, at designated times, at the request of the user, or at other appropriate times. This example assumes that $F_R$ is initialized as described above in response to the first fluid delivery pulse of a fluid delivery operation. Thus, under typical and normal operating conditions the first measure of actuation force will be used as $F_R$ for the immediately following fluid delivery pulse. If, however, the first measure of actuation force exceeds the initial upper threshold value, then the initial upper threshold value RUT1 will instead be used as $F_R$ for the next fluid delivery pulse.

Referring again to query task 724, if the current measure of actuation force (F) is not less than the difference between the adaptive reference force value ($F_R$) and the threshold force value ($F_T$), then the process 700 assumes that the fluid reservoir remains properly seated. Accordingly, the process 700 resets the count to its initial value, e.g., zero (task 726). The illustrated embodiment of the process 700 continues by comparing the current measure of actuation force (F) to an upper threshold force value (RUT), as indicated by query task 728. This upper threshold value is selected such that it is indicative of the expected maximum actuation force for the fluid reservoir. For this particular example (where the normally expected actuation force for the fluid reservoir is about 1.4 pounds), the upper threshold force value may be chosen to be about 1.8 pounds, without limitation. If the current measure of actuation force is less than the upper threshold force value, the process 700 stores the current measure of actuation force for use as $F_R$ with the next iteration (task 730). In this regard, $F_R$ can be adaptively and dynamically updated in an ongoing manner during the fluid delivery operation. After updating $F_R$, the process 700 waits until it is time to perform the next fluid delivery pulse (task 722). Referring back to query task 728, if the current measure of actuation force is not less than the upper threshold force value, then the process 700 leaves $F_R$ unchanged and waits for the next fluid delivery pulse (task 722). In other words, the previous value of $F_R$ is retained for the next processing iteration. When it is time to perform the next fluid delivery pulse, the process 700 returns to task 708 and continues as described above.

Referring again to query task 724, if $F<F_R-F_T$, then the process 700 initiates some form of corrective action, which is triggered by the detection of an abnormal or unexpected measure of actuation force. In this regard, the process 700 may place the fluid infusion device into a flagged state, perform additional checks, and/or perform additional data analysis to determine whether or not to execute corrective action, issue an alert, sound an alarm, generate a user message, etc. This particular example continues by obtaining one or more additional force readings (task 732) and calculating an average measure of actuation force ($F_{AVE}$) based on the additional force readings. In practice, $F_{AVE}$ may be calculated from the current measure of actuation force and any or all of the additional force readings. In certain embodiments, task 732 collects four additional force readings, and $F_{AVE}$ is calculated as a weighted average of the current measure of actuation force and the four repeated measures of actuation force imparted to the force sensor.

Although the process 700 could use the current measure of actuation force itself as a trigger value, the illustrated embodiment instead uses $F_{AVE}$ as the trigger value. In other words, the process 700 checks whether $F_{AVE}<F_R-F_T$ (query task 734). If $F_{AVE}$ is not less than the difference between the adaptive reference force value ($F_R$) and the threshold force value ($F_T$), then the process 700 assumes that the fluid reservoir remains properly seated, resets the count to its initial value (task 726), and continues from task 726 as described above. If, however, $F_{AVE}<F_R-F_T$, then the process 700 changes the count by a designated amount to obtain an updated count (task 736). Depending upon the embodiment and the initial count value, task 736 may increase or decrease the count. In certain embodiments, task 736 changes the count by an amount that is influenced or dictated by a volume of fluid to be delivered by a subsequent fluid delivery pulse, e.g., the next fluid delivery pulse. Alternatively, task 736 might change the count by an amount that is influenced or dictated by a volume of fluid delivered by the current fluid delivery pulse, or by a previous fluid delivery pulse. In accordance with one non-limiting example, task 736 increases the count by one when the next fluid delivery pulse corresponds to a relatively low volume of fluid (e.g., 0.025 units), increases the count by two when the next fluid delivery pulse corresponds to a relatively intermediate volume of fluid (e.g., 0.050 units), and increases the count by six when the next fluid delivery pulse corresponds to a relatively high volume of fluid (e.g., 0.200 units).

The above methodology for task 736 accounts for "slack" that is created in the drive system when the fluid infusion device is dropped or when the reservoir is dislodged. For example, assume that the slack represents a separation between the plunger of the reservoir and the tip of the actuating slide, and assume that it takes six pulses (each corresponding to a delivery of 0.025 Units), equivalent to 0.15 Units, to remove the slack. Therefore, the counter limit or threshold will be set to six. If after six "counts" the slack is not removed, i.e., the force is still low, the process 700 will trigger an alarm. If the device delivers fluid in 0.025 Unit pulses, it will take six pulses and, therefore, the count is incremented by one. On the other hand, if the fluid delivery is in 0.05 Unit increments, then the counter is incremented by two; if the fluid delivery is in 0.2 Unit pulses, the counter increments by six. Accordingly, the limit or threshold is met after six 0.025 Unit pulses, after three 0.05 Unit pulses, or after only one 0.2 Unit pulse. This allows the fluid infusion device to deliver various pulses and increment correctly.

After obtaining the updated count, the process 700 checks whether the updated count satisfies certain predetermined alert criteria (query task 738). The alert criteria for the illustrated embodiment is simply a threshold count value or a limit, such as twelve or any appropriate number. Thus, if the updated count is greater than the limit, then the process 700 assumes that the fluid reservoir has been dislodged, loosened, or unseated. Consequently, the process 700 initiates and executes appropriate corrective action (task 740), e.g., generates a seating status alert or some indicia of an unseated fluid reservoir. Alternatively or additionally, the corrective action taken by the fluid infusion device may include, without limitation, one or more of the actions described above for the process 200 (see FIG. 5). If, however, query task 738 determines that the updated count does not satisfy the stated alert criteria, then the process 700 does not actually implement or execute any corrective action at this time. Rather, the process 700 may lead back to task 722 to wait for the next fluid delivery pulse, as described above. Notably, corrective action is executed by the illustrated embodiment of the process 700 only when the count exceeds the threshold limit. Moreover, the manner in which the count is reset by the process 700 ensures that unexpectedly low actuation force readings must be recorded for consecutive fluid delivery pulses before the fluid delivery device actually issues a warning or an alert. These aspects of the process 700 reduce nuisance alerts and allow the fluid infusion device to recover from transient conditions that might cause a temporary drop in the measured actuation force (e.g., dropping or bumping the fluid infusion device, mishandling the fluid infusion device, or the like). In certain embodiments, if at any point when the force is low and the count is being updated the force increases (i.e., the slide contacts the plunger of the reservoir), the counter is again reset to zero.

Figure 11:
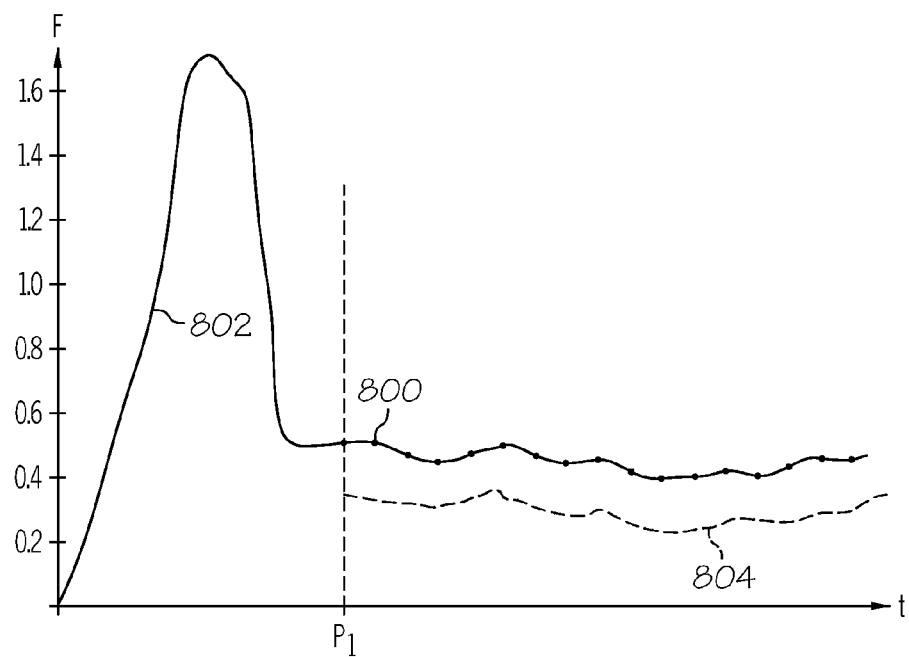
FIG. 11 is a graph that illustrates measures of actuation forces for a properly seated fluid reservoir.

FIG. 11 is a graph that illustrates measures of actuation forces for a properly seated fluid reservoir. The plot 800 represents actuation force versus time (or, equivalently, fluid delivery pulses). The initial portion 802 of the plot 800 corresponds to the seating of the fluid reservoir. In practice, the device stops the seating process when a force of about 1.4 pounds is reached. Momentum of the motor results in some additional actuation, resulting in a peak of about 1.8 pounds. After seating and priming, however, the nominal force typically settles to about 0.5 pounds. Accordingly, the label $P_1$ represents the first fluid delivery pulse following the seating/ priming procedure. The dashed line 804 schematically represents the threshold force value corresponding to the allowable drop in actuation force over any two consecutive fluid delivery pulses. Notably, even though the plot 800 fluctuates somewhat, the actuation force values do not violate the limit defined by the threshold force value. In other words, the plot 800 is indicative of a properly seated fluid reservoir under normal and expected operating conditions.

Figure 12:
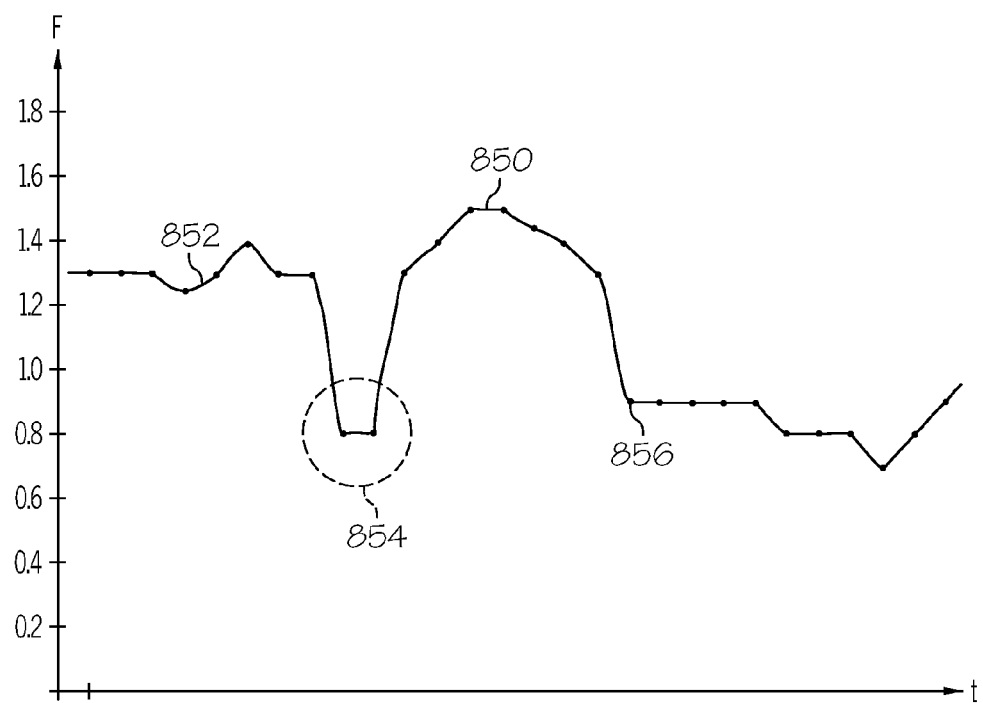
FIG. 12 is a graph that illustrates measures of actuation forces for a fluid reservoir that becomes unseated.

In contrast, FIG. 12 is a graph that illustrates measures of actuation forces for a fluid reservoir that becomes unseated. The plot 850 begins at a point after initial seating of the fluid reservoir. The initial segment 852 of the plot 850 is indicative of a properly seated fluid reservoir (assuming that the threshold force value is 0.15 pounds). The plot 850 experiences a temporary drop 854 that spans two fluid delivery pulses. For this example, the temporary drop 854 would trigger the counting mechanism described above with reference to the process 700. However, the plot 850 recovers after the temporary drop 854 and, therefore, the count would be reset and no alert would be generated. At the fluid delivery pulse 856, the plot 850 exhibits a significant and "permanent" drop. At this point, the counting mechanism would be activated. Notably, the drop in measured actuation force does not recover even after ten consecutive fluid delivery pulses. Consequently, the count continues to increase and, for this example, the upper count limit is eventually reached. At that time, the fluid infusion device would generate an appropriate alert, alarm, or warning message, as described previously.

Adaptive Occlusion Detection

The force sensor 126 and/or other sensors, measurement devices, or components in the fluid infusion device 100 may also be used for purposes of occlusion detection. Most conventional occlusion detection schemes function by triggering an occlusion alarm when a certain preset threshold force is reached. For example, if the typical actuation force for a fluid reservoir is about one pound and the occlusion threshold is three pounds, a detected force that exceeds three pounds will initiate an alert or an alarm. In fluid infusion devices that are occluded, the force might increase by only fractions of a pound per unit of fluid (e.g., insulin) desired to be delivered. As a result, there can potentially be long wait times before an occlusion is actually confirmed.

In contrast, the technique described here is adaptive in nature, and occlusions can be determined prior to reaching the preset threshold by evaluating consecutive rates of change (slopes) of force. For example, assume that the typical force variation in a reservoir is only about 0.02 pound per unit (lb/U) over three or four delivery strokes or pulses. If an occlusion is present, the detected force might increase at a calculated rate of 0.30 lb/U over four consecutive pulses. If the fluid infusion device detects an occlusion, then an alarm might be generated and/or the occlusion force threshold might be adjusted downward by a certain amount. For example, if the normal occlusion threshold is three pounds, a detected occlusion condition might result in a downward adjustment of the occlusion threshold by thirty percent, resulting in an adjusted occlusion threshold of about two pounds. The adaptive approach enables the fluid infusion device to quickly detect an occlusion, relative to traditional methods that only use a static force threshold.

Figure 13:
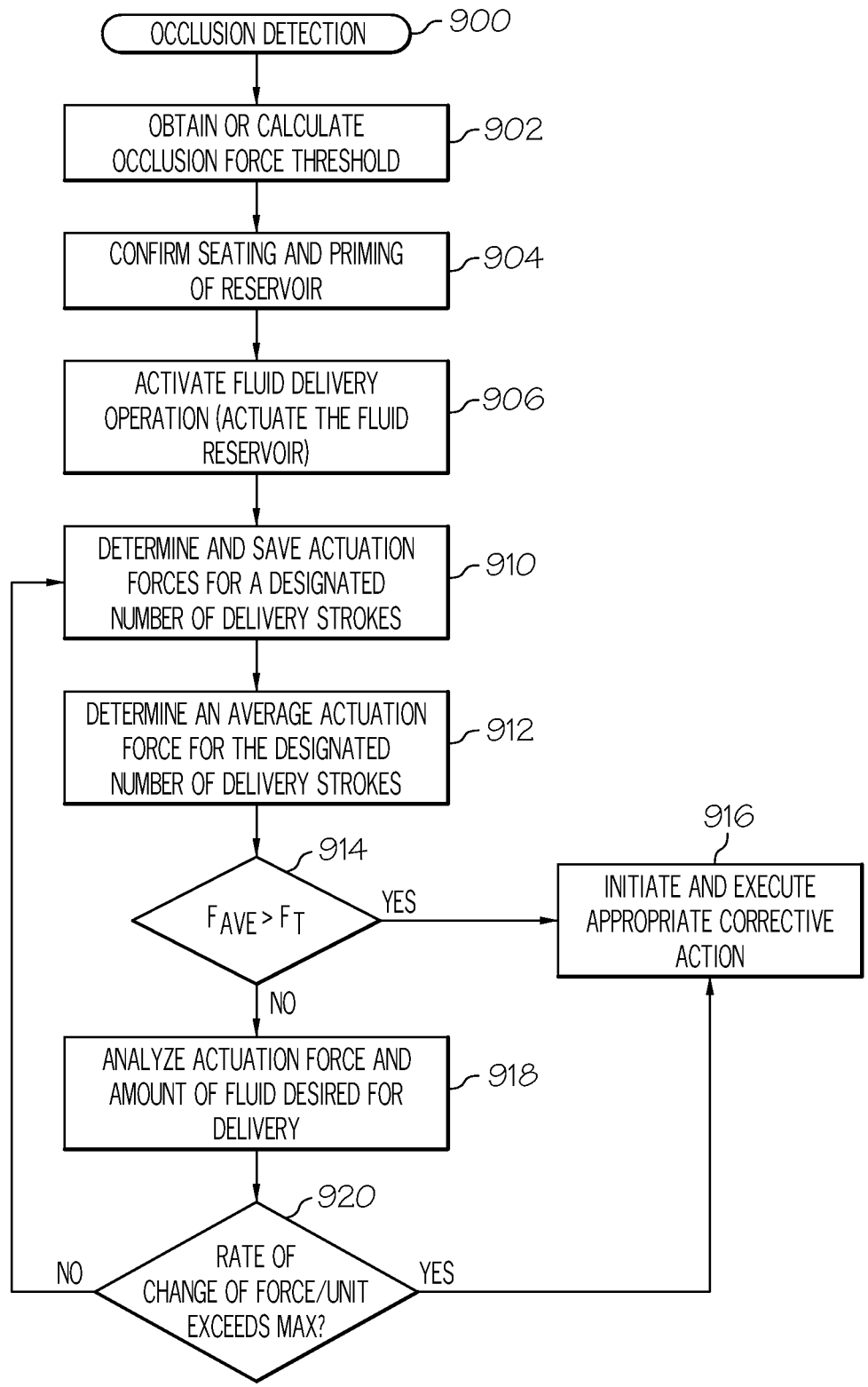
FIG. 13 is a flow chart that illustrates an embodiment of an occlusion detection process for a fluid infusion device.

FIG. 13 is a flow chart that illustrates an embodiment of an occlusion detection process 900 for a fluid infusion device, such as the fluid infusion device 100 described above. This embodiment of the process 900 employs an occlusion force threshold, which is consistent with traditional methodologies. Thus, the process 900 may begin by obtaining, calculating, or retrieving the occlusion force threshold (task 902). In typical implementations this occlusion force threshold is about 2.4 pounds, although the actual amount may vary from one embodiment to another.

In practice, the process 900 can be performed whenever a fluid reservoir is installed into the fluid infusion device. Accordingly, the process 900 may confirm the initial seating and/or priming of the fluid reservoir (task 904), and then activate a fluid delivery operation, which in turn actuates the fluid reservoir with the drive motor assembly (task 906). As described in more detail above, actuation of the fluid reservoir causes an amount of force to be imparted to the force sensor. Accordingly, the process 900 determines and saves actuation forces for a designated number of delivery strokes (task 910). This particular embodiment determines and saves actuation forces for a plurality of consecutive delivery strokes and then determines an average actuation force for the plurality of delivery strokes (task 912).

The process 900 may continue by comparing the average actuation force ($F_{AVE}$) to the occlusion force threshold ($F_T$) obtained at task 902. If the average actuation force is greater than the occlusion force threshold (query task 914), then the fluid infusion device initiates and executes appropriate corrective action (task 916). The corrective action taken by the fluid infusion device may include, without limitation, one or more of the actions described above for the process 200 (see FIG. 5). If, however, query task 914 determines that the average actuation force is not greater than the occlusion force threshold, then the process 900 continues.

The process may continue by analyzing the actuation force and the amount of fluid (typically expressed as a number or fraction of units) that is desired to be administered for delivery (task 918). As mentioned above, the process 900 analyzes the rate of change of a metric corresponding to the amount of detected force per unit of fluid (as commanded by the fluid infusion device). In this regard, the process 900 may compute this metric (e.g., in lb/U) in an ongoing manner during the fluid delivery operation. Moreover, the process 900 calculates the rate of change of this metric in an ongoing manner during the fluid delivery operation. Consequently, if the fluid infusion device determines that the rate of change exceeds a predetermined maximum value (query task 920), then the process 900 leads to task 916 and initiates appropriate corrective action. If, however, query task 920 determines that the rate of change does not exceed the maximum value, then the process 900 assumes that the fluid delivery path is not occluded. Accordingly, the process 900 returns to task 910 to continue monitoring actuation forces for the current fluid delivery operation (and for subsequent fluid delivery operations). The maximum tolerable rate of change may be a fixed value or it may be adaptive in nature. In typical embodiments, the maximum rate of change value will be about 1.0 lb/unit, although different values could be used depending upon the embodiment.

It should be appreciated that the process 900 may be practiced in conjunction with conventional occlusion detection schemes if so desired. For example, one or more of the occlusion detection approaches described in U.S. Pat. Nos. 6,485,465 and 7,621,893 (or modified versions thereof) could be employed with the process 900.

Multi-Metric Occlusion Detection

The force sensor 126 in the fluid infusion device 100 may also be used to support a multi-metric occlusion detection scheme. The multi-metric occlusion detection approach may be used with or without a traditional reservoir force threshold approach. One benefit of the multi-metric technique is that it accommodates drifting or other changes of the force sensor, which might occur over the lifespan of the fluid infusion device 100. In practice, therefore, the multi-metric technique can tolerate drifting of the force sensor without generating false alarms, while still accurately detecting the presence of an occlusion.

The exemplary approach presented here employs a rate of change methodology incorporating two different conditions to take advantage of the rate of change in force with respect to fluid delivery. If either of the two conditions is satisfied, the fluid infusion device 100 indicates an occlusion and takes appropriate action. The rate of change approach is desirable because it does not depend solely on the system to settle to a force level. Moreover, the approach described here does not rely on the starting frictional force of a reservoir. In practice, different reservoirs might have different nominal actuation forces; for example, reservoir A may have running force of 1.0 pound, and reservoir B may have a running force of 1.8 pounds. Based on a simple threshold force alone, it will take more time for reservoir A to reach occlusion than reservoir B. Using the rate of change approach presented here, as long as the threshold rate of change is reached, occlusion will be detected independent of starting frictional force value.

The first monitoring mode uses one rate of change of reservoir force as a triggering parameter, where the rate of change is determined for a relatively large delivery window. For example, assume that the measured rate of change in force over fluid delivery in a three-unit (3 U) window is not to exceed 0.375 lb/unit. If, over any three-unit window, the rate of change exceeds 0.375 lb/unit, the fluid infusion device 100 alarms. It is desirable to have a predetermined measurement window (3 U in this case) because during normal delivery there might be some sudden changes in force. In this regard, a reservoir might experience a running force of 1.0 pound and suddenly increase to 1.3 pounds over a delivery window of 0.5 units, and continue to deliver at 1.3 pounds. This scenario would not be indicative of an occlusion; rather, this would be indicative of a normal variation in force. If the measurement window of three units is not utilized, this scenario could have led to a false occlusion alarm.

In practice, the measurement window and the rate of change threshold should be large enough to avoid false positives. However, most of the time these parameters can be more restrictive. Accordingly, the exemplary embodiment described here utilizes the second monitoring mode, which employs a different rate of change threshold and a smaller measurement window, along with a threshold force value that serves as an "early" indication of a possible occlusion. For the exemplary embodiment described here, if a reservoir is known to be operating at actuation forces beyond its normal range (for example above 1.4 pounds), then the second condition will be considered. For example, if the measured actuation force is 1.8 pounds, the fluid infusion device 100 recognizes that the nominal operating load has been exceeded, but the fluid infusion device 100 does not determine the presence of an occlusion based solely on this high force reading (high forces can be caused by an overly sensitive force sensor, among other reasons). If, however, the rate of change of the force also exceeds a predetermined threshold value, then the fluid infusion device 100 alarms. In this scenario, the rate of change and the measurement window can be selected for higher detection sensitivity because the fluid infusion device 100 is already operating at a higher than normal reservoir actuation force. The second condition is based on the observation that a reservoir that is over the force limit and also experiencing an increasing rate of change in force is most likely to be occluded.

The multi-rate approach presented here allows the fluid infusion device 100 to tolerate actuation forces that are slightly above the nominal reservoir force range, yet not generate an alarm unless one of the conditions (with different measurement windows and different rates of change of force) is met. This approach allows the fluid infusion device 100 to experience a slightly higher force due to mechanical issues, normal lifespan variation, and/or an oversensitive force sensor, while continuing to function within safe and predictable limits.

Figure 14:
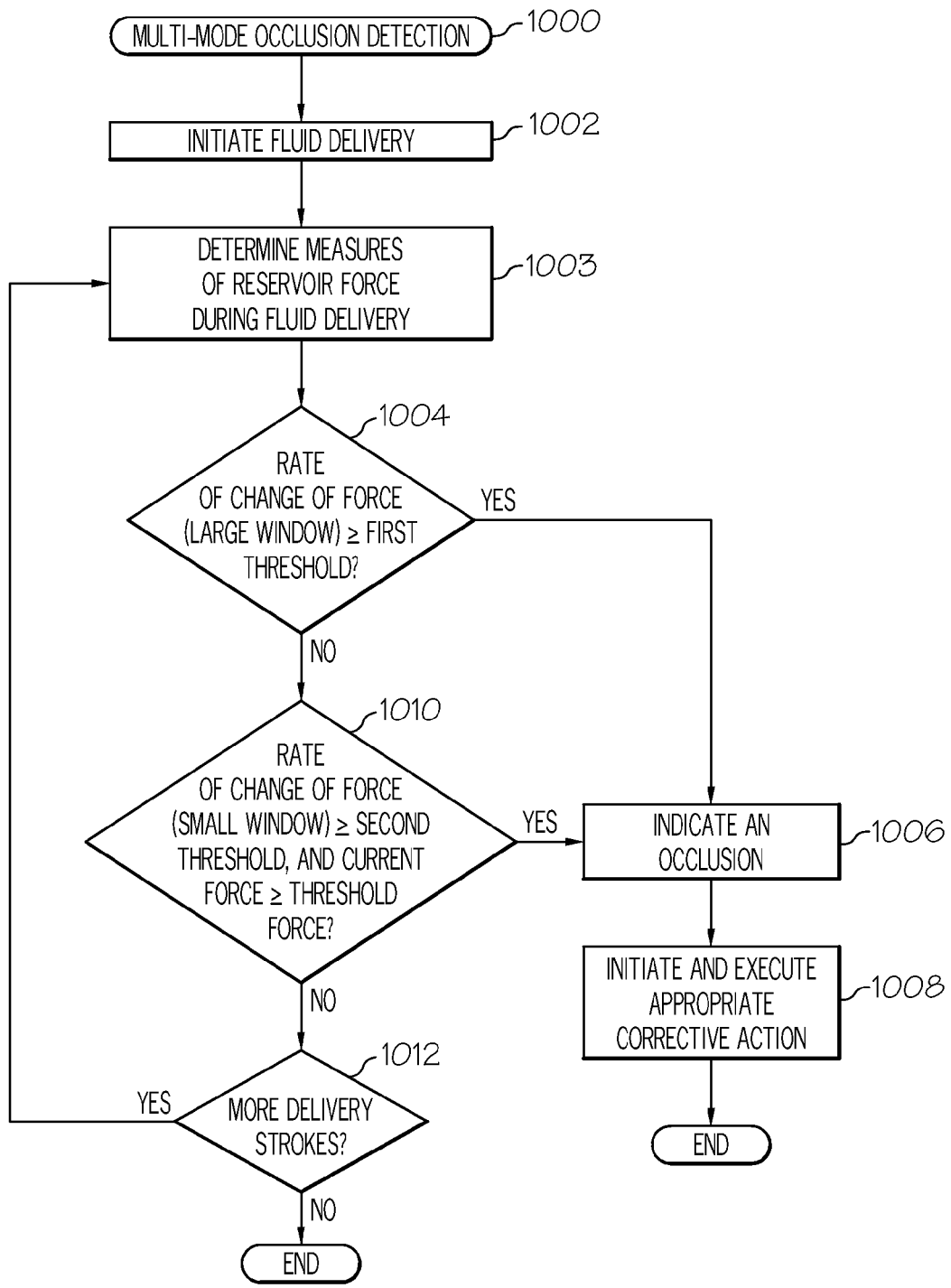
FIG. 14 is a flow chart that illustrates an exemplary embodiment of a multi-mode occlusion detection process.

FIG. 14 is a flow chart that illustrates an exemplary embodiment of a multi-mode occlusion detection process 1000 for an infusion device, such as the fluid infusion device 100. The process 1000 may be performed in connection with any fluid delivery operation or action, such as the delivery of therapy, the priming of the fluid path, the initializing of a new fluid reservoir, or the like. Accordingly, the process 1000 may begin by initiating or activating a fluid delivery action (task 1002) to deliver a designated or commanded amount of fluid from the fluid reservoir. The fluid delivery action actuates the fluid reservoir with the drive motor assembly, as described previously. The fluid delivery action may be stepwise or continuous, depending upon the particular embodiment. This example assumes that the fluid reservoir is actuated in a stepwise or pulsed manner, with a series of discrete actuation strokes that collectively result in the desired amount of fluid delivered from the reservoir.

During the fluid delivery action the process 1000 determines, obtains, or samples one or more measures of actuation force, using the force sensor (task 1003). Each measure of force corresponds to an output level recorded from the force sensor. In practice, therefore, a measure of force (also referred to here as a "force measurement") may be a voltage, a current, a capacitance, a resistance, a digital value, an analog value, or any detectable characteristic of the force sensor that somehow indicates the actuation of pressure in the fluid reservoir. The exemplary embodiment determines a plurality of force measurements during the commanded fluid delivery action, and each force measurement also has an associated quantity metric or measurement (e.g., a delivered volume of fluid relative to a reference volume or other reference point). Alternatively (or additionally), each force measurement might be associated with a corresponding time, delivery stroke, or other measurable parameter that can be used to calculate a rate of change of the actuation force.

The process 1000 detects an occlusion in one of two different modes associated with different measurement windows. As used here, a "measurement window" may refer to one or more of the following, without limitation: a period of time; a delivery time relative to a reference time; a measure of quantity (e.g., a delivered volume, mass, or weight); an amount of travel or distance associated with actuation of the piston of the fluid reservoir; a number, a count, or other parameter associated with turns or rotation of the drive motor assembly; a measured amount of fluid flow; or the like. For the exemplary embodiment described here, the measurement windows represent a volume of fluid dispensed from the fluid reservoir. Moreover, each measurement window is identified relative to a reference volume measurement.

Figure 15:
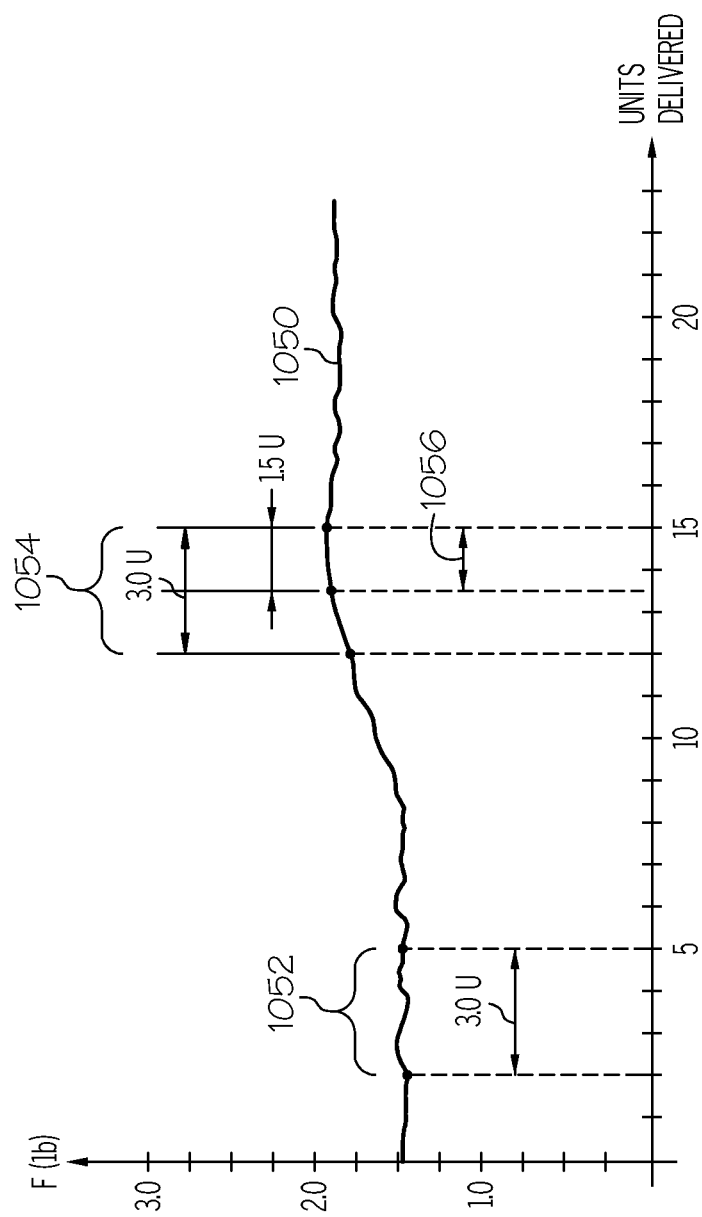
FIG. 15 is a graph that depicts an exemplary plot of fluid reservoir actuation force versus volume of fluid delivered from a fluid infusion device.

FIG. 15 is a graph that depicts an exemplary plot 1050 of fluid reservoir actuation force versus volume of fluid (units) delivered from a fluid infusion device. FIG. 15 illustrates the concept of measurement windows. For example, a measurement window 1052 is defined such that it corresponds to a delivered volume of 3.0 units. This measurement window 1052 may be defined by the current state of the fluid infusion device and a previous state of the fluid reservoir. For this example, the current state of the fluid infusion device corresponds to the point where 5.0 units have been delivered, and the previous state corresponds to the point where 2.0 units have been delivered, i.e., the state when the fluid reservoir had 3.0 more units of fluid. Each measurement window may correspond to a moving window that tracks the real-time status of the fluid infusion device and the real-time status of the fluid reservoir. Thus, as the fluid reservoir progresses from its "full" state to its "empty" state, a measurement window can move to contemplate any two moving endpoints that define the predetermined volume (for the exemplary embodiment, one of the two endpoints corresponds to the current state, the current force measurement, and the current volume measurement).

The exemplary embodiment of the process 1000 employs two different measurement windows, e.g., a large window and a small window. For ease of understanding, FIG. 15 depicts two measurement windows relative to a point at which 15.0 units have been delivered from the fluid reservoir. The large (3.0 units) window 1054 and the small (1.0 unit) window 1056 are both measured relative to the current measurement point of 15.0 units. Referring again to FIG. 14, if the rate of change of the measure of force (based on the large window) is greater than or equal to a first threshold value (query task 1004), then the process 1000 indicates an occlusion (task 1006) and initiates and executes appropriate corrective action (task 1008). The corrective action taken by the fluid infusion device may include, without limitation, one or more of the actions described above for the process 200 (see FIG. 5). If the rate of change is less than the first threshold value (the "No" branch of query task 1004), then the process 1000 may proceed to a query task 1010, which compares the rate of change of the measure of force (based on the small window) to a second threshold value. More specifically, the process 1000 indicates an occlusion (task 1006) if: (a) the rate of change of the measure of force (based on the small window) is greater than or equal to the second threshold value; and (b) the current force measurement is greater than or equal to a threshold force value. For this particular embodiment, the first rate of change threshold value is greater than the second rate of change threshold value.

If the first rate of change is less than the first threshold value and the second rate of change is less than the second threshold value (the "No" branch of query task 1010), then the process 1000 may check to determine whether more delivery strokes or pulses are needed for the current fluid delivery operation (query task 1012). If more delivery stokes are required, then the process 1000 waits for and executes the next fluid delivery pulse and returns to task 1003 to continue as described above. If there are no additional delivery strokes required, then the process 1000 ends.

The above description of the process 1000 assumes that the small and large windows are fixed in size. In certain embodiments, however, the small and/or large window size could vary as a function of the current force measurement. For example, as the current measured force increases, the small window size may decrease. Similarly, the first threshold slope value and/or the threshold slope value could vary as a function of the current force measurement if so desired.

Figure 16:
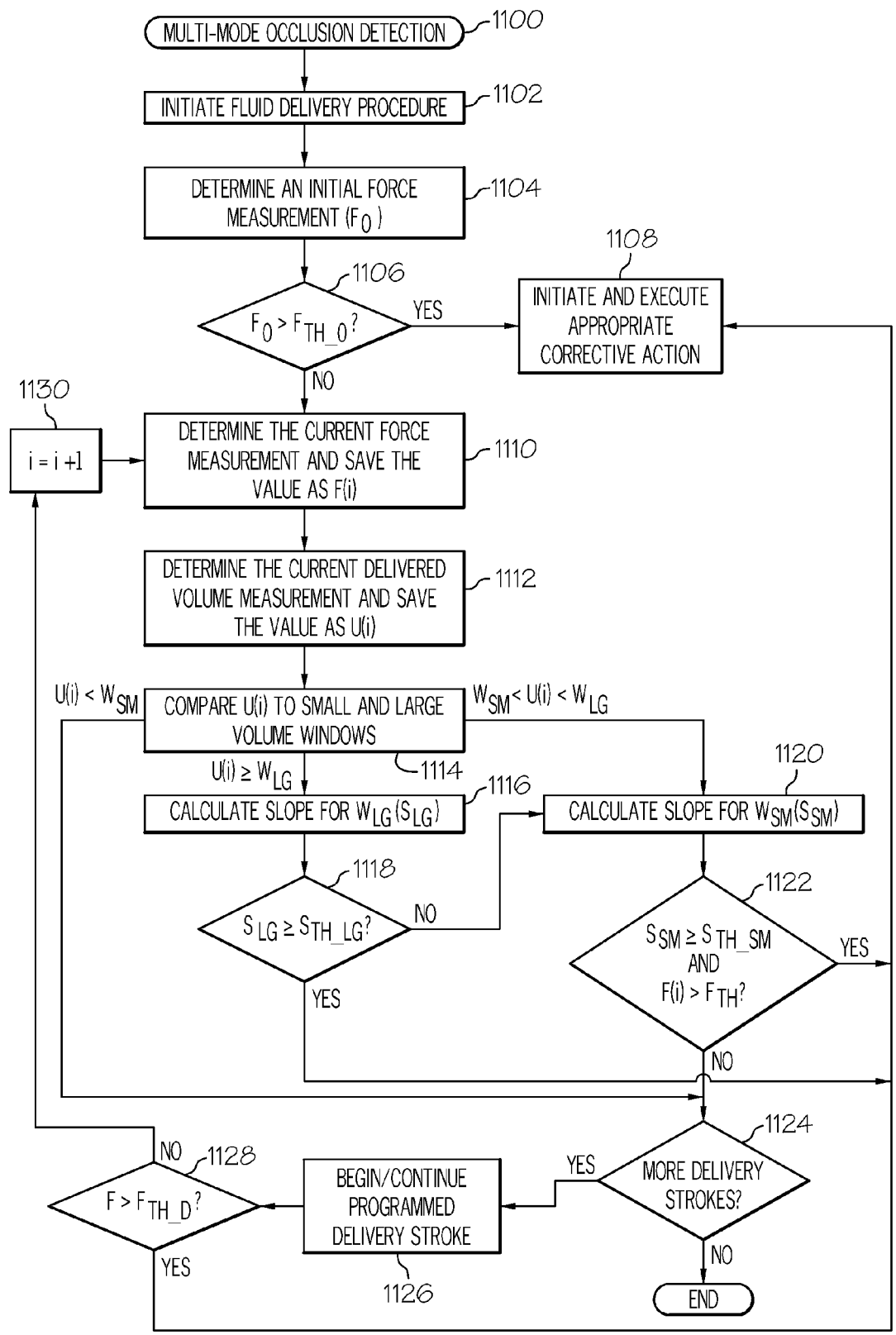
FIG. 16 is a flow chart that illustrates another exemplary embodiment of a multi-mode occlusion detection process.

The process 1000 represents a simplified and generalized version of a multi-mode occlusion detection technique. In practice, a fluid infusion device could carry out an occlusion detection process having more detailed steps and specific operating parameters. In this regard, FIG. 16 is a flow chart that illustrates another exemplary embodiment of a multi-mode occlusion detection process 1100. The following description utilizes certain parameters and settings for an exemplary implementation. These parameters and settings are not intended to limit or otherwise restrict the scope or application of the described subject matter in any way. The parameters, settings, and variables used in the following description of the process 1100 are:

$F_0$=initial force measurement
$F_{TH\_0}$=4.0 pounds=initial force limit or threshold
$F_{TH\_D}$=4.0 pounds=gross delivery force limit or threshold
i=index variable
$F(i)$=current force measurement
$F_{TH}$=1.8 pounds=threshold force value
$U(i)$=delivered volume measurement, relative to a reference volume
$W_{SM}$=1.5 unit=small volume window
$W_{LG}$=3.0 units=large volume window
$S_{SM}$=calculated slope for the small window
$S_{LG}$=calculated slope for the large window
$S_{TH\_SM}$=0.220 lb/U=threshold slope value for the small window
$S_{TH\_LG}$=0.380 lb/U=threshold slope value for the large window The process 1100 may be performed in connection with any fluid delivery operation or action and, as such, the process 1100 may begin by initiating a fluid delivery action (task 1102) to deliver a designated or commanded amount of fluid from the fluid reservoir. At this point, fluid need not be actually delivered. Rather, the process 1100 is initiated when the system intends to deliver fluid to check whether or not an occlusion is present before actually delivering fluid. The process 1100 determines, measures, or obtains a plurality of force measurements during the fluid delivery operation of the drive motor assembly, including an initial force measurement ($F_0$) and at least one subsequent force measurement. The illustrated embodiment performs an initial gross occlusion check before or at the beginning of each fluid delivery action. To this end, the process 1100 determines the initial force measurement (task 1104), which indicates an initial measure of actuation force imparted to the force sensor, and compares the initial force measurement ($F_0$) to the initial force limit ($F_{TH0}$) (query task 1106). If $F_0 > F_{TH\_0}$, the fluid infusion device indicates an occlusion and initiates and executes appropriate corrective action (task 1108), as described previously. For this example, the value of $F_{TH\_0}$ (4.0 pounds) is intentionally chosen to be much higher than any normal operating actuation force and to be greater than the force threshold ($F_{TH}$) that is used during fluid delivery. The process 1100 assumes that any measured force above $F_{TH\_0}$ is by definition caused by an occlusion and, therefore, the "Yes" branch of query task 1106 leads directly to the task 1108 for immediate corrective action.

If $F_0$ is less than or equal to the initial force limit, then the process 1100 determines the current force measurement and saves the value as $F(i)$ (task 1110). The value of $F(i)$ may be calculated in any desired manner. This particular example determines $F(i)$ by averaging a number of force measurements that are sampled while the drive motor assembly is stationary, e.g., immediately before or immediately after a delivery pulse. More specifically, the process 1100 may acquire ten force readings, discard the maximum and minimum readings, and compute the average of the remaining eight readings to arrive at $F(i)$.

The process 1100 also determines a plurality of quantity measurements during the fluid delivery action, where each quantity measurement is determined relative to a reference quantity measurement, and where each quantity measurement corresponds to a respective one of the force measurements. For this embodiment, each quantity measurement represents or indicates a volume of fluid dispensed from the fluid reservoir, relative to a reference volume, a reference time, or any appropriate reference point or marker. In practice, the reference volume may be defined to be any initial value (such as zero units) when a fluid reservoir is installed in the fluid infusion device, after completion of a priming function for a newly installed fluid reservoir, immediately following the completion of a fluid delivery operation, or the like. Thus, if the current fluid delivery operation is intended to deliver 0.5 units and the reference volume is 0.0 units, then the recorded volume measurements should range between 0.0 units and 0.5 units. Referring again to FIG. 16, the process 1100 determines the current delivered volume measurement and saves the value as U(i) (task 1112). Accordingly, each saved force measurement will have a corresponding saved volume measurement with the same index (i) value.

The process 1100 analyzes the force and volume measurements over two different measurement windows, as described previously. Accordingly, the process 1100 must collect enough measurement points before determining whether an occlusion has occurred. In this regard, the process 1100 may compare the current delivered volume measurement U(i) to the predetermined small and large volume windows (task 1114). If U(i)<$W_{SM}$ (which is 1.5 unit for this example), then the process 1100 may skip to a query task 1124. The process 1100 skips to query task 1124 at this time because additional measurement points are needed before the intervening tasks can be properly executed.

If U(i)≥$W_{LG}$ (which is 3.0 units for this example), then the process 1100 assumes that enough measurement points have been collected, and continues by calculating a slope (rate of change) for a large sample of volume measurements (task 1116). In other words, the process calculates a slope ($S_{LG}$) that is based on the large volume window. The value of $S_{LG}$ may be calculated using any suitable formula, algorithm, technique, or methodology. This particular example calculates $S_{LG}$ based on the two "endpoints" of the large volume window. More specifically, $S_{LG}$ is calculated based upon the current force measurement F(i), the current volume measurement U(i), a previous force measurement taken 3.0 units "in the past", and a previous volume measurement taken 3.0 units "in the past". Referring again to the scenario depicted in FIG. 15, the slope for the large window 1054 would be computed based on the forces measured at 15.0 units and at 12.0 units. The simple linear slope calculation employed by the process 1100 disregards measurement points taken between the two endpoints. Alternate embodiments may, of course, consider any number of intervening measurement points if so desired.

The process 1100 may continue by comparing the calculated value of $S_{LG}$ to the stated value of $S_{TH\_LG}$ (which is 0.380 lb/U for this example). If $S_{LG}$>0.380 lb/U (the "Yes" branch of query task 1118), then the process 1100 indicates an occlusion and initiates and executes appropriate corrective action (task 1108). In practice, this condition is indicative of a gradually increasing slope over a relatively large measurement window, even though a threshold actuation force has not been reached. Accordingly, the fluid infusion device can still generate an appropriate alarm without relying on a threshold trigger. If, however, $S_{LG}$<0.380 lb/U (the "No" branch of query task 1118), then the process 1100 may continue by calculating a slope ($S_{SM}$) that is based on the small volume window (task 1120). It should be appreciated that task 1120 need not be performed in response to the determination made during query task 1118. Indeed, task 1116 and task 1120 could be performed in parallel and in an ongoing and dynamic manner during the fluid delivery operation regardless of the results of the various query tasks included in the process 1100.

Referring again to task 1120, the value of $S_{SM}$ may be calculated using any suitable formula, algorithm, technique, or methodology. This particular example calculates $S_{SM}$ based on the two "endpoints" of the small volume window. More specifically, $S_{SM}$ is calculated based upon F(i), U(i), an intervening force measurement taken 1.5 unit "in the past", and an intervening volume measurement taken 1.5 unit "in the past". The intervening force measurement and the intervening volume measurement are "intervening" in the sense that they correspond to a state of the fluid infusion device that occurred at a time between the current state and the "previous" state, where the "previous" force measurement and the "previous" volume measurement are associated with the endpoint of the large measurement window as described above. Referring again to the scenario depicted in FIG. 15, the slope for the small window 1056 would be computed based on the forces measured at 15.0 units and at 13.5 units.

The process 1100 may continue by comparing the calculated value of $S_{SM}$ to the stated value of $S_{TH\_SM}$ (which is 0.220 lb/U for this example). For this example, the process 1100 indicates an occlusion when both: (a) $S_{SM}$>0.220 lb/U; and (b) F(i)≥$F_{TH}$ (the "Yes" branch of query task 1122). Indication of an occlusion at this time also causes the process 1100 to initiate and execute appropriate corrective action (task 1108). In practice, this condition is indicative of an increasing slope over a relatively small measurement window, combined with the actuation force exceeding a stated threshold level (1.8 pounds for this example). Accordingly, the fluid infusion device can utilize a sensitive slope criteria if the actuation force is already above a certain threshold value. Moreover, the different sized measurement windows (small volume versus large volume, short delivery time versus long delivery time, shorter piston travel versus longer piston travel, etc.) facilitate accurate occlusion detection while reducing the likelihood of false alarms.

If $S_{SM}$<0.220 lb/U (the "No" branch of query task 1122), then the process 1100 may continue by checking whether more delivery strokes or pulses are needed for the current fluid delivery operation (query task 1124). If there are no additional delivery strokes required, then the process 1100 ends. If more delivery stokes are required, then the process 1100 may begin or continue the programmed delivery stroke (task 1126) to actuate the fluid reservoir by the desired amount. In connection with the next delivery stroke or pulse, the process 1100 may perform another gross occlusion check (query task 1128). To this end, the process 1100 compares the current force measurement to the gross delivery force limit ($F_{TH\_D}$), which is 4.0 pounds for this example. If F>$F_{TH\_D}$, the fluid infusion device indicates an occlusion and initiates and executes appropriate corrective action (task 1108), as described previously. Otherwise, the process 1100 increments the index (i) at task 1130, and continues in the manner described above, beginning at task 1110. Thus, the process 1100 continues to monitor for an occlusion using both of the slope conditions, while updating and moving the two measurement windows dynamically as the fluid reservoir delivers additional fluid. The small and large volume windows employ the current measurement point as one endpoint, and previous measurement points as the other endpoints (e.g., 1.5 unit in the past and 3.0 units in the past). These measurement windows dynamically shift as the fluid reservoir is actuated such that the fluid infusion device samples and processes the measurement points that fall within the boundaries of the windows. Referring to FIG. 15, the measurement window would shift to the right as the fluid reservoir is actuated.

The occlusion detection techniques described above assume that actuation force is the metric or measurement quantity used to determine whether or not an occlusion in the fluid path has occurred. In such embodiments, a force sensor is utilized to obtain the measurements. In alternate embodiments, the fluid infusion device may obtain and process measurements of any quantity (or quantities) that is indicative of pressure in the fluid delivery path for purposes of occlusion detection. In this regard, actuation force associated with the fluid reservoir is an indirect way of measuring fluid pressure, where increasing fluid pressure is indicative of a potential occlusion.

Depending upon the particular implementation, the measured or detected quantity might be associated with one or more of the following, without limitation: reservoir actuation force (as described in detail above); fluid pressure in the fluid path of the device; a flow rate of fluid in the fluid path, based on time, number of delivery strokes or pulses, etc.; electric current of the drive motor, which relates to the load on the drive motor, which in turn relates to the fluid pressure in the reservoir; torque of the drive motor, which relates to the load on the drive motor, which in turn relates to the fluid pressure in the reservoir; or the like. In practice, therefore, the fluid infusion device may obtain measurement information or data from one or more sources in lieu of or in addition to a force sensor. For example, the occlusion detection schemes presented above may process measurements obtained from one or more of the following, without limitation: a pressure sensor; a flow meter; a torque meter; an electrical circuit that measures motor current; or any appropriate sensor, detector, or circuit that is dynamically responsive to the fluid pressure in the fluid path or reservoir of the fluid infusion device.

Reservoir Seating Procedure for Alternative Embodiment

Figure 17:
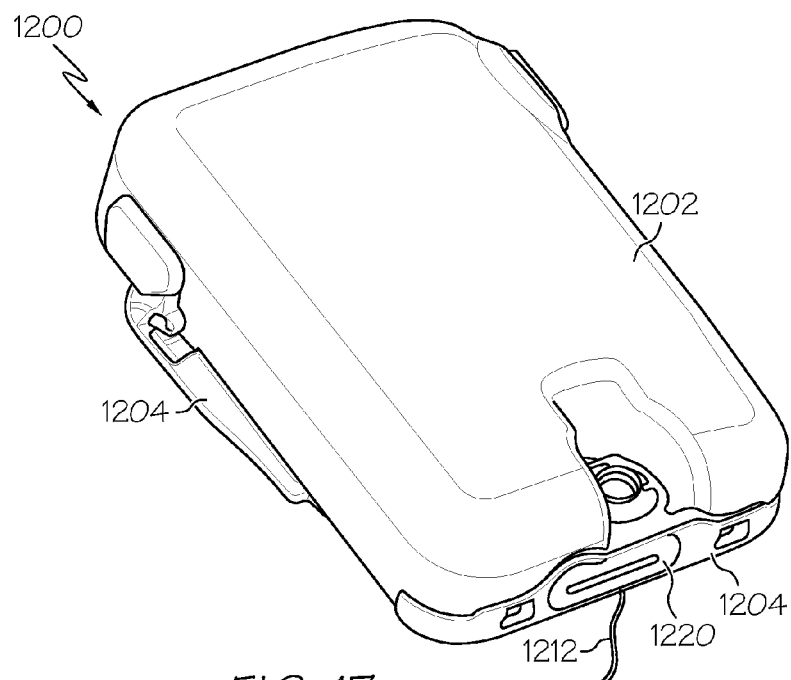
FIG. 17 is a perspective view of an embodiment of a compact patient-worn fluid infusion device.
Figure 18:
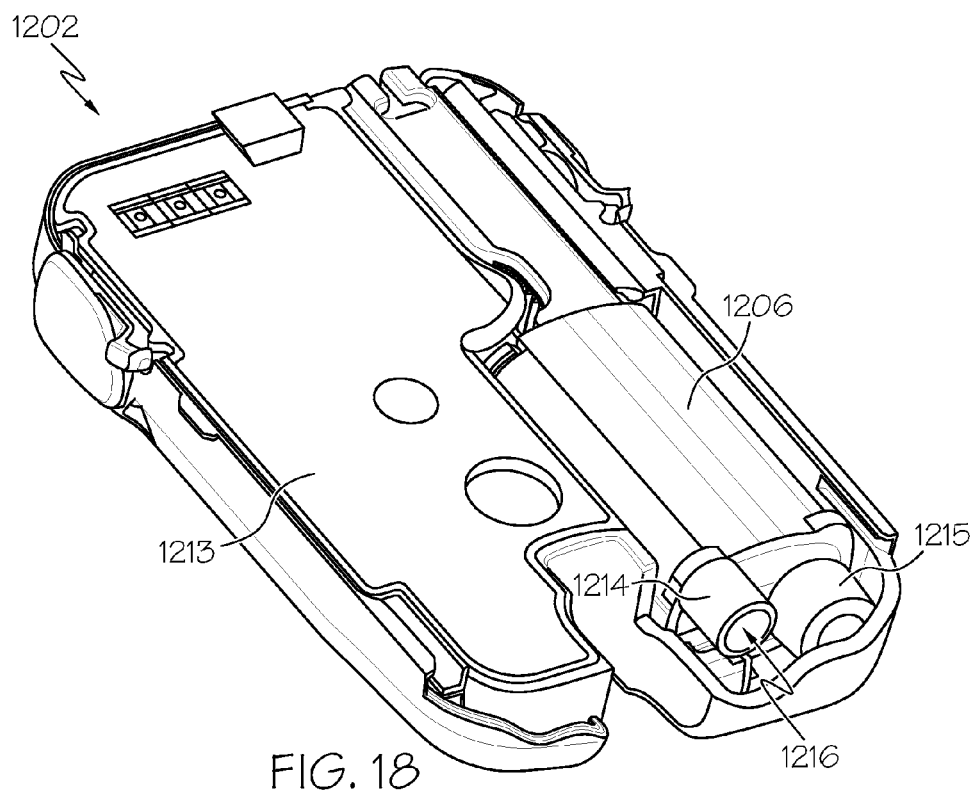
FIG. 18 is a perspective view that depicts internal structure of the durable housing of the fluid infusion device shown in FIG. 17.
Figure 19:
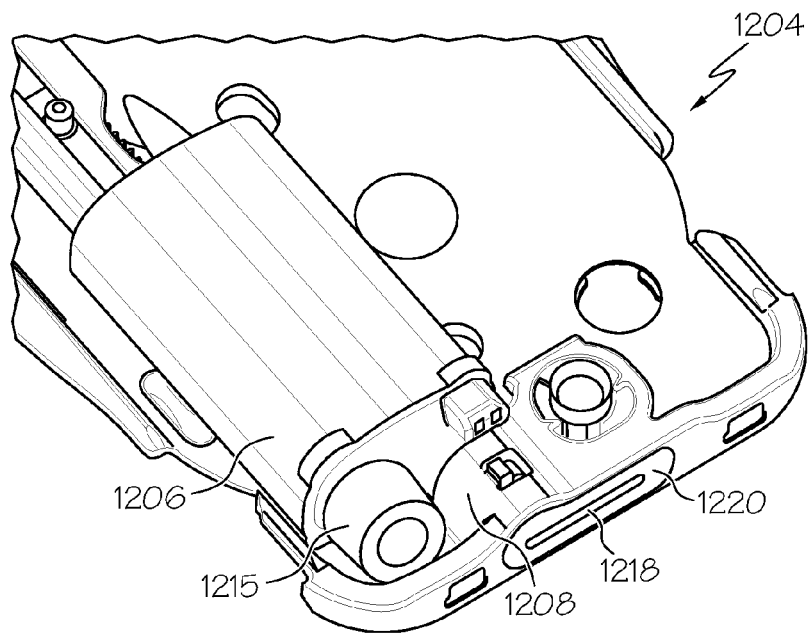
FIG. 19 is a perspective view that depicts internal structure of the base plate of the fluid infusion device shown in FIG. 1.
Figure 20:
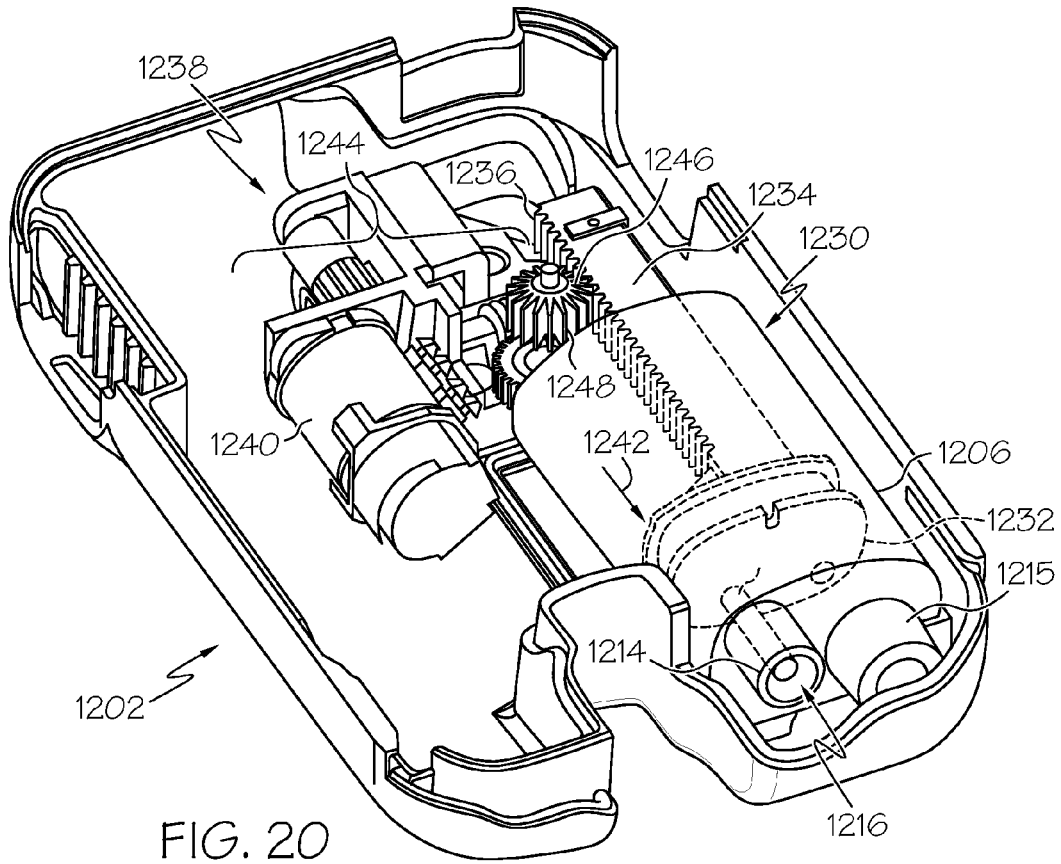
FIG. 20 is a perspective view that depicts internal structure of the durable housing that is normally hidden from view.

FIG. 17 is a perspective view of an exemplary embodiment of a compact patient-worn fluid infusion device 1200. The fluid infusion device 1200 includes two primary components that are removably coupled to each other: a durable housing 1202 and a base plate 1204. The fluid infusion device 1200 also includes or cooperates with a removable/replaceable fluid reservoir 1206. For the illustrated embodiment, the fluid reservoir 1206 mates with, and is received by, the durable housing 1202. In alternate embodiments, the fluid reservoir 1206 mates with, and is received by, the base plate 1204. FIG. 18 is a perspective view that depicts internal structure of the durable housing 1202, FIG. 19 is a perspective view that depicts internal structure of the base plate 1204, and FIG. 20 is a perspective view that depicts internal structure of the durable housing 1202 that is normally hidden from view.

The base plate 1204 is designed to be temporarily adhered to the skin of the patient using, for example, an adhesive layer of material. After the base plate is affixed to the skin of the patient, a suitably configured insertion device or apparatus may be used to insert a fluid delivery needle or cannula 1212 (see FIG. 17) into the body of the patient. The cannula 1212 functions as one part of the fluid delivery path associated with the fluid infusion device 1200, as is well understood.

FIG. 17 depicts the durable housing 1202 and the base plate 1204 coupled together. In practice, the durable housing 1202 and/or the base plate 1204 may include features, structures, or elements to facilitate removable coupling (e.g., pawls, latches, rails, slots, keyways, buttons, or the like). As shown in FIG. 18, the durable housing 1202 is designed to receive the removable fluid reservoir 1206 and to retain the fluid reservoir 1206 in a particular position and orientation. Moreover, the durable housing 1202 is configured to secure to the base plate 1204 in a specified orientation to engage the fluid reservoir 1206 with a reservoir port receptacle 1208 (see FIG. 19) to establish a flow path from the fluid reservoir 1206 to the cannula 1212. For this particular embodiment, the durable housing 1202 contains, among other components, a drive motor assembly, a battery, a drive mechanism for the fluid reservoir 1206, one or more integrated circuit chips and/or other electronic devices (a cover 1213 and/or other structure of the durable housing 1202 normally hides these elements from view, as depicted in FIG. 18). In particular embodiments, the fluid infusion device 1200 includes certain features to orient, align, and position the durable housing 1202 relative to the base plate 1204 such that when the two components are coupled together the fluid reservoir 1206 is urged into the reservoir port receptacle 1208 to engage the sealing assembly and establish a fluid seal.

The durable housing 1202 and the base plate 1204 are cooperatively configured to accommodate removable coupling of the durable housing 1202 to the base plate 1204. The removable nature of the durable housing 1202 enables the patient to replace the fluid reservoir 1206 as needed without having to remove the base plate 1204 and the cannula 1212 from the skin. Moreover, the durable housing 1202 can be removed (while leaving the base plate 1204 adhered to the patient) to allow the patient to swim, shower, bathe, and participate in other activities that might otherwise damage or contaminate the durable housing 1202. When the durable housing 1202 is removed from the base plate 1204, the fluid reservoir 1206 is disengaged from the reservoir port receptacle 1208, the fluid flow path is broken, and the base plate 1204 seals its portion of the fluid flow path that leads to the cannula 1212.

The fluid reservoir 1206 includes a fluid delivery port 1214 that cooperates with the reservoir port receptacle 1208. FIG. 19 depicts the fully installed position of the fluid reservoir 1206 relative to the base plate 1204 and the reservoir port receptacle 1208 (for ease of illustration, the durable housing 1202 is not shown in FIG. 19). For the exemplary embodiment described in detail here, the fluid delivery port 1214 includes include a pierceable septum that is pierced by a hollow needle (which is associated with the reservoir port receptacle 1208) to accommodate delivery of fluid from the fluid reservoir 1206. The fluid reservoir 1206 may also include a fill port 1215 that accommodates filling of the fluid reservoir 1206 by the patient, a doctor, a caregiver, or the like.

The fluid delivery port 1214 has an interior 1216 defined therein that is shaped, sized, and otherwise configured to receive a sealing element when the fluid reservoir 1206 is engaged with the reservoir port receptacle 1208. The sealing element forms part of a sealing assembly for the fluid infusion device 1200. In this regard, the sealing assembly includes one or more sealing elements and/or fluid delivery needles configured to establish fluid communication from the interior of the fluid reservoir 1206 to the cannula 1212 via the fluid delivery port 1214 and a conduit 1218 located in a mounting cap 1220, and thereby establish a fluid delivery path from the fluid reservoir 1206 to the user via the cannula 1212.

FIG. 20 is a perspective view of the durable housing 1202 with the cover 1213 removed. FIG. 20 also depicts the fluid reservoir 1206 in a simplified manner that facilitates a better understanding of the internal structure of the fluid reservoir 1206. As illustrated in FIG. 20, the fluid reservoir 1206 includes a reservoir barrel 1230 that contains the fluid and a plunger 1232 (or stopper) positioned to push fluid from inside the barrel 1230 of the fluid reservoir 1206 along the fluid path through the cannula 1212 to the user. The plunger 1232 includes a shaft 1234 coupled thereto or integrated therewith. The shaft 1234 has exposed teeth 1236 that are configured to mechanically couple or otherwise engage with a drive system 1238 contained in the durable housing 1202. In exemplary embodiments, the drive system 1238 includes a drive motor assembly 1240 having a rotor that is mechanically coupled to an actuation mechanism that translates rotation of the rotor of the drive motor assembly 1240 to translational displacement of the plunger 1232 in the direction 1242 of the fluid delivery port 1214 (or in the opposite direction during rewind operations). The actuation mechanism can be implemented as a gear assembly, linkage, or any suitable arrangement of components operatively coupled to the drive motor assembly 1240 for purposes of actuation of the plunger 1232. In this regard, in exemplary embodiments, the rotor of the motor assembly 1240 is mechanically coupled to a rotary shaft, which, in turn, engages a gear assembly 1244 that includes a pinion gear 1246 having exposed teeth 1248 configured to mate with or otherwise engage the teeth 1236 of the shaft 1234. The rotary shaft translates rotation (or displacement) of the rotor of the motor assembly 1240 into a corresponding rotation (or displacement) of the gear assembly 1244 such that the exposed teeth 1248 of the pinion gear 1246 apply force to the exposed teeth 1236 of the shaft 1234 in the direction 1242. This action, in turn, displaces the plunger 1232 in the direction 1242 of the fluid delivery port 1214 to dispense, expel, or otherwise deliver fluid from the barrel 1230 of the fluid reservoir 1206 to the user via the fluid delivery path provided by the cannula 1212. In exemplary embodiments, the motor assembly 1240 employs a DC motor, such as a stepper motor or brushless DC motor capable of precisely controlling the amount of displacement of the plunger 1232 during operation of the fluid infusion device 1200, as described in greater detail below.

Although some components are hidden from view in FIG. 20, the gear assembly 1244 may include any number of cooperating drive shafts, gears, pinions, racks, and/or other elements that interact to translate the rotational movement of the rotor of the motor assembly 1240 into corresponding rotation of the pinion gear 1246. In exemplary embodiments, the gear assembly 1244 may include various additional gears and other drive train components (e.g., screws, cams, ratchets, jacks, pulleys, pawls, clamps, nuts, slides, bearings, levers, beams, stoppers, plungers, sliders, brackets, guides, bearings, supports, bellows, caps, diaphragms, bags, heaters, and the like) configured to control the displacement of the shaft 1234.

Figure 21:
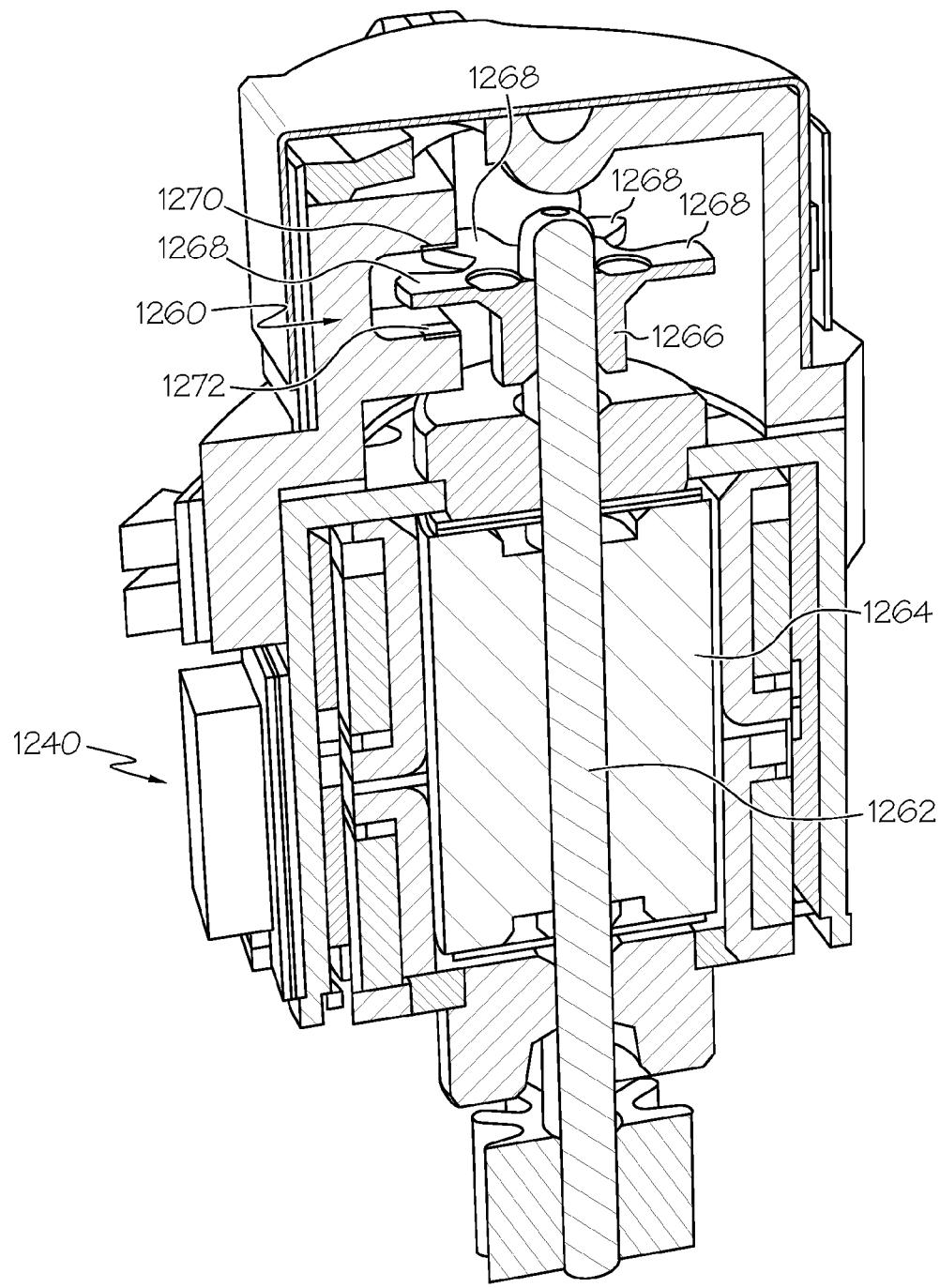
FIG. 21 is a cross-sectional perspective view of a motor assembly suitable for use with the durable housing portion.

FIG. 21 is a cross-sectional perspective view of the motor assembly 1240, as viewed along its major longitudinal axis. In an exemplary embodiment, a sensor 1260 is configured to measure, sense, or otherwise detect rotation (or displacement) of a rotary shaft 1262 and/or a rotor 1264 of the motor assembly 1240. In this regard, the rotary shaft 1262 may include a detectable feature that is measurable or otherwise detectable by the sensor 1260. For example, a rotary member (or wheel) 1266 can be provided on the rotary shaft 1262, wherein the wheel 1266 includes a plurality of protruding features (or arms) 1268 that are measurable or otherwise detectable by the sensor 1260. In the illustrated embodiment, the wheel 1266 is coaxial and/or concentric to and disposed about the rotary shaft 1262, and the wheel 1266 is affixed to or otherwise integrated with the rotary shaft 1262 such that the wheel 1266 and the rotary shaft 1262 rotate in unison. In this manner, rotation (or displacement) of the wheel 1266 corresponds to the displacement of the rotary shaft 1262 and/or the rotor 1264 of the motor assembly 1240.

In certain embodiments, the sensor 1260 is realized as an incremental position sensor configured to measure, sense, or otherwise detect incremental rotations of the rotary shaft 1262 and/or the rotor 1264. For example, in accordance with one or more embodiments, the sensor 1260 is realized as a rotary encoder. In alternative embodiments, the sensor 1260 may be realized using any other suitable sensor, such as (but not limited to) a magnetic sensor, optical sensor (or other light detector), tactile sensor, capacitive sensor, inductive sensor, and/or the like. In exemplary embodiments, an incremental position sensor 1260 may be configured to count or otherwise sense incremental rotations of the motor assembly 1240 via the wheel 1266, for example, by counting each time a protruding feature 1268 passes by the sensor 1260. In this regard, when the number of protruding features 1268 equals or otherwise corresponds to the number of discrete motor steps of the drive motor assembly 1240, the incremental position sensor 1260 counts or otherwise senses the number of motor steps traversed by the rotary shaft 1262 and/or the rotor 1264. In some embodiments, the sensor 1260 includes an emitter 1270 and a detector 1272 disposed on opposite sides of the wheel 1266 such that at least a portion of the protruding features 1268 passes between the emitter 1270 and the detector 1272 as the wheel 1266 rotates. In this regard, the sensor 1260 may detect or otherwise count each instance when a protruding feature 1268 interrupts a transmission from the emitter 1270 to the detector 1272. Alternatively, the sensor 1260 may detect or otherwise count each instance a transmission from the emitter 1270 to the detector 1272 is uninterrupted or otherwise completed (e.g., via gaps between the protruding features 1268).

Figure 22:
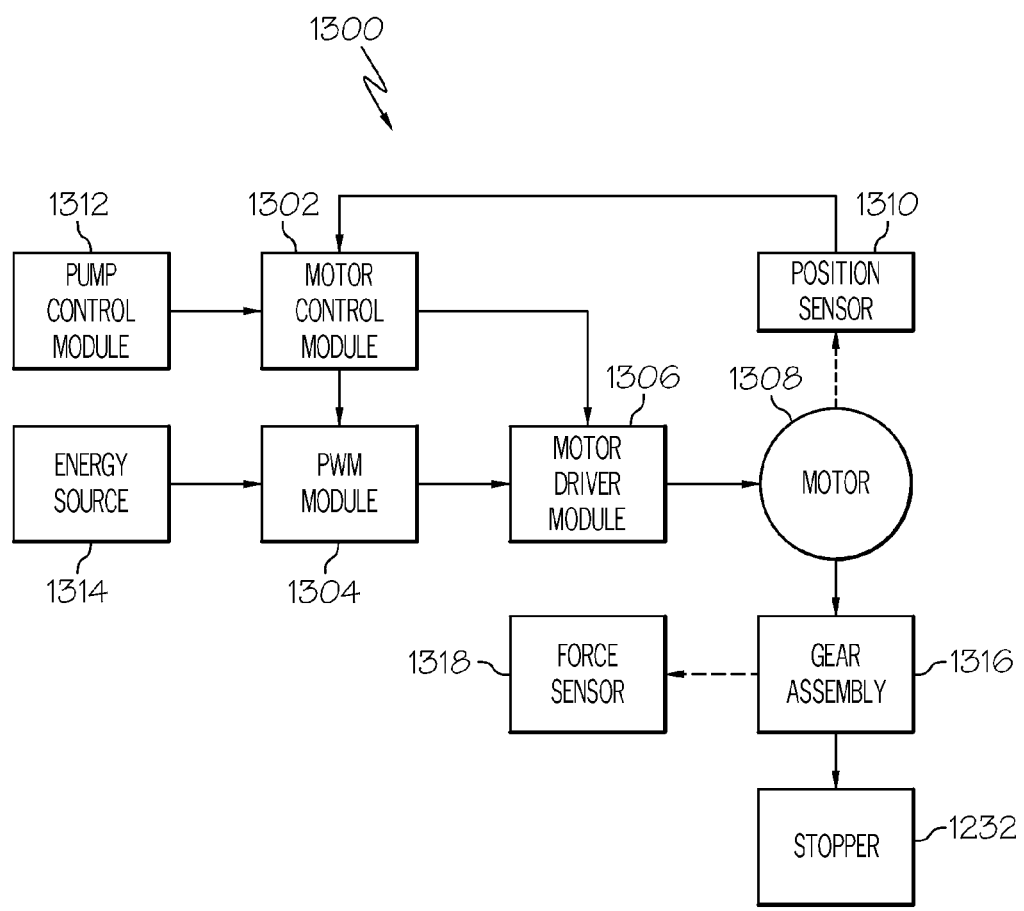
FIG. 22 is a schematic representation of an exemplary control system suitable for use in a fluid infusion device such as that depicted in FIGS. 17-20.

The fluid infusion device 1200 is suitably configured to carry out a reservoir seating and conditioning routine that prepares the fluid reservoir 1206 for fluid coupling to the base plate 1204. This routine (along with other processes associated with the operation of the fluid infusion device 1200) can be carried out using the onboard processing capability of the fluid infusion device 1200. For the embodiment described here, the intelligence and processing capability of the fluid infusion device 1200 is incorporated into the durable housing 1202. Although not shown in FIGS. 17-20, the durable housing 1202 includes appropriate electronics, memory, logic, and computer executable code that are configured to carry out the various functions and operations described in more detail here. For example, the durable housing 1202 may include some or all of the elements and features described above with reference to FIG. 4 (such as a memory, an electronics and processor module, a force sensor, relevant hardware, software, and applications, etc.) In this regard, FIG. 22 is a schematic representation of an exemplary control system 1300 suitable for use in the fluid infusion device 1200.

The illustrated control system 1300 includes, without limitation: a motor control module 1302; a pulse-width modulation (PWM) module 1304; a motor driver module 1306; a motor 1308 (which is part of the motor assembly 1240 shown in FIG. 20); a position sensor 1310 (e.g., the sensor 1260 depicted in FIG. 21); a pump control module 1312; an energy source 1314; a gear assembly 1316 (e.g., the gear assembly 1244 depicted in FIG. 20); and a force sensor 1318. The processing and control modules of the control system 1300 could be implemented using at least one processor, such as the electronics module 162 depicted in FIG. 4. The control system 1300 operates the motor 1308 in response to a dosage command (which is indicative of a desired amount of fluid to be delivered) that is received from the pump control module 1312. In this regard, the pump control module 1312 generally represents the electronics and other components of the fluid infusion device that are responsible for regulating the amount of fluid delivered to the patient. It should be understood that FIG. 22 is a simplified representation of the control system 1300 that is suitable for purposes of explanation, and that FIG. 22 is not intended to limit the subject matter described herein in any way. For example, in practice, the features and/or functionality of the motor control module 1302 may implemented by or otherwise integrated into the pump control module 1312, or vice versa.

In the illustrated embodiment, the PWM module 1304 generally represents the combination of circuitry, hardware and/or other electrical components configured to generate a pulse-width modulated voltage output applied to the motor 1308 via the motor driver module 1306. In an exemplary embodiment, the PWM module 1304 is coupled to the energy source 1314, such as a battery housed within the fluid infusion device (e.g., in the durable housing 1202), to receive a supply voltage. The PWM module 1304 reacts to a duty cycle setting to generate or otherwise produce a pulse-width modulated voltage output that oscillates between the supply voltage provided by the energy source 1314 and a ground (or reference) voltage over a time interval (e.g., the PWM period), wherein the pulse-width modulated voltage output is equal to the supply voltage for a percentage of the time interval corresponding to the duty cycle setting. For example, if the supply voltage provided by the energy source 1314 is equal to five volts and the duty cycle setting is equal to thirty percent, then the pulse-width modulated voltage output generated by the PWM module 1304 may be a square wave having a magnitude equal to five volts for thirty percent of the time interval and zero volts for the remaining seventy percent of the time interval. In this regard, the duty cycle setting corresponds to the width of a portion of the square wave (e.g., the portion corresponding the supply voltage), and accordingly, the duty cycle setting may alternatively be referred to herein as the PWM width setting. In an exemplary embodiment, the frequency of the pulse-width modulated voltage output (e.g., the inverse of the PWM period) is greater than the frequency of the motor driver module 1306, and the frequency of the pulse-width modulated voltage output is typically greater than the electrical time constant of the motor coils. In exemplary embodiments, the PWM module 1304 is coupled to the motor control module 1302 which is configured to adjust, modify, or otherwise control the duty cycle setting of the PWM module 1304.

In an exemplary embodiment, the motor 1308 is a stepper motor or brushless DC motor having a toothed rotor and a number of sets of windings, wherein the number of teeth on the rotor along with the number of winding sets and the physical arrangement of the winding sets with respect to the rotor teeth provides a finite number of motor steps within a revolution of the rotor. In this regard, as used herein, a "motor step" or any variant thereof should be understood as referring to an incremental rotation of the rotor of the motor 1308 that is dictated by the number of teeth of the rotor along with the number and/or arrangement of the winding sets. The rotor of the motor 1308 is mechanically coupled to the gear assembly 1316 such that an incremental rotation of the rotor by one motor step produces a corresponding amount of displacement of the plunger 1232 (see FIG. 20).

The motor driver module 1306 generally represents the combination of circuitry, hardware and/or other electrical components configured to sequentially apply a voltage provided at a supply voltage input of the motor driver module 1306 to one or more sets of windings of the motor 1308 in a particular order to produce a corresponding number of commanded motor steps of rotation by the motor 1308. In the illustrated embodiment, the supply voltage input of the motor driver module 1306 is coupled to the output of the PWM module 1304, such that the motor driver module 1306 provides the pulse-width modulated voltage from the PWM module 1304 to the one or more sets of windings of the motor 1308 in a particular order under control of the motor control module 1302. In this regard, in some embodiments, the motor driver module 1306 is coupled to the motor control module 1302 to receive a commanded number of motor steps from the motor control module 1302, wherein in response to the commanded number of motor steps, the motor driver module 1306 sequentially applies the pulse-width modulated voltage from the PWM module 1304 to the sets of windings of the motor 1308 in the appropriate order to produce the commanded number of motor steps. In other embodiments, the motor control module 1302 may operate the switches and/or other circuitry of the motor driver module 1306 to produce the commanded number of motor steps. The frequency at which the motor driver module 1306 is operated (e.g., the frequency at which the pulse-width modulated voltage is changed from being applied to one winding set to another winding set) is less than the frequency of the pulse-width modulated voltage output from the PWM module 1304, such that the pulse-width modulated voltage output oscillates between the supply voltage and the ground voltage multiple times over the time period (e.g., the inverse of the motor driver frequency) during which the pulse-width modulated voltage output is applied to a particular set of windings of the motor 1308.

The position sensor 1310 can be realized as an incremental position sensor, such as a rotary encoder, that is configured to sense, measure, or otherwise detect an incremental rotation of the rotor of the motor 1308, in a similar manner as described above in the context of FIG. 21. In exemplary embodiments, the resolution of the position sensor 1310 is greater than or equal to the resolution of the motor 1308, that is, the number of discrete incremental rotations measurable by the position sensor 1310 over one revolution of the rotor of the motor 1308 (e.g., the number of detectable protruding features 1268 shown in FIG. 21) is greater than or equal to the number of discrete motor steps over one revolution of the rotor of the motor 1308. The output of the position sensor 1310 is coupled to the motor control module 1302 to provide dynamic closed-loop PWM control of the motor 1308, as described in greater detail below.

Still referring to FIG. 22, the motor control module 1302 generally represents the hardware, software, firmware and/or combination thereof that is configured to receive or otherwise obtain a commanded dosage from the pump control module 1312, convert the commanded dosage to a commanded number of motor steps, and command, signal, or otherwise operate the motor driver module 1306 to cause the motor 1308 to produce the commanded number of motor steps. Similarly, the motor control module 1302 is responsible for controlling various forward drive commands and reverse (rewind) commands as needed to support the reservoir seating procedure described in more detail below. In practice, the motor control module 1302 modifies or otherwise adjusts the PWM width setting of the PWM module 1304 and/or the pulse per second (PPS) setting of the motor driver module 1306 as needed during the reservoir seating procedure and, if so desired, during normal delivery operations. Depending on the embodiment, the motor control module 1302 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 1302, or in any practical combination thereof. In exemplary embodiments, the motor control module 1302 includes or otherwise accesses a memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 1302. The computer-executable programming instructions, when read and executed by the motor control module 1302, cause the motor control module 1302 to perform the tasks, operations, functions, and processes described in greater detail below.

In certain embodiments, the force sensor 1318 is operatively coupled to the actuation mechanism (e.g., coupled to the gear assembly 1316 and/or to the motor 1308). The force sensor 1318 may be generally configured to function substantially as described above for the force sensor 126. However, rather than directly measure an axially applied load, the force sensor 1318 indirectly detects axial force associated with the shaft 1234, where such axial force is transferred to the pinion gear 1246 and, in turn, to one or more other components of the gear assembly 1244. Consequently, the force sensor 1318 may be coupled to one or more components of the gear assembly 1244 for purposes of obtaining certain measures of force that correspond to an axial load of the shaft 1234. In other words, the force sensor can be used to measure, detect, or otherwise obtain (either directly or indirectly by calculation) forces associated with interaction of the shaft 1234 with the actuation mechanism of the fluid infusion device 1200. In practice, internal pressure of the fluid reservoir 1206 can influence the amount of force detected by the force sensor 1318.

Components located in the durable housing 1202 of the fluid infusion device 1200 cooperate to confirm seating of the fluid reservoir 1206 when needed. The fluid reservoir 1206 is filled (typically by the patient or a caregiver) and sealed before it is installed into the durable housing 1202. After the fluid infusion device 1200 confirms that the fluid reservoir 1206 is properly seated, the durable housing 1202 can be coupled to the base plate 1204 (which is already affixed to the patient with the cannula 1212 subcutaneously in place). When the durable housing 1202 is coupled to the base plate 1204, a flow path is created from the fluid reservoir 1206 to the cannula 1212. Ideally, the fluid reservoir 1206 will have no internal pressure after the seating procedure; this condition is important to reduce the likelihood of unintentional fluid delivery upon coupling the durable housing 1202 to the base plate 1204.

In a traditional fluid infusion system having an open flow path that is defined prior to insertion into the skin, the user can visually confirm seating and priming of the flow path by actuating the drive mechanism until fluid is discharged from the end of the needle or cannula (this occurs before the infusion set is inserted into the skin of the patient). In contrast, the fluid infusion device 1200 has a closed fluid path at the time of reservoir installation and seating. Consequently, the reservoir seating process for the fluid infusion device 1200 is carried out in an automated fashion and without relying on any user feedback. Moreover, the seating process should prepare the fluid reservoir for predicable and calibrated fluid delivery as soon as the durable housing 1202 is coupled to the base plate 1204. In other words, the seating process should remove any compliance and "slack" associated with the fluid reservoir and/or the drive system in the durable housing 1202.

Figure 23:
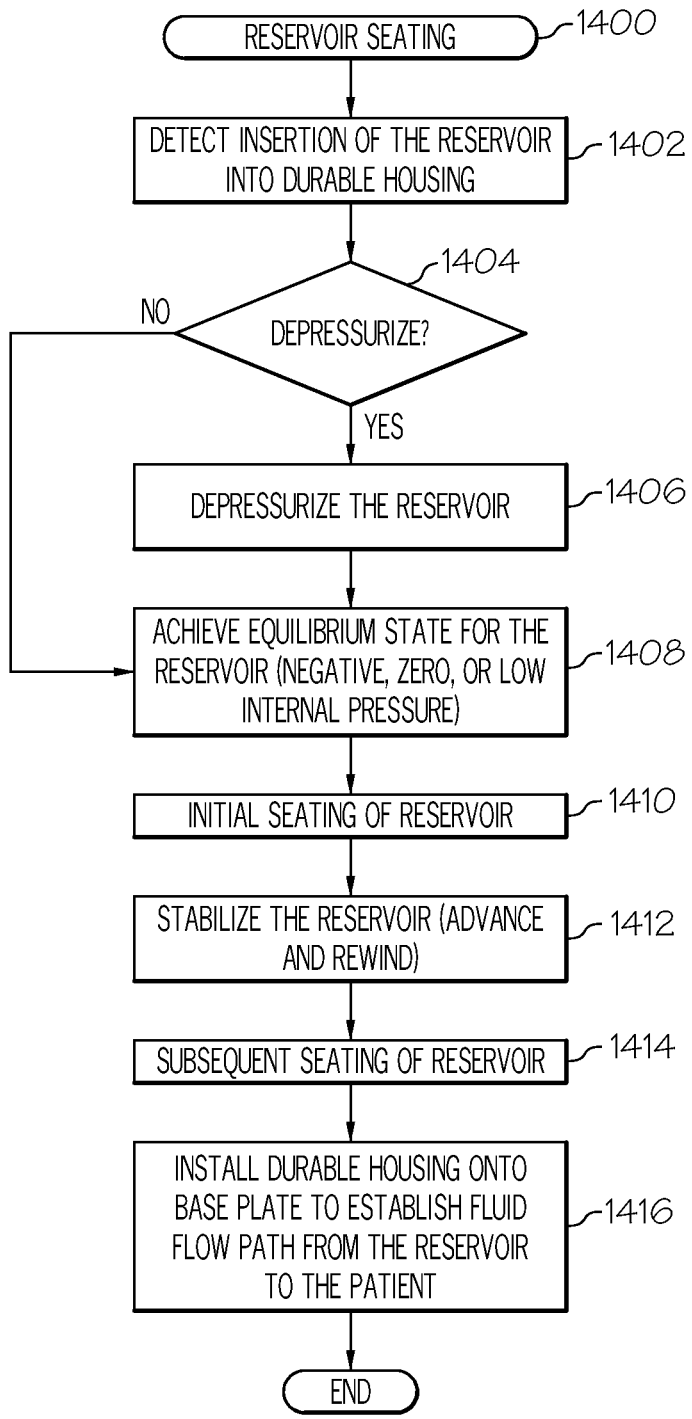
FIG. 23 is a flow chart that illustrates an exemplary embodiment of a reservoir seating process.

In certain embodiments, the control system 1300 is utilized to carry out a reservoir seating process that prepares the fluid reservoir 1206 for introduction into the fluid delivery path. In this regard, FIG. 23 is a flow chart that illustrates an exemplary embodiment of a reservoir seating process 1400 that is suitable for use with a device such as the fluid infusion device 1200. As mentioned above, the process 1400 is performed prior to establishing an outgoing fluid flow path from the fluid reservoir to the fluid delivery path of the patient. Thus, the process 1400 is performed while the fluid reservoir remains sealed and without an open fluid flow path to allow the fluid to escape.

The process 1400 begins by detecting the insertion of the fluid reservoir into the durable housing (task 1402). The process 1400 assumes that reservoir seating is necessary or desirable whenever a new or refilled fluid reservoir is installed into the durable housing. Presence of the fluid reservoir can be detected by any suitable technique or technology, such as a capacitive or resistive sensor, a switch, an optical sensor, or the like. In certain embodiments, presence of the fluid reservoir is indicated by the user. In this regard, the user could indicate presence of the reservoir by pressing a button on the infusion device or on a controller device, such that detection of the button press initiates the seating procedure. For the illustrated embodiment, insertion of the fluid reservoir causes the shaft 1234 of the plunger 1232 to engage one or more elements of the actuation mechanism (e.g., the pinion gear 1246).

In response to the detection of the fluid reservoir, the process 1400 continues by determining whether the fluid reservoir is in need of depressurization (query task 1404). Depressurization may be needed if the reservoir is pressurized during the filling/refilling procedure. If the process 1400 determines that depressurization is not required (the "No" branch of query task 1404), then the process may lead to a task 1408. If, however, depressurization is needed (the "Yes" branch of query task 1404), then the process 1400 performs one or more operations to depressurize the fluid reservoir (task 1406). As described in more detail below with reference to FIG. 24, a depressurization operation can be performed by rewinding the drive motor assembly by some controlled amount.

After depressurizing the fluid reservoir, the process 1400 continues by performing one or more operations to achieve an equilibrium state for the fluid reservoir (task 1408). Task 1408 is also performed when query task 1404 determines that depressurization is not necessary. The equilibrium state achieved during task 1408 corresponds to a specified force/pressure condition associated with the fluid reservoir. For example, to reduce the likelihood of unintended fluid delivery when the durable housing is coupled to the base plate, task 1408 can be performed to establish any desired pressure or force condition, such as a zero force condition, or a low positive pressure condition for the fluid reservoir. As described in more detail below with reference to FIG. 25, the drive motor assembly can be incrementally rewound by some controlled amount to achieve the desired equilibrium state. Upon completion of task 1408, therefore, the process 1400 obtains a known reference point (e.g., a force or pressure measure).

After achieving the equilibrium state, the process 1400 continues by performing one or more operations to obtain an initial seated state for the fluid reservoir (task 1410). Initial seating of the reservoir may be performed by advancing the drive motor assembly by some controlled amount, as described in more detail below. The illustrated embodiment of the process 1400 continues by performing a stabilizing cycle with the drive motor assembly to stabilize the fluid reservoir (task 1412). The stabilizing cycle is intended to overcome any transient delivery period following the initial seating, and to remove the compliance of the drive system. In practice, the stabilizing cycle is carried out by advancing the drive motor assembly by a first controlled amount, and thereafter rewinding the drive motor assembly by a second controlled amount. This action pressurizes and immediately depressurizes the fluid reservoir, which prepares the fluid infusion device for steady state delivery. It should be appreciated that any number of pressurize/depressurize cycles can be performed during task 1412.

After completing the stabilizing cycle, the process 1400 continues by performing one or more operations to obtain a subsequent seated state for the fluid reservoir (task 1414). This subsequent seating routine may be performed by advancing the drive motor assembly by a controlled amount. In certain implementations, the subsequent seated state is identical to the initial seated state. In other words, the stabilizing cycle is performed to "pulse" the fluid reservoir, but the system returns to the same initial seated state after completing the stabilizing cycle. After obtaining the subsequent seated state, the durable housing may be coupled to the base plate to establish the fluid flow path from the fluid reservoir to the fluid delivery path in the base plate (task 1416). As a result of this action, the fluid reservoir becomes fluidly coupled to the fluid delivery conduit (e.g., a cannula or a delivery needle) to facilitate delivery of the medication fluid from the reservoir to the user.

It should be appreciated that tasks 1412 and 1414 are optional, and that an embodiment of the process 1400 may terminate the seating procedure after achieving the initial seated state at task 1410. In such an alternative embodiment, task 1416 can immediately follow task 1410.

FIGS. 24-28 are flow charts that illustrate different stages of an exemplary embodiment of a reservoir seating process 1500. The process 1500 is consistent with the process 1400 described previously. Indeed, the process 1500 represents one particular implementation of the process 1400. For ease of illustration, the process 1500 is illustrated in five different stages, which generally correspond to the following: (1) depressurization; (2) equalization; (3) initial seating; (4) stabilization; and (5) subsequent seating.

Figure 24:
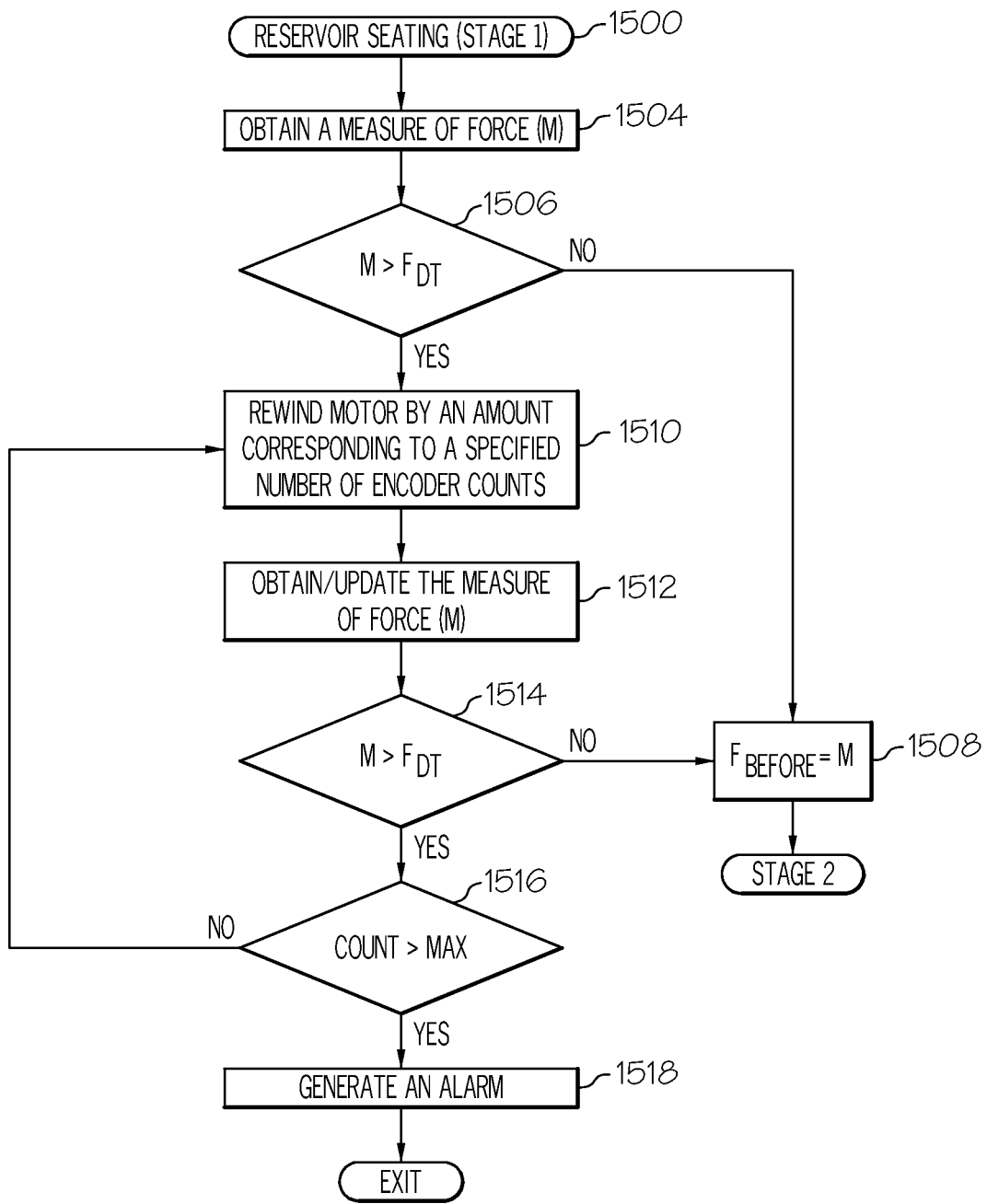
FIGS. 24-28 are flow charts that illustrate different stages of an exemplary embodiment of a reservoir seating process.

This description assumes that the process 1500 has already detected the insertion of the fluid reservoir into the durable housing. Referring to FIG. 24, the illustrated embodiment of the process 1500 begins by obtaining a measure of force (M) using the force sensor (task 1504). As explained above, this measure of force is associated with interaction of the plunger shaft with the actuation mechanism of the durable housing. More specifically, this measure of force is indicative of an amount of force imparted by the shaft 1234 to the pinion gear 1246. The measure of force may be based on a single force reading, or it may be based on a plurality of different force readings (e.g., an average of collected force readings, a maximum value, a minimum value, or the like). In one exemplary embodiment, task 1504 calculates each value of M as an average of sixteen force sensor readings taken within a very short period of time at a predetermined sampling rate such as 1.0 kHz. These force sensor readings represent static measurements because they are taken without actuating the drive motor assembly. The individual force readings, along with the calculated average for M, are saved for future reference.

Next, the process 1500 determines whether the fluid reservoir is in need of depressurization by comparing the measure of force M to a depressurization threshold force value, $F_{DT}$ (query task 1506). The specific value of $F_{DT}$ may vary from one embodiment to another; the value of $F_{DT}$ is chosen such that it accurately indicates whether or not the fluid reservoir contains an undesirable amount of internal pressure. In certain embodiments, the value of $F_{DT}$ is designated to be about 0.06 pounds. If the measure of force M does not exceed $F_{DT}$ (the "No" branch of query task 1506), then the process 1500 skips the depressurization operation and proceeds to a task 1508, which assigns the current value of M to a variable $F_{BEFORE}$, which is utilized during the second stage of the process 1500 (see FIG. 25).

If query task 1506 determines that the measure of force M is greater than the depressurization threshold force value $F_{DT}$, the process 1500 continues in an attempt to depressurize the fluid reservoir. In practice, the process depressurizes the fluid reservoir by rewinding the drive motor assembly by a controlled rewind amount until the measure of force is less than or equal to $F_{DT}$. For this particular embodiment, the process 1500 rewinds the drive motor assembly by a predetermined amount that corresponds to a specified number of encoder counts (task 1510), and then obtains an updated measure of the force M (task 1512). As used here, an "encoder count" or "count" is associated with a measure of actuation or rotation of the motor used in the drive motor assembly. In this regard, references to "encoder count" and "count" in the context of the process 1500 are consistent with the definitions and meanings provided above with reference to FIGS. 20-22.

The force may be monitored on a continuous basis such that a measure of force is obtained after each encoder count. Accordingly, after rewinding the drive motor assembly by the predetermined amount, the updated measure of the force M represents an individual force reading (rather than an average of multiple readings). For this particular embodiment, the rewinding that occurs during task 1510 is performed in a controlled manner with specified motor control parameters. In particular, the rewinding during task 1510 is performed at a specified pulse per second setting (RewPPS) and at a specified pulse-width modulation duty cycle (RewPWM). In certain embodiments, the nominal value of RewPPS may be about 1,000 PPS and the nominal value of RewPWM may be about 70% (this nominal value is desirable to conserve battery power). It should be appreciated that an embodiment may utilize different values for these settings, and that the exemplary nominal values provided here are not intended to restrict the scope or application of the process 1500.

If the current measure of force M is less than or equal to the depressurization threshold force value $F_{DT}$ (query task 1514), then the process 1500 considers the fluid reservoir to be depressurized, and the process 1500 leads to task 1508. Task 1508 assigns the current value of M to the variable $F_{BEFORE}$, which is used during the second stage of the process 1500 (see FIG. 25). If the current measure of force M remains greater than $F_{DT}$, the process 1500 checks whether the total number of rewind encoder counts (associated with execution of task 1510) exceeds a maximum allowable count (query task 1516). In other words, the process determines whether a total amount of rewinding performed while depressurizing the fluid reservoir exceeds a maximum allowable rewind amount. If query task 1516 determines that the maximum count has been exceeded, then an appropriate alarm is generated (task 1518) and the process 1500 exits. Although the maximum count used for query task 1516 may vary from one embodiment to another, the exemplary implementation described here employs a maximum count of 1,650. Consequently, if the depressurization threshold force value $F_{DT}$ is not reached within 1,650 encoder counts, the alarm is generated.

If the maximum encoder count has not been exceeded (the "No" branch of query task 1516), then the process 1500 repeats tasks 1510, 1512, and 1514, as depicted in FIG. 24. Thus, the drive motor assembly is rewound in an incremental fashion, while comparing the current measure of force M to $F_{DT}$ at each iteration. This loop will be repeated until the updated measure of force M is less than or equal to $F_{DT}$, or until the maximum encoder count is exceeded at query task 1516.

If the depressurization routine is successful, the current measure of force M can be used as the initial value of $F_{BEFORE}$. In practice, the variable of $F_{BEFORE}$ may correspond to a digital representation of an analog force measure. Accordingly, the measure of force M can be converted into a digital representation having any desired number of bits. For simplicity and ease of description, task 1508 and the following description of the second stage of the process 1500 refer to $F_{BEFORE}$ in a general sense without regard to whether $F_{BEFORE}$ represents an analog or a digital quantity. In certain practical embodiments, rather than leveraging the current value of M, the initial value of $F_{BEFORE}$ may be calculated as an average of multiple force sensor readings taken immediately after the fluid reservoir has been depressurized.

Figure 25:
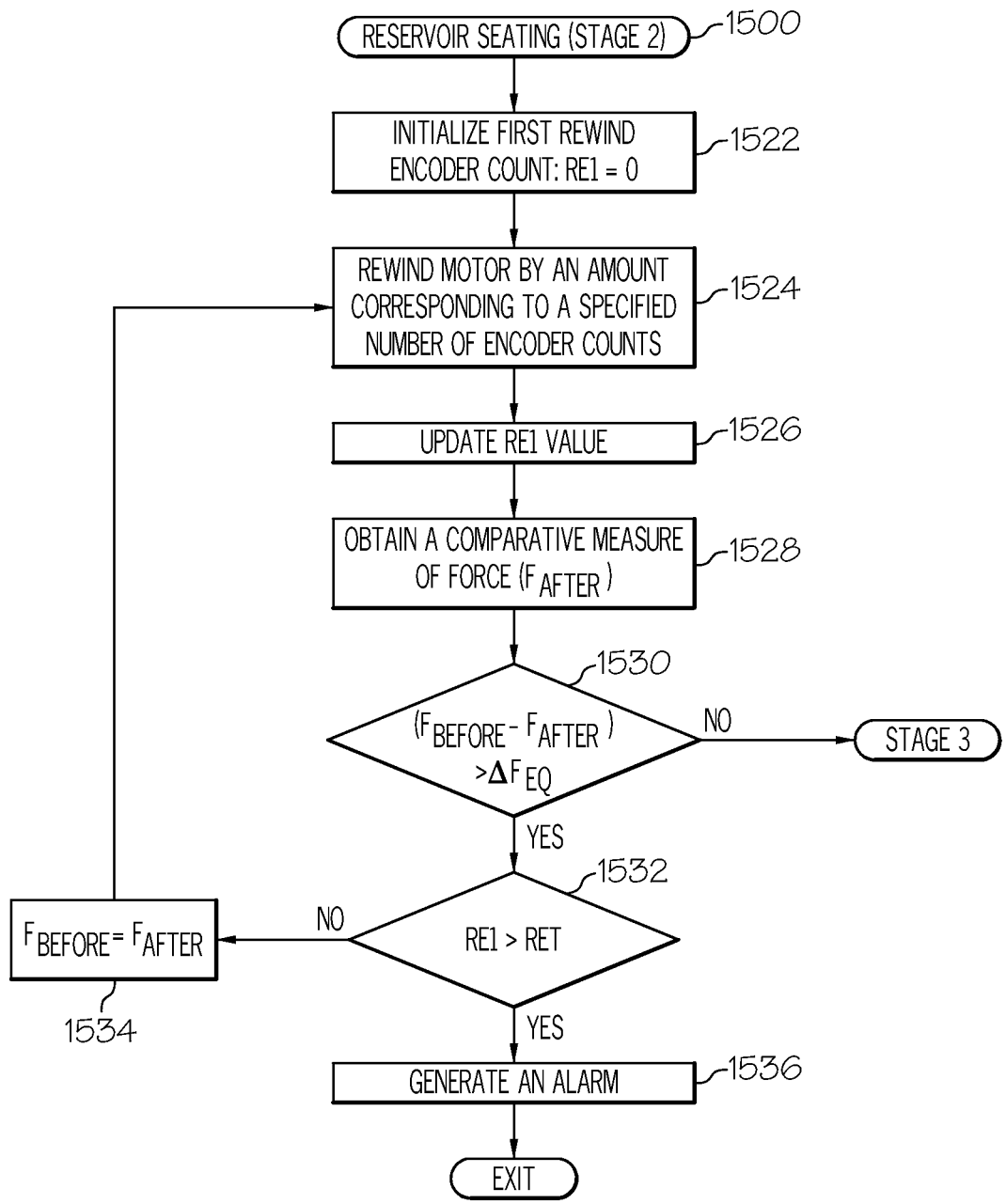

Referring now to FIG. 25, the second stage of the process 1500 is performed in an attempt to find a suitable pressure/force equilibrium point for the fluid reservoir. The second stage is performed after the fluid reservoir has been depressurized (if needed), and the second stage utilizes the value of $F_{BEFORE}$ obtained during the first stage of the process 1500. In connection with the second stage, the illustrated embodiment of the process 1500 initializes a first rewind encoder count (task 1522). For this example, the first rewind encoder count is represented by the variable RE1, and task 1522 resets RE1 to a value of zero. Accordingly, initializing RE1 provides a reference encoder count for purposes of rewind operations that may occur during the process 1500, as described in more detail below.

The illustrated embodiment continues with the equalizing procedure by rewinding the drive motor assembly by a controlled rewind amount that corresponds to a predetermined number of encoder counts (task 1524). Although the specific number of encoder counts utilized during task 1524 may vary from one embodiment to another, and may vary from one iteration of task 1524 to another, the exemplary embodiment described here employs a constant rewind encoder count of 24 during task 1524. Consequently, the drive motor assembly is rewound by 24 encoder counts during each iteration of task 1524. For this particular embodiment, the rewinding that occurs during task 1524 is performed in a controlled manner with specified motor control parameters. For example, the rewinding during task 1524 may be performed using the same pulse per second setting (RewPPS) and the same pulse-width modulation duty cycle (RewPWM) used during the depressurization procedure.

Following task 1524, the process 1500 performs a task 1526 to update the value of RE1, which is the first rewind encoder count initialized at task 1522. The value of RE1 is updated by adding the number of rewind encoder counts associated with the immediately preceding iteration of task 1524 (i.e., 24 encoder counts for this particular example) to the current value of RE1. Thus, RE1 represents an ongoing accumulated count that represents the total amount that the drive motor assembly has rewound during the equilibrium procedure.

The process 1500 continues by obtaining a subsequent comparative measure of force ($F_{AFTER}$) using the force sensor (task 1528). The subsequent comparative measure of force may be based on a single force reading, or it may be based on a plurality of different force readings (e.g., an average of collected force readings, a maximum value, a minimum value, or the like). In one exemplary embodiment, task 1528 calculates the value of $F_{AFTER}$ as an average of sixteen force sensor readings taken within a very short period of time at a predetermined sampling rate such as 1.0 kHz. These force sensor readings represent static measurements because they are taken without actuating the drive motor assembly. As described above with reference to the value of $F_{BEFORE}$, the value of $F_{AFTER}$ may correspond to a digital representation of an analog force measure. This allows of $F_{AFTER}$ to be easily compared to $F_{BEFORE}$. For simplicity and ease of description, task 1528 and the following description of the second stage of the process 1500 refer to $F_{AFTER}$ in a general sense without regard to whether $F_{AFTER}$ represents an analog or a digital quantity.

The value of $F_{BEFORE}$ obtained during the first stage of the process 1500 represents an initial comparative measure of force for purposes of the second stage of the process 1500. In this regard, the process 1500 continues by calculating a difference between the current values of $F_{BEFORE}$ and $F_{AFTER}$, and compares the difference to a suitable equilibrium threshold value, which represents a difference ($\Delta F_{EQ}$). Query task 1530 represents an exemplary implementation of this comparison. Thus, query task 1530 determines whether $(F_{BEFORE} - F_{AFTER}) > \Delta F_{EQ}$. In one practical implementation, $\Delta F_{EQ}$ corresponds to a digital value that is indicative of a threshold difference in force that small enough to represent the desired equilibrium condition. For the practical example described here, $\Delta F_{EQ}$ is expressed as a number of encoder counts (to provide good measurement accuracy). In this regard, the value of $\Delta F_{EQ}$ may be within the range of about five to ten encoder counts.

If the difference calculated during query task 1530 does not exceed the equilibrium threshold value (the "No" branch of query task 1530), then the process 1500 proceeds to its third stage. The third stage is described below with reference to FIG. 26. Notably, the "No" branch of query task 1530 is followed after the process 1500 has confirmed that the fluid reservoir has reached a predetermined reference state, such as a zero force point.

If query task 1530 determines that the difference is greater than $F_{EQ}$, then the process 1500 assumes that the fluid reservoir has not reached an equilibrium condition. The illustrated embodiment of the process 1500 checks whether the current value of RE1 exceeds a maximum allowable count (query task 1532); this maximum allowable count represents a rewind encoder threshold (RET). Thus, the process 1500 determines whether a total amount of rewinding performed while attempting to achieve the equilibrium state exceeds a maximum allowable rewind amount. If query task 1532 determines that RE1 is greater than RET, then an appropriate alarm is generated (task 1534) and the process 1500 exits. Although the maximum count used for query task 1532 may vary from one embodiment to another, the exemplary implementation described here employs a value of 240 for RET. Consequently, if the equilibrium threshold value $F_{EQ}$ is not reached within 240 rewind encoder counts, the alarm is generated.

If the maximum rewind encoder count RET has not been exceeded (the "No" branch of query task 1532), then the process 1500 updates the value of $F_{BEFORE}$ (task 1534). More specifically, the current value of $F_{AFTER}$ is assigned as the new value of $F_{BEFORE}$. Thereafter, the process 1500 repeats tasks 1524, 1526, 1528, and 1530, as depicted in FIG. 25. Accordingly, the subsequent comparative measure of force $F_{AFTER}$ for a previous iteration is used as the initial comparative measure of force $F_{BEFORE}$ for the next iteration. In accordance with this routine, the drive motor assembly is rewound in an incremental manner, while checking whether the equilibrium state has been reached at each iteration. This check will be repeated until $(F_{BEFORE} - F_{AFTER}) > F_{EQ}$, or until the maximum rewind count RET is exceeded at query task 1532.

Figure 26:
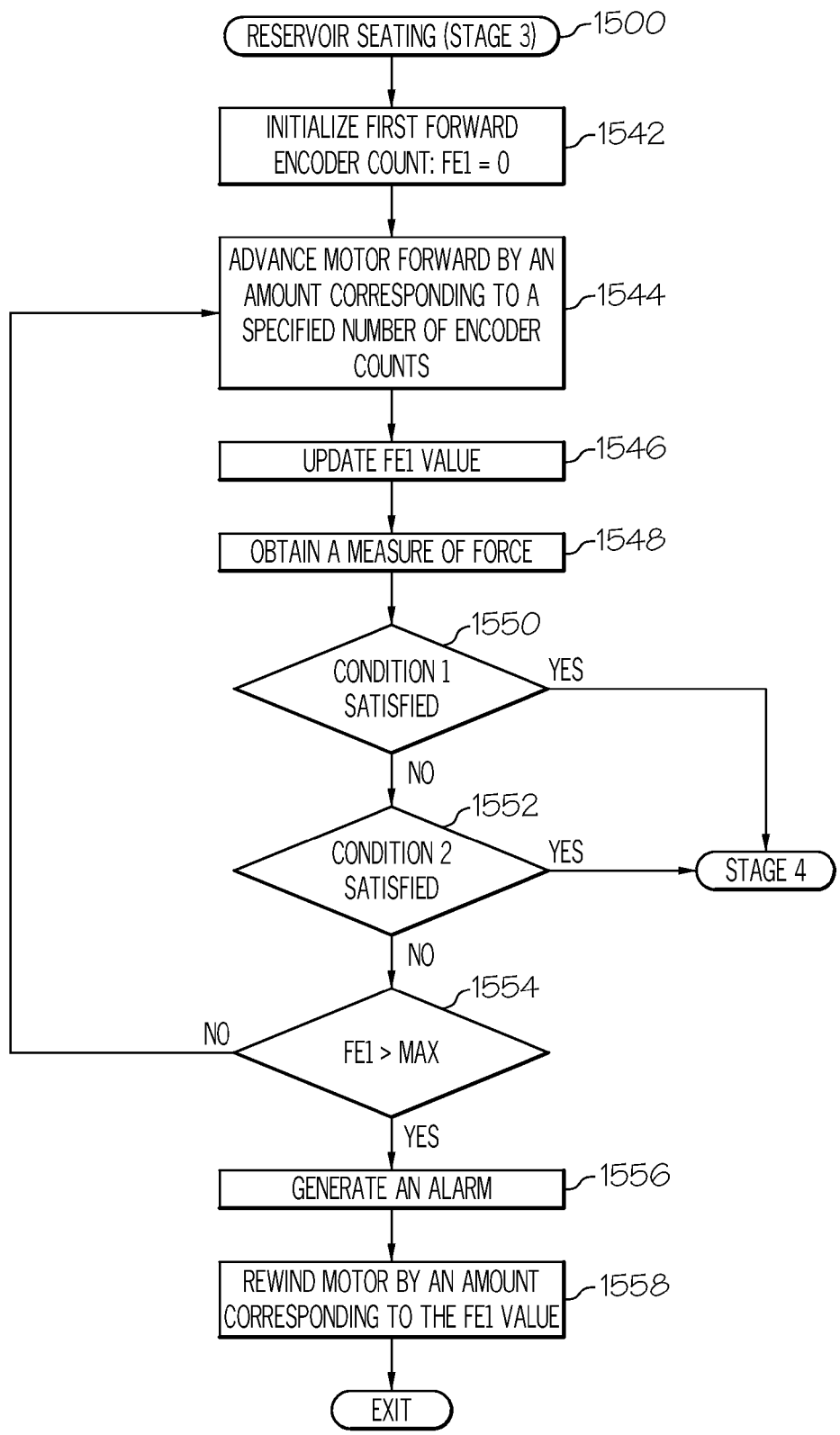

Referring now to FIG. 26, the third stage of the process 1500 is performed in an attempt to detect a seated state for the fluid reservoir. The third stage may begin by initializing a first forward encoder count (task 1542). For this example, the first forward encoder count is represented by the variable FE1, and task 1542 resets FE1 to a value of zero. Initializing FE1 provides a reference encoder count for purposes of motor advancing operations that may occur during the process 1500, as described in more detail below.

After initializing FE1, the illustrated embodiment advances the drive motor assembly forward by a controlled amount that corresponds to a predetermined number of forward encoder counts (task 1544). Although the specific number of encoder counts utilized during task 1544 may vary from one embodiment to another, and may vary from one iteration of task 1544 to another, the exemplary embodiment described here advances the drive motor assembly by one encoder count during each iteration of task 1544. This effectively results in continuous monitoring of force. For this particular embodiment, the advancing that occurs during task 1544 is performed in a controlled manner with specified motor control parameters. For example, the advancing during task 1544 may be performed using a designated pulse per second setting (FwdPPS) and a designated pulse-width modulation duty cycle (FwdPWM). Notably, FwdPPS may be different than RwdPPS, and FwdPWM may be different than RwdPWM. For example, in certain preferred embodiments FwdPWM is lower than RwdPWM, which is desirable to facilitate quick termination of the advancing with little to no inertia. In certain embodiments, the value of FwdPWM may be within the range of about 50% to about 80% (this value is selected as a safety measure such that the drive motor stalls at lower forces in the event of a bad force sensor). It should be appreciated that an embodiment may utilize different values for this setting, and that the exemplary nominal values provided here are not intended to restrict the scope or application of the process 1500.

Following task 1544, the process 1500 continues to a task 1546 to update the value of FE1, which is the first forward encoder count initialized at task 1542. The value of FE1 is updated by adding the number of forward encoder counts associated with the immediately preceding iteration of task 1544 to the current value of FE1. Thus, FE1 represents an ongoing accumulated count that represents the total amount that the drive motor assembly has been advanced during this initial seating procedure.

The process 1500 continues by obtaining and saving a respective measure of force using the force sensor (task 1548). For this particular example, the measure of force obtained at task 1548 is based on a single force reading. In an alternative embodiment, however, this measure of force could be based on a plurality of different force readings (e.g., an average of collected force readings, a maximum value, a minimum value, or the like).

The exemplary embodiment of the process 1500 described here checks for the initial seated condition using two different algorithms executing in parallel. For simplicity, however, the two different approaches are illustrated and described in sequential order. It should be appreciated that an embodiment may perform both checks concurrently, or in any order. Thus, the process 1500 determines whether a first seated condition is satisfied (query task 1550) and/or a second seated condition is satisfied (query task 1552). If either of these conditions is satisfied, then the process 1500 assumes that the fluid reservoir is initially seated, and the process 1500 proceeds to a fourth stage (see FIG. 27 and related description).

More specifically, query task 1550 determines whether each of a designated number (N) of consecutive measures of force (as obtained at task 1548) exceeds a seating threshold force value (ST), where N is any integer. In certain embodiments, N is an integer greater than one. For this particular implementation, N equals three. Consequently, the determination made at query task 1550 is performed in an ongoing basis after at least three consecutive measures of force have been obtained and saved. The particular value of ST may vary from one embodiment to another, and from one iteration of query task 1550 to another. For the exemplary embodiment described here, ST remains fixed throughout the duration of the process 1500, and ST is within the range of about 0.05 to about 0.20 pounds, such as 0.115 pounds.

In contrast, query task 1552 performs a comparative force analysis that is similar to that described above for the second stage of the process 1500. This comparative force analysis considers a "window" of force measurements wherein the current measure of force is compared with a previous measure of force that occurred a designated number of samples in the past. Thus, the window may be defined as a number of force samples, a time period, or the like. More specifically, query task 1552 calculates a difference between an initial comparative measure of force (obtained during a previous iteration of task 1548) and a subsequent comparative measure of force (obtained during the last iteration of task 1548, i.e., the current measure of force), and compares the calculated difference to the seating threshold force value ST. The initial comparative measure of force may be associated with any appropriate reference point, drive motor position, motor steps, encoder count, or the like. For example, the measure of force taken a designated number of motor steps before the current motor position can be used as the initial comparative measure of force. Query task 1552 determines whether the calculated difference for each of a designated number (M) of iterations exceeds ST, where M is any integer that is greater than one. For this particular example, M equals three.

The comparisons associated with query task 1550 and query task 1552 may be performed in parallel. The comparative approach associated with query task 1552 is utilized because force sensors tend to drift to negative values as they age. In other words, when the force sensor is new, it can be calibrated to show zero force when no force is actually present, but after aging and exposure to humidity the force sensor may indicate a slight negative force reading (e.g., negative 0.15 pounds) when no force is present. Assuming that the force sensor is calibrated only once at the time of manufacturing, there is no practical opportunity to recalibrate the force sensor. Accordingly, any drifting in the force sensor will introduce inaccuracies in the first approach (threshold based comparison). Thus, the "window" comparison approach is utilized to consider a difference in force values rather than absolute force values. The combination of the two different approaches enhances the accuracy and robustness of the process 1500.

If neither seated condition is satisfied for the current measurement iteration, then the process 1500 assumes that seating of the fluid reservoir has not been detected. The illustrated embodiment of the process 1500 checks whether the current value of FE1 exceeds a maximum allowable count (query task 1554). Thus, the process 1500 determines whether a total amount of forward advancing performed while attempting to obtain the initial seated state exceeds a maximum allowable amount. If query task 1554 determines that FE1 is greater than the maximum allowable count, then an appropriate alarm is generated (task 1556) and the process 1500 rewinds the drive motor assembly by an amount that corresponds to the current FE1 value (task 1558). The rewinding at task 1558 is desirable to return the fluid reservoir to the equilibrium state achieved upon completion of the second stage of the process 1500 (see FIG. 25). Although the maximum count used for query task 1554 may vary from one embodiment to another, the exemplary implementation described here employs a value of 1,650 for this count. Consequently, if the initial seated state is not detected within 1,650 forward encoder counts, the alarm is generated at task 1556.

If the maximum forward encoder count has not been exceeded (the "No" branch of query task 1554), then the process 1500 repeats tasks 1544, 1546, and 1548, and again checks for satisfaction of the two conditions, as depicted in FIG. 26. In accordance with this routine, the drive motor assembly is advanced in an incremental manner, while checking whether the initial seated state has been reached at each iteration. The condition checks will be repeated until one of the conditions is satisfied, or until the maximum forward encoder count is exceeded at query task 1554.

Figure 27:
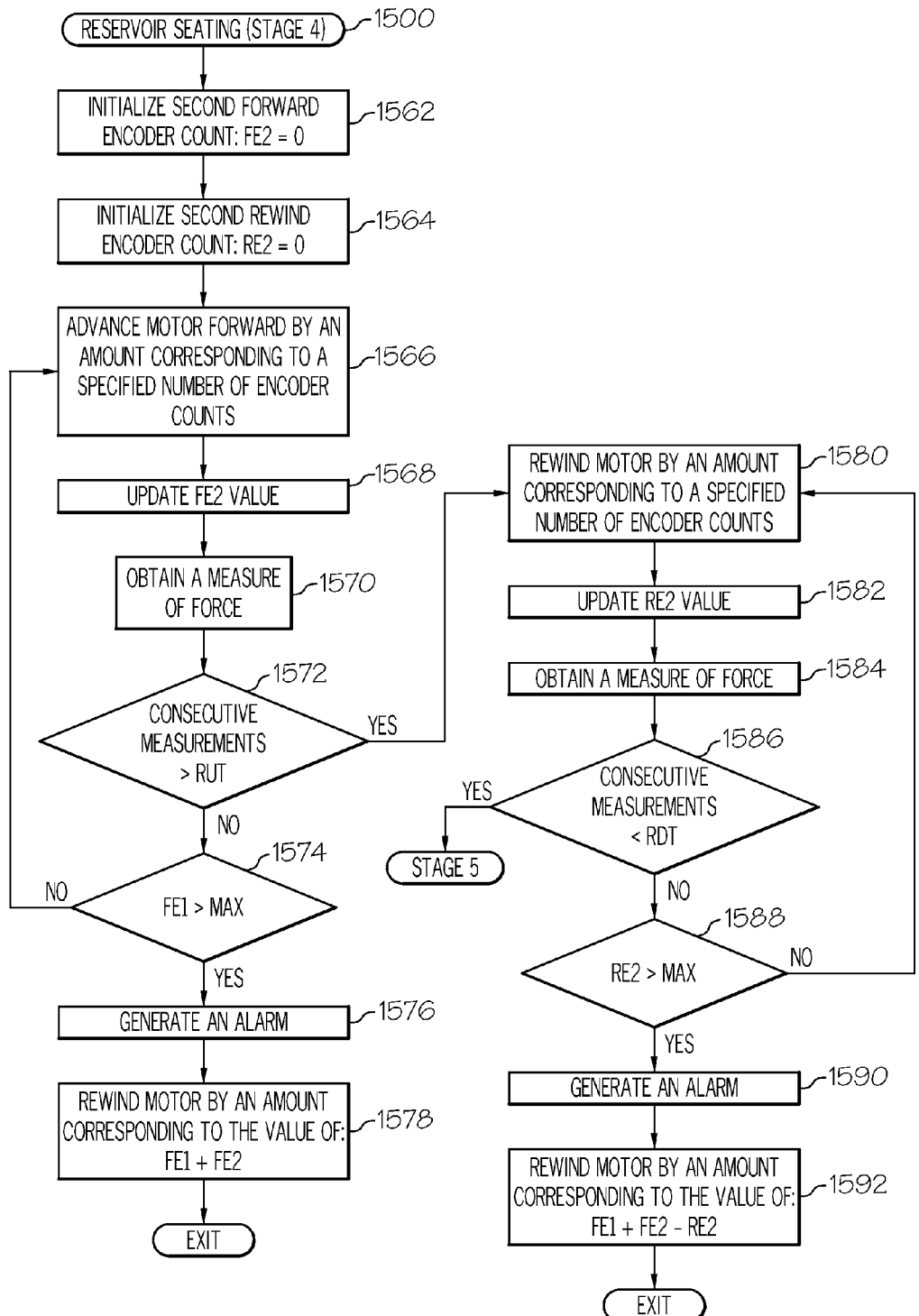

Referring now to FIG. 27, the fourth stage of the process 1500 is performed to stabilize the fluid reservoir prior to use. Thus, the fourth stage represents a stabilizing cycle that follows the initial seating procedure. For this particular embodiment, the stabilizing is performed by "pulsing" the force associated with the fluid reservoir. The first portion of the stabilizing cycle ramps up the force imparted to the fluid reservoir, and the second portion of the stabilizing cycle ramps the force down. Although multiple stabilizing cycles may be performed, the embodiment presented here completes only one cycle, i.e., the reservoir force is ramped up once and then ramped down once.

The fourth stage of the process 1500 may begin by initializing a second forward encoder count (task 1562) and initializing a second rewind encoder count (task 1564). For this example, the second forward encoder count is represented by the variable FE2, the second rewind encoder count is represented by the variable RE2, task 1562 resets FE2 to a value of zero, and task 1564 resets RE2 to a value of zero. FE2 and RE2 represent reference encoder counts associated with advancing and rewinding operations that occur during the fourth stage.

Next, the illustrated embodiment advances the drive motor assembly forward by a controlled amount that corresponds to a predetermined number of forward encoder counts (task 1566). Although the specific number of encoder counts utilized during task 1566 may vary from one embodiment to another, and may vary from one iteration of task 1566 to another, the exemplary embodiment described here advances the drive motor assembly by one encoder count during each iteration of task 1566. For this particular embodiment, the advancing that occurs during task 1566 is performed in a controlled manner with specified motor control parameters. For example, the advancing during task 1566 may be performed using a designated pulse per second setting (RaUp-PPS) and a designated pulse-width modulation duty cycle (RaUpPWM). Notably, RaUpPPS may be different than RwdPPS and/or FwdPPS, and RaUpPWM may be different than RwdPWM and/or FwdPWM.

Following task 1566, the process 1500 updates the value of FE2 (task 1568). The value of FE2 is updated by adding the number of forward encoder counts associated with the immediately preceding iteration of task 1566 to the current value of FE2. Thus, FE2 represents an ongoing accumulated count that represents the total amount that the drive motor assembly has been advanced during the stabilizing procedure.

The process 1500 continues by obtaining and saving a corresponding measure of force using the force sensor (task 1570). The measure of force obtained at task 1570 is preferably based on a single force reading, which effectively results in continuous force monitoring. In alternative embodiments, the measure of force could be based on a plurality of different force readings (e.g., an average of collected force readings, a maximum value, a minimum value, or the like).

The exemplary embodiment of the process 1500 continues by determining whether each of a designated number of consecutive measures of force (as obtained at task 1570) exceeds a ramp up threshold force value (RUT). For this particular example, query task 1572 checks whether three consecutive measures of force exceed RUT. The particular value of RUT may vary from one embodiment to another, and from one iteration of query task 1572 to another. For the exemplary embodiment described here, RUT remains fixed throughout the duration of the process 1500, and RUT is within the range of about 0.5 to about 1.5 pounds, e.g., one pound.

If three consecutive measures of force do not exceed RUT (the "No" branch of query task 1572), then the process 1500 assumes that the ramp up seating state has not been reached, and the process 1500 checks whether the current value of FE2 exceeds a maximum allowable count (query task 1574). Thus, the process 1500 determines whether a total amount of forward advancing performed during the stabilizing routine exceeds a maximum allowable amount. If query task 1574 determines that FE2 is greater than the maximum allowable count, then an appropriate alarm is generated (task 1576) and the process 1500 rewinds the drive motor assembly by an amount that corresponds to the current FE1 value plus the current FE2 value (task 1578). The rewinding at task 1578 is desirable to return the fluid reservoir to the equilibrium state achieved upon completion of the second stage of the process 1500 (see FIG. 25). Although the maximum count used for query task 1574 may vary from one embodiment to another, the exemplary implementation described here employs a value of 741 for this count. Consequently, if the ramp up threshold force is not detected within 741 forward encoder counts, the alarm is generated at task 1576.

If the maximum forward encoder count has not been exceeded (the "No" branch of query task 1574), then the process 1500 repeats tasks 1566, 1568, and 1570, and again checks for satisfaction of the RUT criteria in query task 1572. In accordance with this routine, the drive motor assembly is advanced in an incremental manner, while checking whether the ramp up force has been reached at each iteration. This routine will be repeated until the ramp up force has been reached, or until the maximum forward encoder count for FE2 is exceeded at query task 1574.

This description assumes that the "Yes" branch of query task 1572 is followed, i.e., the ramp up force criteria is satisfied within the maximum allowed encoder count for FE2. At this time, the process 1500 rewinds the drive motor assembly by a controlled amount that corresponds to a predetermined number of rewind encoder counts (task 1580). Although the specific number of encoder counts utilized during task 1580 may vary from one embodiment to another, and may vary from one iteration of task 1580 to another, the exemplary embodiment described here rewinds the drive motor assembly by one encoder count during each iteration of task 1580, which effectively results in continuous force monitoring. For this particular embodiment, the rewinding that occurs during task 1580 is performed in a controlled manner with specified motor control parameters. For example, the rewinding during task 1580 may be performed using a designated pulse per second setting (RaDoPPS) and a designated pulse-width modulation duty cycle (RaDoPWM). Notably, RaDoPPS may be different than RwdPPS, FwdPPS, and/or RaUpPPS, and RaDoPWM may be different than RwdPWM, FwdPWM, and/or RaUpPWM.

Following task 1580, the process 1500 updates the value of RE2 (task 1582). The value of RE2 is updated by adding the number of rewind encoder counts associated with the immediately preceding iteration of task 1580 to the current value of RE2. Thus, RE2 represents an ongoing accumulated count that represents the total amount that the drive motor assembly has been rewound during the stabilizing procedure.

The process 1500 continues by obtaining and saving a corresponding measure of force using the force sensor (task 1584). The measure of force obtained at task 1584 may be based on a single force reading, or it may be based on a plurality of different force readings (e.g., an average of collected force readings, a maximum value, a minimum value, or the like). For this particular embodiment, task 1584 calculates the measure of force based on a single force reading.

The exemplary embodiment of the process 1500 continues by determining whether each of a designated number of consecutive measures of force (as obtained at task 1584) is less than a ramp down threshold force value (RDT). For this particular example, query task 1586 checks whether three consecutive measures of force are less than RDT. The particular value of RDT may vary from one embodiment to another, and from one iteration of query task 1586 to another. For the exemplary embodiment described here, RDT remains fixed throughout the duration of the process 1500, and RDT is within the range of about 0.0 to about 0.5 pounds, e.g., 0.115 pounds.

If three consecutive measures of force are not less than RDT (the "No" branch of query task 1586), then the process 1500 assumes that the ramp down seating state has not been reached, and the process 1500 checks whether the current value of RE2 exceeds a maximum allowable count (query task 1588). Thus, the process 1500 determines whether a total amount of rewinding performed during the stabilizing routine exceeds a maximum allowable amount. If query task 1588 determines that RE2 is greater than the maximum allowable count, then an appropriate alarm is generated (task 1590) and the process 1500 rewinds the drive motor assembly by an amount that corresponds to the current FE1 value plus the current FE2 value minus the current RE2 value (task 1592). The rewinding at task 1592 is desirable to return the fluid reservoir to the equilibrium state achieved upon completion of the second stage of the process 1500 (see FIG. 25). Although the maximum count used for query task 1588 may vary from one embodiment to another, the exemplary implementation described here employs a value of 522 for this count. Consequently, if the ramp down threshold force is not detected within 522 rewind encoder counts, the alarm is generated at task 1590.

If the maximum rewind encoder count has not been exceeded (the "No" branch of query task 1588), then the process 1500 repeats tasks 1580, 1582, and 1584, and again checks for satisfaction of the RDT criteria in query task 1586. In accordance with this routine, the drive motor assembly is rewound in an incremental manner, while checking whether the ramp down force has been reached at each iteration. This routine will be repeated until the ramp down force has been reached, or until the maximum rewind encoder count for RE2 is exceeded at query task 1588. When the ramp down force is detected at query task 186, the process 1500 continues to its fifth stage.

Figure 28:
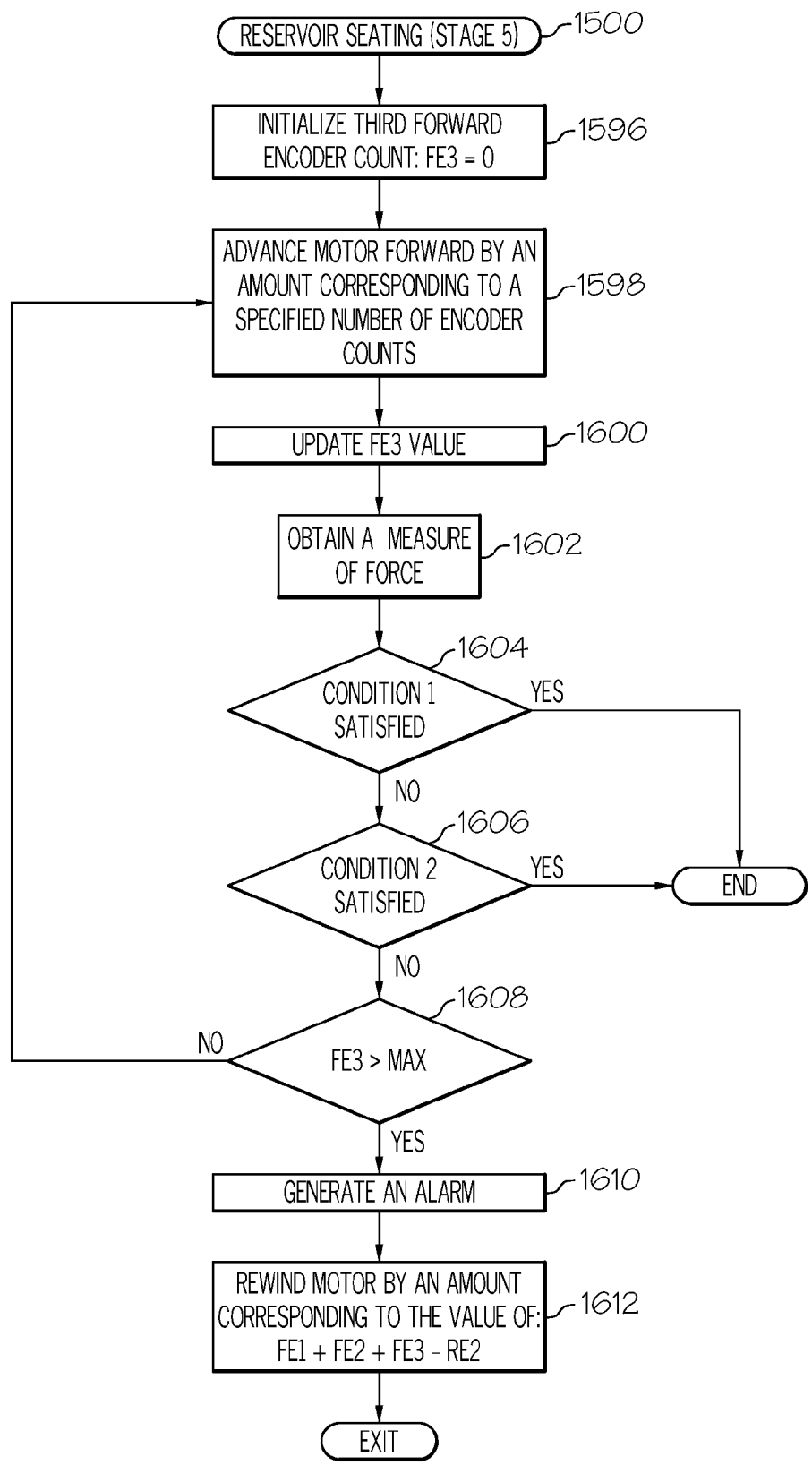

Referring now to FIG. 28, the fifth stage of the process 1500 is performed to obtain a subsequent seated state for the fluid reservoir. Much of the fifth stage is similar to the third stage, which obtains the initial seated state. Accordingly, the following description of the fifth stage will be abbreviated.

The fifth stage may begin by initializing a third forward encoder count to a starting value, such as zero (task 1596). Thereafter, the drive motor assembly is advanced forward by a controlled amount that corresponds to a predetermined number of forward encoder counts (task 1598). Although the specific number of encoder counts utilized during task 1598 may vary from one embodiment to another, and may vary from one iteration of task 1598 to another, the exemplary embodiment described here advances the drive motor assembly by one encoder count during each iteration of task 1598. For this particular embodiment, the advancing that occurs during task 1598 is performed in a controlled manner using the settings FwdPPS and FwdPWM.

Following task 1598, the process 1500 updates the value of FE3 (task 1600) and obtains and saves a respective measure of force using the force sensor (task 1602). The measure of force obtained at task 1602 is preferably based on a single force reading. In alternative implementations, the measure of force could be based on a plurality of different force readings (e.g., an average of collected force readings, a maximum value, a minimum value, or the like).

The exemplary embodiment of the process 1500 described here checks for the subsequent (final) seated condition using two different algorithms executing in parallel, as described above for the third stage (see FIG. 26). The first condition tested at query task 1604 is similar to the first condition described above with reference to query task 1550. The comparison performed at query task 1604, however, may employ a different seating threshold force value (ST2). Thus, query task 1604 checks whether each of three consecutive measures of force exceed ST2. The second condition tested at query task 1606 is similar to the condition described above with reference to query task 1552. The comparison performed at query task 1606, however, may employ a different seating threshold force value (ST2). Thus, query task 1606 determines whether the calculated difference for three iterations exceeds ST2. Although the above description suggests that ST2 and ST are two different values, the value of ST2 may be equal to the value of ST in certain embodiments.

If neither seated condition is satisfied for the current measurement iteration, then the process 1500 assumes that final seating of the fluid reservoir has not been detected. Accordingly, the process 1500 checks whether the current value of FE3 exceeds a maximum allowable count (query task 1608). If query task 1608 determines that FE3 is greater than the maximum allowable count, then an appropriate alarm is generated (task 1610) and the process 1500 rewinds the drive motor assembly by an amount that corresponds to: FE1+FE2+FE3−RE2 (task 1612).

If the maximum forward encoder count has not been exceeded (the "No" branch of query task 1608), then the process 1500 repeats tasks 1598, 1600, and 1602, and again checks for satisfaction of the two conditions, as depicted in FIG. 28. In accordance with this routine, the drive motor assembly is advanced in an incremental manner, while checking whether the subsequent seated state has been reached at each iteration. The condition checks will be repeated until one of the conditions is satisfied, or until the maximum forward encoder count is exceeded at query task 1608. If the final seated state is detected (the "Yes" branch of query task 1604 or the "Yes" branch of query task 1606), then the process 1500 ends. At this time, the fluid reservoir and the drive system is prepared, and the durable housing can be installed onto the base plate for normal operation of the fluid delivery device.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of seating a fluid reservoir in a housing of a fluid infusion device prior to establishing an outgoing fluid flow path from the fluid reservoir, the fluid infusion device comprising a drive motor assembly for the fluid reservoir, the method comprising:
    detecting insertion of the fluid reservoir into the housing;
    in response to the detecting, determining whether the fluid reservoir is in need of depressurization;
    when the fluid reservoir is in need of depressurization, rewinding the drive motor assembly to depressurize the fluid reservoir;
    after depressurizing the fluid reservoir, achieving an equilibrium state for the fluid reservoir; and
    after achieving the equilibrium state, advancing the drive motor assembly to obtain an initial seated state for the fluid reservoir.

2. The method of claim 1, further comprising:
    after advancing the drive motor assembly to obtain the initial seated state, coupling the fluid reservoir to a fluid delivery conduit to deliver fluid from the fluid reservoir to a user.

3. The method of claim 1, wherein:
    rewinding the drive motor assembly to depressurize the fluid reservoir is performed using a first pulse-width modulation duty cycle;
    advancing the drive motor assembly to obtain the initial seated condition is performed using a second pulse-width modulation duty cycle; and
    the first pulse-width modulation duty cycle is different than the second pulse-width modulation duty cycle.

4. The method of claim 1, further comprising:
    after advancing the drive motor assembly to obtain the initial seated state, performing a stabilizing cycle with the drive motor assembly; and
    after completing the stabilizing cycle, advancing the drive motor assembly to obtain a subsequent seated state for the fluid reservoir.

5. The method of claim 4, wherein the subsequent seated state is identical to the initial seated state.

6. The method of claim 4, wherein performing the stabilizing cycle comprises:
    advancing the drive motor assembly by a first amount; and
    thereafter, rewinding the drive motor assembly by a second amount.

* * * * *